US010451632B2

(12) United States Patent
Bertozzi et al.

(10) Patent No.: US 10,451,632 B2
(45) Date of Patent: Oct. 22, 2019

(54) CLEAVABLE PROBES FOR ISOTOPE TARGETED GLYCOPROTEOMICS AND METHODS OF USING THE SAME

(71) Applicant: The Regents of the University of California, Oakland, CA (US)

(72) Inventors: Carolyn R. Bertozzi, Stanford, CA (US); Christina Woo, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/167,181

(22) Filed: Oct. 22, 2018

(65) Prior Publication Data
US 2019/0094238 A1 Mar. 28, 2019

Related U.S. Application Data

(62) Division of application No. 14/958,730, filed on Dec. 3, 2015, now Pat. No. 10,114,026.
(Continued)

(51) Int. Cl.
*C07F 5/02* (2006.01)
*C07F 7/18* (2006.01)
(Continued)

(52) U.S. Cl.
CPC ........... *G01N 33/6848* (2013.01); *C07F 5/00* (2013.01); *C07F 7/1804* (2013.01); *C07K 1/13* (2013.01);
(Continued)

(58) Field of Classification Search
CPC . C07F 7/184; C07F 5/025; C07F 7/18; C07K 1/13; G01N 33/6842; G01N 33/6848; G01N 2440/38; G01N 2458/15; G01N 2560/00; G01N 2570/00; G01N 33/58; G01N 33/532; G01N 33/68
See application file for complete search history.

(56) References Cited

PUBLICATIONS

Bond, et al.; "Chemical methods for glycoprotein discovery"; Current Opinion in Chemical Biology; vol. 11, pp. 52-58 (2007).
(Continued)

*Primary Examiner* — Shafiqul Haq
(74) *Attorney, Agent, or Firm* — Bozicevic Field & Francis, LLP; Paula A. Borden; Kelly A. Tipson

(57) ABSTRACT

Methods for producing isotopically-labelled peptides are provided. Aspects of the method include: contacting a sample including a metabolically tagged protein with a cleavable probe to produce a probe-protein conjugate; separating the probe-protein conjugate from the sample; digesting the probe-protein conjugate to produce a probe-peptide conjugate; and cleaving a cleavable linker to release an isotopically labelled peptide. The method may further include: identifying a predetermined isotopic pattern in a mass spectrum; determining an amino acid sequence of the isotopically labelled peptide; and identifying the site of protein glycosylation based on the determined amino acid sequence. Also provided are cleavable probes for practicing the subject methods, described by the Formula: A-L-(M-Z) where A is an affinity tag, L is a cleavable linker, M is an isotopic label and Z is a chemoselective tag capable of cross-linking a metabolically tagged protein. Compositions and kits for practicing the subject methods are also provided.

17 Claims, 19 Drawing Sheets

Specification includes a Sequence Listing.

Related U.S. Application Data

(60) Provisional application No. 62/088,356, filed on Dec. 5, 2014.

(51) Int. Cl.
  *G01N 33/58* (2006.01)
  *G01N 33/534* (2006.01)
  *C07K 1/13* (2006.01)
  *G01N 33/68* (2006.01)
  *C07F 5/00* (2006.01)

(52) U.S. Cl.
  CPC ..... *G01N 2440/38* (2013.01); *G01N 2458/15* (2013.01)

(56) References Cited

PUBLICATIONS

Boyce et al.; "Metabolic cross-talk allows labeling of O-linked β-N-acetylglucosamine-modified proteins via the N-acetylgalactosamine salvage pathway"; PNAS; vol. 108, No. 8, pp. 3141-3146 (Feb. 22, 2011).

Chuh, et al.; "Changes in Metabolic Chemical Reporter Structure Yield a Selective Probe of O—GlcNAc Modification"; J. Am. Chem. Soc.; vol. 136, pp. 12283-12295 (2014).

Fauq, et al.; Synthesis of Acid-Cleavable Light Isotope-Coded Affinity Tags (ICAT-L) for Potential Use in Proteomic Expression Profiling Analysis; Bioconjugate Chem.; vol. 17, pp. 248-254 (2006).

Hägglund, et al.; "A New Strategy for Identification of N-Glycosylated Proteins and Unambiguous Assignment of Their Glycosylation Sites Using HILIC Enrichment and Partial Deglycosylation"; Journal of Proteome Research; vol. 3, pp. 556-566 (2004).

Hubbard, et al.; "Cell surface glycoproteomic analysis of prostate cancer-derived PC-3 cells"; Bioorganic & Medicinal Chemistry Letters; vol. 21, pp. 4945-4950 (2011).

Khidekel, et al.; "Probing the dynamics of O—GlcNAc glycosylation in the brain using quantitative proteomics"; Nature Chemical Biology; vol. 3, No. 6, pp. 339-348 (Jun. 2007).

Nilsson, et al.; "Enrichment of glycopeptides for glycan structure and attachment site identification"; Nature Methods; vol. 6, No. 11, pp. 809-811 (Nov. 2009).

Palaniappan, et al.; "Isotopic Signature Transfer and Mass Pattern Prediction (IsoStamp): An Enabling Technique for Chemically-Directed Proteomics"; ACS Chem. Biol.; vol. 6, pp. 829-836 (2011).

Pitcher, et al.; "New Tools for Chemically Directed Proteomics"; Dissertation, Doctor of Philosophy; Graduate Division, University of California at Berkeley, California, USA; pp. 1-271 (2010).

Steentoft, et al.; "Precision mapping of the human O—GalNAc glycoproteome through SimpleCell technology"; The EMBO Journal; vol. 32, No. 10, pp. 1478-1488 (2013).

Steentoft, et al.; "Mining the O-glycoproteome using zinc-finger nuclease—glycoengineered SimpleCell lines"; Nature Methods; vol. 8, No. 11, pp. 977-982 (Nov. 2011).

Szychowski, et al.; "Cleavable Biotin Probes for Labeling of Biomolecules via Azide-Alkyne Cycloaddition"; J. Am. Chem. Soc.; vol. 132, pp. 18351-18360 (2010).

Trinidad, et al.; "N- and O-Glycosylation in the Murine Synaptosome"; Molecular & Cellular Proteomics; vol. 12, pp. 3474-3488 (2013).

Vosseller, et al.; "O-Linked N-Acetylglucosamine Proteomics of Postsynaptic Density Preparations Using Lectin Weak Affinity Chromatography and Mass Spectrometry"; Molecular & Cellular Proteomics; vol. 5, pp. 923-934 (2006).

Woo, et al.; "Isotope-targeted glycoproteomics (IsoTaG): a mass-independent platform for intact N- and O-glycopeptide discovery and analysis"; Nature Methods; vol. 12, No. 6, pp. 561-567 (Jun. 2015).

Zaro, et al.; "Chemical reporters for fluorescent detection and identification of O—GlcNAc-modified proteins reveal glycosylation of the ubiquitin ligase NEDD4-1"; PNAS; vol. 108, No. 20, pp. 8146-8151 (May 17, 2011).

Zhang, et al.; "Identification and quantification of N-linked glycoproteins using hydrazide chemistry, stable isotope labeling and mass spectrometry"; Nature Biotechnology; vol. 21, No. 6, pp. 660-666 (Jun. 2003).

Zielinska, et al.; "Precision Mapping of an In Vivo N-Glycoproteome Reveals Rigid Topological and Sequence Constraints"; Cell; vol. 141, pp. 897-907 (May 28, 2010).

FIG. 3A N-glycan structures identified
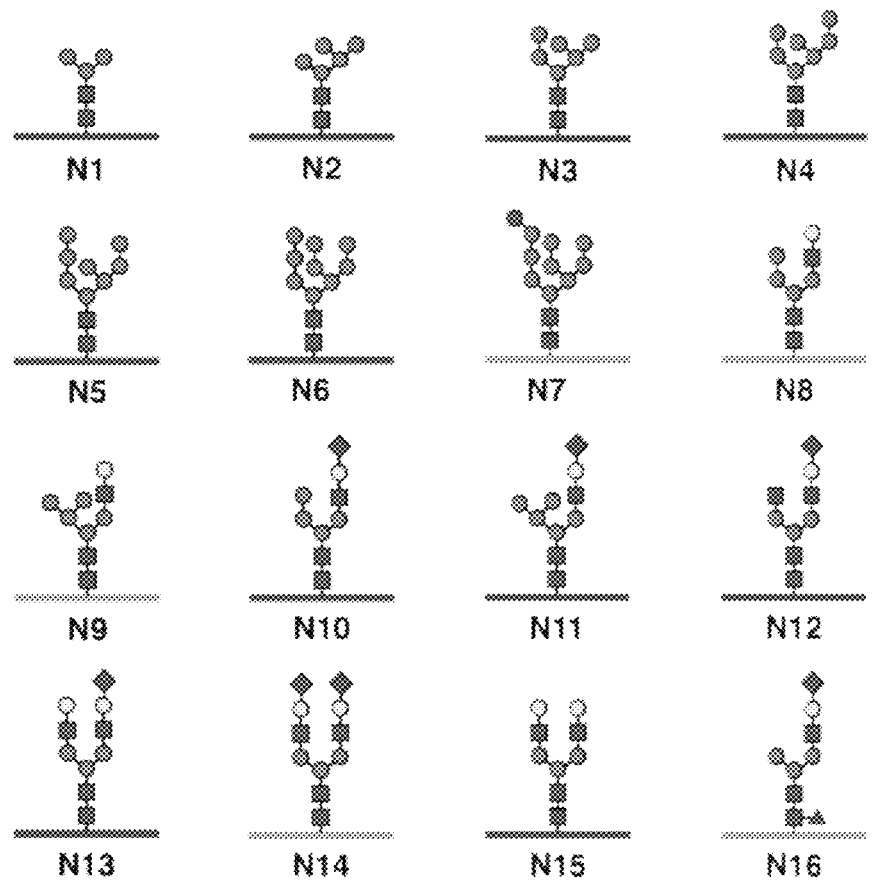
FIG. 3B O-glycan structures identified
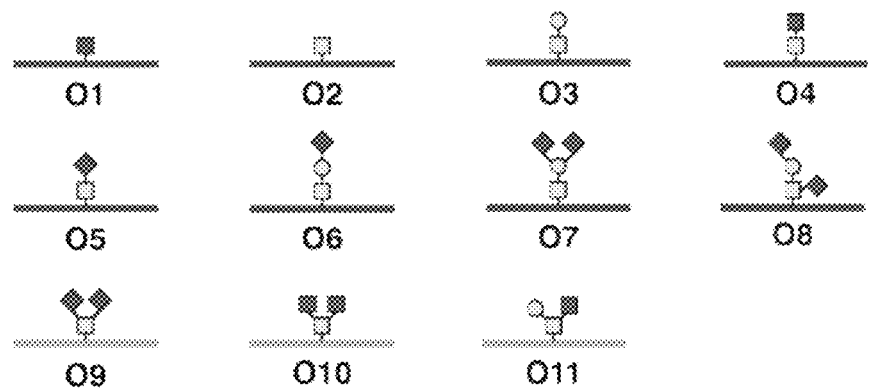

CLEAVABLE PROBES FOR ISOTOPE TARGETED GLYCOPROTEOMICS AND METHODS OF USING THE SAME

CROSS-REFERENCE

This application claims the benefit of U.S. Provisional Patent Application No. 62/088,356, filed Dec. 5, 2014, which application is incorporated herein by reference in its entirety.

STATEMENT REGARDING FEDERALLY SPONSORED RESEARCH

This invention was made with government support under Grant No. GM066047 awarded by the National Institutes of Health. The government has certain rights in the invention.

INTRODUCTION

Protein glycosylation is one of the most ubiquitous forms of post-translational modifications (PTMs). In eukaryotes, glycans may be attached to proteins at asparagine (N-glycans) or serine/threonine (O-glycans) side chains. Glycoproteins participate in protein folding and trafficking, regulate signaling pathways, and mediate cell-cell interactions in immune response. Dynamic changes in protein glycosylation may accompany cancer progression, and specific protein glycoforms, and the enzymes that generate them, may serve as disease biomarkers and therapeutic targets. Methods to profile the intact glycoproteome would enable the study of glycoprotein biosynthesis and biological function.

Analysis of intact glycopeptides by mass spectrometry is complicated by glycan heterogeneity and the substoichiometric nature of a particular glycoform, which leads to reduced detection by mass spectrometry. Additionally, the heterogeneity and lower ionization efficiencies of glycopeptides stymie detection and complicate computational analysis. As most proteomics platforms rely on database searches for peptide identification, nontemplated PTMs (e.g., glycosylation) or uncharacterized peptide sequence polymorphisms (pSPs) present significant computational challenges on the proteome level. These complexities often necessitate the reduction of the glycan to a uniform and predictable mass followed by extensive chromatography for glycopeptide identification. Reduction in glycan heterogeneity via enzymatic digestion (N-glycans: PNGase F and EndoH) and genetic engineering (O-glycans: Simple Cell) has greatly advanced glycosite analysis. However, truncation of the glycan destroys information correlating glycan structure to the protein attachment site and, in turn, prevents further assessment of biological function.

SUMMARY

Methods for producing isotopically-labelled peptides are provided. Aspects of the method include: contacting a sample including a metabolically tagged protein with a cleavable probe to produce a probe-protein conjugate; separating the probe-protein conjugate from the sample; digesting the probe-protein conjugate to produce a probe-peptide conjugate; and cleaving a cleavable linker to release an isotopically labelled peptide. The method may further include: identifying a predetermined isotopic pattern in a mass spectrum; determining an amino acid sequence of the isotopically labelled peptide; and identifying the site of protein glycosylation based on the determined amino acid sequence. Also provided are cleavable probes for practicing the subject methods, described by the Formula: A-L-(M-Z) where A is an affinity tag, L is a cleavable linker, M is an isotopic label and Z is a chemoselective tag capable of cross-linking a metabolically tagged protein. Compositions and kits for practicing the subject methods are also provided.

The present disclosure provides a method for producing an isotopically-labelled peptide, the method comprising: a) contacting a sample including a metabolically tagged protein with a cleavable probe under conditions sufficient to produce a probe-protein conjugate, wherein the cleavable probe is described by Formula (I): A-L-(M-Z); wherein: A is an affinity tag; L is a cleavable linker; M is an isotopic label; and Z is a chemoselective tag capable of cross-linking the metabolically tagged protein; b) separating the probe-protein conjugate from the sample; c) digesting the probe-protein conjugate to produce a probe-peptide conjugate; and d) cleaving the cleavable linker to release the isotopically labelled peptide. In some cases, the metabolically tagged protein is a metabolically tagged glycosylated protein and the isotopically labelled peptide is an isotopically labelled glycopeptide. In some cases, the sample is obtained from a eukaryotic cell comprising the metabolically tagged glycosylated protein. In some cases, the method further comprises contacting the cell with a tagged sugar under conditions sufficient to produce the metabolically tagged glycosylated protein. In some cases, the method further comprises: i) identifying a predetermined isotopic pattern in a mass spectrum; b) determining an amino acid sequence of the isotopically labelled peptide; and c) identifying the site of glycosylation on the protein based on the determined amino acid sequence; in some of these embodiments, the identifying step includes identifying isotopically labeled peptides by full scan mass spectrometry prior to tandem MS analysis. In some cases, wherein the metabolically tagged protein comprises a chemoselective tag. In some cases, the chemoselective tag is an azide. In some cases, Z is a chemoselective tag selected from the group consisting of an alkyne, an azide, a phosphine, a thiol, a maleimide or iodoacetyl, an aldehyde, an alkoxyamine. In some cases, Z is an alkyne; in some of these embodiments, Z and the metabolically tagged protein cross-link via copper-catalyzed azide-alkyne [3+2] cycloaddition to produce the probe-protein conjugate. In some cases, A is a biotin moiety. In some cases, L is described by the formula: $-L^1-X-L^2-$, wherein $L^1$ and $L^2$ are optional linkers and X is a cleavable group. In some cases, X is $-O-Si(R)_2-O-$, wherein each R is independently selected from hydrogen, an aryl, a substituted aryl, an alkyl and a substituted alkyl. In some cases, L is a cleavable silane linker. In some cases, M comprises two or more bromine atoms. In some cases, M is described by the formula: $-(CH_2)_n-CH(Br)=CH(Br)-(CH_2)_m-$, wherein n and m are each independently 0-6. In some of the embodiments described above and elsewhere herein, the tagged sugar and the produced metabolically tagged protein comprise an isotopic label. In some cases, the method further comprises quantitating a glycoprotein of the sample. In some cases, the method further comprises: i) contacting the sample with a protein probe capable of cross-linking an amino acid residue of the protein to produce a labelled protein; and ii) digesting the labelled protein to produce a labelled peptide; in some of these embodiments, the method further comprises quantitating a protein of the sample.

The present disclosure provides a cleavable probe of Formula (I): A-L-(M-Z); wherein A is an affinity tag; L is a cleavable linker; M is an isotopic label; and Z is a chemoselective tag. In some cases, Z is a chemoselective tag selected from the group consisting of an alkyne, an azide, a phosphine, a thiol, a maleimide or iodoacetyl, an aldehyde, a hydrazide and an alkoxyamine. In some cases, Z is an alkyne. In some cases, A is a biotin moiety. In some cases, L is described by the formula: -$L^1$-X-$L^2$-, wherein $L^1$ and $L^2$ are optional linkers and X is a cleavable group. In some cases, X is —O—Si(R)$_2$—O—, wherein each R is independently selected from hydrogen, an aryl, a substituted aryl, an alkyl and a substituted alkyl. In some cases, L is a cleavable silane linker. In some cases, M comprises two or more bromine atoms. In some cases, M is described by the formula: —(CH$_2$)$_n$—CH(Br)═CH(Br)—(CH$_2$)$_m$—, wherein n and m are each independently 0-6. In some cases, the probe has the formula A-L-M-Z, wherein: A is a biotin moiety; L is -(PEG)$_n$-NH—(CH$_2$)$_m$—C(CH$_3$)$_2$—O—Si(R)$_2$—O—; M is —(CH$_2$)$_p$—CH(Br)═CH(Br)—(CH$_2$)$_q$—; and Z is an alkyne-containing group, wherein n and m are each independently 0-20 and p and q are each independently 0-6. In some cases, M comprises two or more deuterium atoms. In some cases, M comprises a mixture of components, each component independently comprising 0, 2, 4 or 6 deuterium atoms.

The present disclosure provides a kit, comprising: a cleavable probe of Formula (I): A-L-(M-Z), wherein: A is an affinity tag; L is a cleavable linker; M is an isotopic label; and Z is a chemoselective tag; and one or more components selected from the group consisting of: an enzyme, a chemical cleavage agent, a light source, a buffer, a cell, a metabolically tagged protein and a tagged sugar.

BRIEF DESCRIPTION OF THE DRAWINGS

FIG. 3A-3B illustrate the diversity of intact glycopeptides identified via chemical glycoproteomics: (a) N-glycan structures identified. (b) O-glycan structures identified include O-GlcNAc, Tn, STn, core 1, core 2, core 3, core 4, and sialylated variants. Purple peptide: glycan and peptide sequence identified for at least one glycopeptide. These species generated interpretable peptide fragments. Orange peptide: only glycan assigned. These species gave unassignable peptide fragments.

DEFINITIONS

Figure 1:
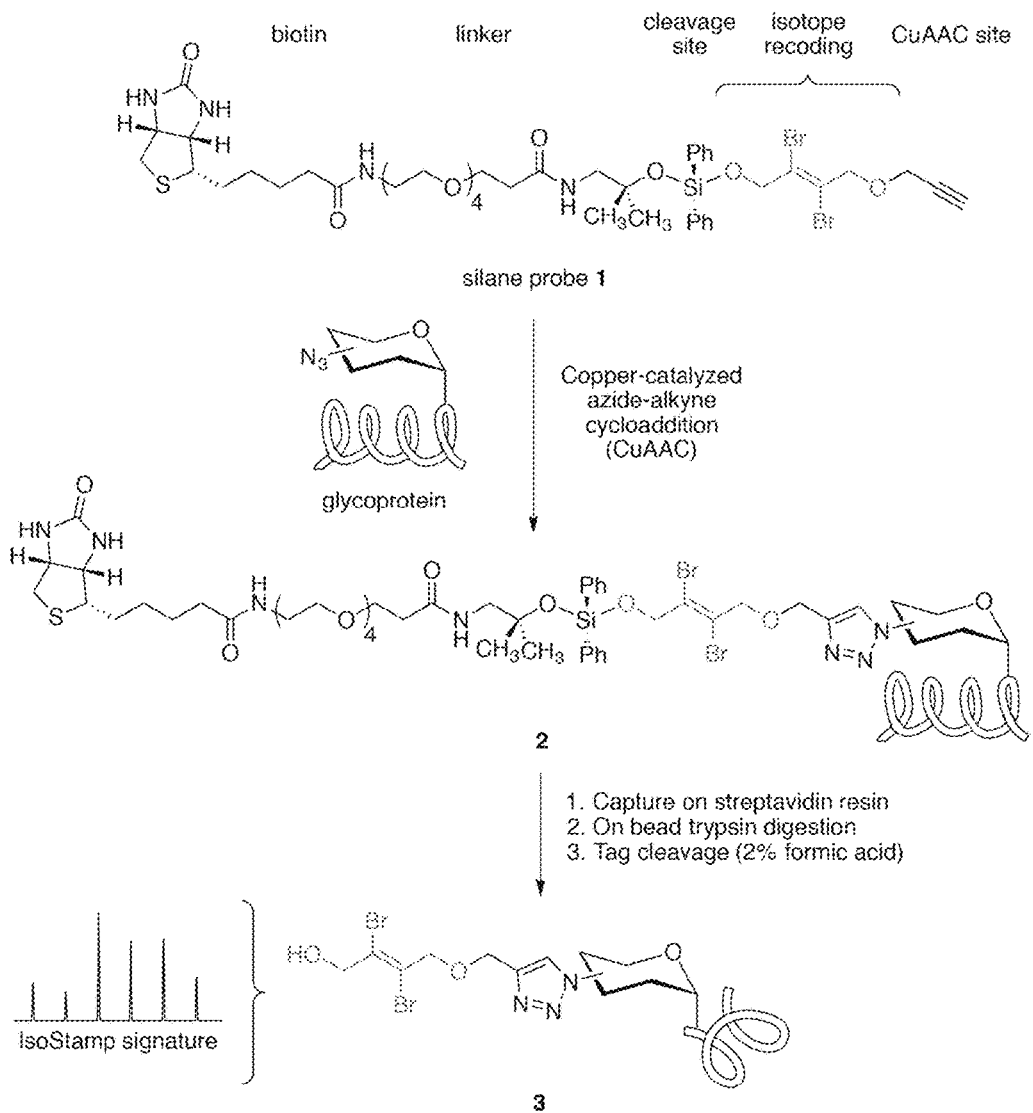
FIG. 1 provides a depiction of an exemplary cleavable probe and a method of use for mass independent glycoproteomics. Probe 1 bioorthogonally labels glycoproteins via copper-catalyzed azide-alkyne cycloaddition (CuAAC). The labelled glycoproteins 2 are enriched, digested, and the isotopically recoded glycopeptides 3 are recovered by mild acid hydrolysis.

Unless defined otherwise, all technical and scientific terms used herein have the same meaning as commonly understood by one of ordinary skill in the art to which this invention belongs. Still, certain terms are defined below for the sake of clarity and ease of reference.

As used herein, the terms "polypeptide" and "protein" are used interchangeably. The term "polypeptide" also includes post translational modified polypeptides or proteins. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 9, 10, 20, 30 or 50 amino acids. In some embodiments, peptides are between 5 and 30 amino acids in length. A peptide may be made by protease digestion of a large polypeptide.

The terms "nucleic acid," "nucleic acid molecule", "oligonucleotide" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, i.e., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, and primers.

The term "sequence" may refer to a particular sequence of bases and/or may also refer to a polynucleotide having a particular sequence of bases. Thus a sequence may be information or may refer to a molecular entity, as indicated by the context of the usage.

The term "moiety" is used to refer to a portion of an entity or molecule, in some cases having a particular function, structure, or structural feature.

The terms "antibody," "immunoglobulin" and their plural referents include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be bound to an entity that enables their detection, e.g., a radioisotope, an enzyme which generates a detectable product, a fluorescent protein, and the like. The antibodies may be further covalently or non-covalently conjugated to other moieties, such as members of specific binding pairs, e.g., biotin (member of biotin-avidin/streptavidin specific binding pair), and the like. The antibodies may also be bound to a solid support, including, but not limited to, polystyrene plates or beads, and the like. Also encompassed by the terms are Fab', Fv, F(ab')2, and or other antibody fragments that retain specific binding to antigen. Antibodies may exist in a variety of other forms including, for example, Fv, Fab, and (Fab')2, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. USA*, 85, 5879-5883 (1988); Bird et al., *Science,* 242, 423-426 (1988); see Hood et al., *Immunology*, Benjamin, N.Y., 2nd ed. (1984), and Hunkapiller and Hood, *Nature,* 323, 15-16 (1986)).

As used herein, the terms "affinity" and "avidity" have the same meaning and may be used interchangeably herein. "Affinity" refers to the strength of binding, increased binding affinity being correlated with a lower $K_D$.

The terms "bind" and "bound" as used herein refer to a binding interaction between two or more entities. Where two entities, e.g., molecules, are bound to each other, they may be directly bound, i.e., bound directly to one another, or they may be indirectly bound, i.e., bound through the use of an intermediate linking moiety or entity. In either case the binding may covalent; e.g., through covalent bonds; or non-covalent, e.g., through ionic bonds, hydrogen bonds, electrostatic interactions, hydrophobic interactions, Van der Waals forces, or a combination thereof.

The terms "specific binding," "specifically bind," and the like, refer to the ability of a first binding molecule or moiety (e.g., a target-specific binding moiety such as a capture agent or a first specific binding moiety) to preferentially bind directly to a second binding molecule or moiety (e.g., a target molecule or a second specific binding moiety) relative to other molecules or moieties in a reaction mixture. In certain embodiments, the affinity between a first binding molecule or moiety and a second binding molecule or moiety when they are specifically bound to each other is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. In some cases, the affinity between a capture agent and analyte when they are specifically bound in a capture agent/analyte complex is at least $10^{-8}$ M, at least $10^{-9}$ M, or at least $10^{-10}$ M. In some instances, a specific binding interaction will discriminate between desirable and undesirable analytes in a sample with a specificity of 10-fold or more for a desirable analyte over an undesirable analytes, such as 100-fold or more, or 1000-fold or more.

As used herein, a "member of a specific binding pair" is a member of a pair of molecules or entities that takes part in a specific binding interaction. Where a first member of the specific binding pair is identified, the identity of the second member of the specific binding pair may be readily identifiable. It should be noted that when either member of the binding pair is referred to as the first member, the remaining member is understood to be the second member and vice versa. Examples of specific binding pair interactions include immune interactions such as antigen/antibody and hapten/antibody as well as non-immune interactions such as complementary nucleic acid binding, complementary protein-protein interactions, a sugar and a lectin specific therefore, an enzyme and an inhibitor therefore, an apoenzyme and cofactor, a hormone and a receptor therefore, biotin/avidin and biotin/streptavidin.

As used herein, the term "to cross-link" refers to the process of linking two moieties or atoms to each other via a covalent bond. An exemplary cross-linking process is the reaction of two complementary chemoselective groups to produce a stable covalent linkage.

As used herein, the term "linker" or "linkage" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present invention is stable, e.g. to physiological conditions, until it is contacted with a cleavage-inducing stimulus, e.g., an agent such as an enzyme or other cleavage-inducing agent such as chemical agent or light. Exemplary conditions are set forth below.

A "biological sample" or "sample" encompasses a variety of sample types, e.g., obtained from an individual, and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polypeptides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, blood fractions such as plasma and serum, and the like. In some cases, a biological sample includes cells or cell fractions.

The phrase "site of N-glycosylation", as used herein, refers to any site on a protein where N-glycosylation may occur (i.e., N-glycosites). In some aspects, N-glycosylation occurs at a site on a protein where a sugar molecule attaches (i.e., binds) to a nitrogen atom in an amino acid residue of the protein. For example N-glycosylation may be where Asn residues in a protein are attached to a carbohydrate through a nitrogen atom (i.e., N-glycosites). N-glycosylation may occur, for example, on a eukaryotic protein (i.e., a protein of a eukaryotic cell). Similarly, "site of O-glycosylation" refers to any site on a protein where O-glycosylation may occur, such as a site where a sugar molecule attaches to an oxygen atom in an amino acid residue of the protein.

As referred to herein, the term "eukaryotic cell" is used in its conventional sense to refer to one or more cells obtained from multi-cell organisms such animals, plants, fungi and yeast. As such, eukaryotic cells may include but are not limited to those obtained from yeast, fungi, plants, and animals including humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In certain embodiments, eukaryotic cells include those obtained from a human being.

As used herein, the term "substituted" refers to a group in which one or more atoms of the group are each independently replaced with a substituent(s), where the atom being replaced may be a hydrogen or non-hydrogen atom (e.g., a carbon or a heteroatom). A group that is "substituted" can have 1 or more substituents, where the substitutents are independently selected from the group consisting of acyl, acylamino, acyloxy, alkoxy, alkoxycarbonyl, alkoxycarbonylamino, alkyl, trihaloalkyl, alkenyl, alkynyl, amino, amido, imino, aminocarbonyl, aminocarbonylamino, aminocarbonyloxy, aryl, aryloxy, azido, diazo, carboxyl, carbonyl, cyano, isocyanate, isothiocyanate, cycloalkyl, guanidyl, halogen, heterocyclyl, heterocyclyloxy, hydroxyl, keto, nitro, nitroso, oxo, thio, thioether, thioalkoxy, thioaryloxy, thioketo, thiol, sulfonate, sulfinate, phosphinate, phosphonate, alkyl-S(O)—, aryl-S(O)—, alkyl-S(O)$_2$— and aryl-S(O)$_2$.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

The compounds of the invention may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)- isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, methods and materials of interest are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an isotopically-labelled peptide" includes a plurality of such peptides and reference to "the chemoselective tag" includes reference to one or more chemoselective tags and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides methods for producing an isotopically-labelled peptide. Aspects of the method include: contacting a sample including a metabolically tagged protein with a cleavable probe under conditions sufficient to produce a probe-protein conjugate; separating the probe-protein conjugate from the sample; digesting the probe-protein conjugate to produce a probe-peptide conjugate; and cleaving a cleavable linker of the probe to release the isotopically labelled peptide. In some instances, the method further includes: identifying a predetermined isotopic pattern in a mass spectrum; determining an amino acid sequence of the isotopically labelled peptide; and identifying the site of glycosylation on the protein based on the determined amino acid sequence. Also provided are compositions, such as cleavable probes and kits for practicing the subject methods.

Cleavable probes that find use in the subject methods and compositions are now described in more detail, followed by further details of the methods of using the same.

Cleavable Probes

Cleavable probes that find use in the subject compositions and methods may include an affinity tag linked to an isotopic label via a cleavable linker, and a chemoselective tag. The chemoselective tag may be attached to the probe at any convenient position. In some cases, the chemoselective tag is linked directly or indirectly to the isotopic label or to the cleavable linker. Any convenient configurations of the affinity tag, cleavable linker, chemoselective tag, isotopic label and one or more optional linkers (e.g., branched or liner bivalent linkers connecting any two or more components of the probe) may be utilized in the subject cleavable probes.

Chemoselective Tags

Any convenient chemoselective tags may be utilized in the subject probes. As used herein, the terms "chemoselective tag", "chemoselective group" and "chemoselective functional group" are used to refer to moieties that include chemoselective reactive groups that are capable of selectively reacting with a compatible chemoselective functional group to form a covalent bond. Chemoselective functional groups of interest include, but are not limited to, any convenient pairs of compatible reactive functional groups such as thiols and maleimides, thiols and iodoacetamides, aldehydes or ketones and alkoxyamines, or aldehydes or ketones and hydrazides; pairs of groups that can react with one another via Click chemistry, e.g., azide and alkyne groups (e.g., cyclooctyne groups); pairs of groups that can react with one another via Staudinger ligation chemistry such as azides and phosphines. In some embodiments of the probe, Z is a chemoselective tag that includes a group selected from an alkyne, an azide, a phosphine (e.g., a substituted triphenyl phosphine), a thiol, a maleimide or iodoacetyl, an aldehyde, a hydrazide and an alkoxyamine. In certain instances, Z includes an azide. In some instances Z includes an alkyne.

In certain embodiments, Z is an alkyne. Any convenient alkyne-containing groups may be utilized in the subject probes. Alkyne-containing groups of interest include, but are not limited to, acetylene, a cyclooctyne, such as one of the cyclooctyne groups described by Bertozzi et al. in U.S. Pat. Nos. 7,807,619, and 8,703,936, the disclosures of which are herein incorporated by reference in their entirety. In certain embodiments, Z is an alkyne tag. In certain embodiments, Z includes an ethyne. In certain embodiments, Z includes a cyclooctyne.

Affinity Tags

Any convenient affinity tags may be utilized in the subject probes. As used herein the terms "affinity agent" and "affinity tag" are used interchangeably and refer to an agent that binds a complementary molecule through an interaction that is sufficient to permit the agent to extract and concentrate the molecule from a homogeneous mixture of different molecules. The binding interaction may be mediated by an affinity region of the capture agent. The term may refer to a member of a specific binding pair, i.e. two molecules where one of the molecules specifically binds to the other molecule. Thus, the term "affinity agent" refers to a molecule or a multi-molecular complex which can specifically bind a complementary molecule, e.g., specifically bind a complementary molecule with a dissociation constant ($K_D$) of $10^{-6}$ or less without binding to other targets, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less.

The term "complementary" references a property of specific binding between pairs of specific binding moieties. Specific binding moieties are complementary if they specifically bind to each other. A pair of specific binding moieties that are each polynucleotides may be complementary based on their sequence complementarity. As used herein, polynucleotides are complementary if they bind to each other in a hybridization assay under stringent conditions. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. Additional examples of specific binding pairs which may be considered complementary include antibody-antigen binding pairs, receptor-ligand binding pairs, nucleic acid aptamer-protein binding pairs and the like.

The complementary member of the affinity tag may be immobilized (e.g., to a chromatography support, a bead or a planar surface) to produce an affinity chromatography support that specifically binds the affinity tag. Tagging a compound of interest with an affinity tag allows the compound to be separated from a mixture of untagged compounds by affinity, e.g., using affinity chromatography. Examples of specific binding pairs include biotin and streptavidin (or avidin), complementary nucleic acids of a duplex and antigen and antibody, although binding pairs, e.g., nucleic acid hybrids, polyhistidine and nickel are also envisioned. The specific binding pairs may include analogs, derivatives and fragments of the original specific binding members. In some instances, affinity tags may be a chemoselective group (e.g., as described herein), which specifically binds via a covalent bond to a complementary functional group of the other molecule. In certain instances, the affinity tag is a member of a specific binding pair that specifically binds non-covalently.

In some embodiments of the probe, A is a biotin moiety. As used herein, the term "biotin moiety" refers to an affinity tag that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$ M. A biotin moiety may also include a linker, e.g., -LC-biotin, -LC-LC-Biotin, -SLC-Biotin or -PEG$_n$-Biotin where n is 3-12 (commercially available from Pierce Biotechnology).

The affinity tag allows tagged (e.g., labelled) polypeptide products to be separated from a mixture of untagged polypeptides by affinity, e.g., using affinity support, e.g., a chromatography column or magnetic beads. Affinity capture components of interest include, but are not limited to, a ligand and a receptor (e.g., biotin and avidin), an antibody and an antigen, complementary polynucleotides, an aptamer and a small molecule, a polyhistidine tag and nickel, and a reactive group such as a thiol, which can undergo a Michael addition with an electrophilic group, or form a disulfide bond with another thiol group. The specific binding pairs may include analogs, derivatives and fragments of the original specific binding members. For example, an antibody directed to a protein antigen may also recognize peptide fragments, chemically synthesized, labeled protein, derivatized protein, etc. so long as an epitope is present. In certain embodiments, the affinity tag includes biotin. Other affinity tags or reactive groups that may be used include, but are not limited to: polyhistidine (e.g., 4 to 14, such as 6 to 10 residues), benzophenone, a sulfhydryl group, an aryl azide and an azirine.

In some embodiments, the affinity tag includes a biotin moiety, such as biotin, desthiobiotin, oxybiotin, 2'-iminobiotin, diaminobiotin, biotin sulfoxide, biocytin, etc. The biotin moiety is capable of specifically binding with high affinity to a support e.g., a chromatography support that contains immobilized avidin, neutravidin or streptavidin. In some cases, a monomeric avidin support may be used to specifically bind biotinylated crosslinked polypeptides with moderate affinity thereby allowing bound crosslinked polypeptides to be later eluted competitively (e.g., with a 2 mM biotin solution or using a highly organic elution solution, e.g., 70% acetonitrile) after non-biotinylated polypeptides have been washed away.

Cleavable Linkers and Optional Linkers

Any convenient cleavable linkers may be utilized in the subject cleavable probes to link the affinity tag to one or more other components. In some embodiments of the probe, the cleavable linker L is described by the formula:

$-L^1-X-L^2-$ where $L^1$ and $L^2$ are optional linkers and X is a cleavable group.

As used herein, the term "linker", "linking group" and "linkage" are used interchangeably to refer to a linking moiety that connects two groups and has a backbone of any suitable length. In some cases, the linker has a backbone of 20 atoms or less in length. A linker or linkage may be a covalent bond that connects two groups or a chain of any convenient length (e.g., between 1 and 20 atoms in length), for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol), modified polyethylene glycol; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

Any convenient cleavable groups may be utilized to provide for cleavage of the linker upon application of a suitable stimulus. Cleavable linkers that include cleavable groups of interest, include but are not limited to those cleavable linkers as described by Szychowski et al. (*J Am Chem Soc* 2010, 132, 18351), Olejnik et al. (Methods in Enzymology 1998 291:135-154), and further described in U.S. Pat. No. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); Sanford et al. (Chem. Mater. 1998 10:1510-20), and linkers such as electrophilically cleavable linkers, nucleophilically cleavable linkers, photocleavable linkers, metal cleavable linkers, electrolytically-cleavable, enzymatically cleavable linkers, linkers that are cleavable under reductive or oxidative conditions (e.g., a disulfide linker or a diazobenzene linker) and linkers that are cleavable using an acidic reagent (see e.g., Fauq et al., Bioconjugate Chem. 2006; 17:248-254) or a basic reagent. In some cases, the cleavable linker includes a chemically cleavable group (e.g., a fluoride cleavable group), a photocleavable group or an enzymatically cleavable group.

Any convenient enzymatically cleavable groups may be utilized in the cleavable linkers. For example, the enzymatically cleavable group can be a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO: 1) or Pro-Leu/Gln-Gly-Met-Thr (SEQ ID NO:2). Another example of a protease cleavage site is a plasminogen activator cleavage site, e.g., a uPA or a tissue plasminogen activator (tPA) cleavage site. Specific examples of cleavage sequences of uPA and tPA include sequences including Val-Gly-Arg. Another example is a thrombin cleavage site, e.g., CGLVPAGSGP (SEQ ID NO:3). Additional suitable linkers including protease cleavage sites include linkers including one or more of the following amino acid sequences: 1) SLLKSRMVPNFN (SEQ ID NO:4) or SLLIARRMPNFN (SEQ ID NO:5), cleaved by cathepsin B; SKLVQASASGVN (SEQ ID NO:6) or SSYLKASDAPDN (SEQ ID NO:7), cleaved by an Epstein-Barr virus protease; RPKPQQFFGLMN (SEQ ID NO:8) cleaved by MMP-3 (stromelysin); SLRPLAL-WRSFN (SEQ ID NO:9) cleaved by MMP-7 (matrilysin); SPQGIAGQRNFN (SEQ ID NO: 10) cleaved by MMP-9; DVDERDVRGFASFL (SEQ ID NO: 11) cleaved by a thermolysin-like MMP; SLPLGLWAPNFN (SEQ ID NO: 12) cleaved by matrix metalloproteinase 2 (MMP-2); SLLI-FRSWANFN (SEQ ID NO:13) cleaved by cathespin L; SGVVIATVIVIT (SEQ ID NO:14) cleaved by cathepsin D; SLGPQGIWGQFN (SEQ ID NO:15) cleaved by matrix metalloproteinase 1 (MMP-1); KKSPGRVVGGSV (SEQ ID NO:16) cleaved by urokinase-type plasminogen activator; PQGLLGAPGILG (SEQ ID NO: 17) cleaved by membrane type 1 matrixmetalloproteinase (MT-MMP); HGPEGLRVGFYESDVMGRGHARLVHVEEPHT (SEQ ID NO:18) cleaved by stromelysin 3 (or MMP-11), thermolysin, fibroblast collagenase and stromelysin-1; GPQGLAGQRGIV (SEQ ID NO:19) cleaved by matrix metalloproteinase 13 (collagenase-3); GGSGQRGRKALE (SEQ ID NO:20) cleaved by tissue-type plasminogen activator (tPA); SLSALLSSDIFN (SEQ ID NO:21) cleaved by human prostate-specific antigen; SLPRFKIIGGFN (SEQ ID NO:22) cleaved by kallikrein (hK3); SLLGIAVPGNFN (SEQ ID NO:23) cleaved by neutrophil elastase; and FFKNIVTPRTPP (SEQ ID NO:24) cleaved by calpain (calcium activated neutral protease).

Cleavable linkers useful for connecting to the affinity tag may include photo-sensitive groups comprising bonds that break upon exposure to light of a certain wavelength. Suitable photocleavable linkers for use in the subject cleavable probes include, but are not limited to, ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157). For example, a 1-(2-nitrophenyl)ethyl-based photocleavable linker (Ambergen) can be efficiently cleaved using near-UV light, e.g., in >90% yield in 5-10 minutes using a 365 nm peak lamp at 1-5 mW/cm².

Any convenient chemically cleavable groups may be utilized in the cleavable linkers. In some cases the cleavable group is a silane, such that L is a cleavable silane linker (e.g., as described herein). In certain embodiments of the linker, the cleavable group (X) is —O—Si(R)$_2$—O—, where each R is independently selected from hydrogen, an aryl, a substituted aryl, an alkyl and a substituted alkyl. In certain embodiments, the cleavable linker L is described by the formula -(PEG)$_n$-NH—(CH$_2$)$_m$—C(CH$_3$)$_2$—O—Si(R)$_2$—O—, where n and m are each independently 0 or any suitable integer (e.g., n and m are each 0-20), and each R is independently selected from hydrogen, an aryl, a substituted aryl, an alkyl and a substituted alkyl. In some embodiments, the cleavable linker is a dialkoxydiarylsilane linker, such as a dialkoxydiphenylsilane (DADPS) linker. In certain embodiments, the linker is an acid-sensitive DADPS linker that may be cleaved by application of an acid cleavage reagent (e.g., 10% formic acid).

Isotopic Label

Any convenient isotopic labels may be utilized in the subject cleavable probes. Isotopic labels of interest include, but are not limited to, groups described by Bertozzi et al. in US Publication No. 2014/0199716, groups that find us in isotope-coded affinity tags (ICAT) as described by Gygi et al. ((1999) Quantitative analysis of complex protein mixtures using isotope-coded affinity tags. Nat Biotechnol. 17, 994-9; and (2002) Proteome analysis of low-abundance proteins using multidimensional chromatography and isotope-coded affinity tags. J Proteome Res. 1, 47-54), the disclosures of which are herein incorporated by reference in their entirety.

Figure 11:
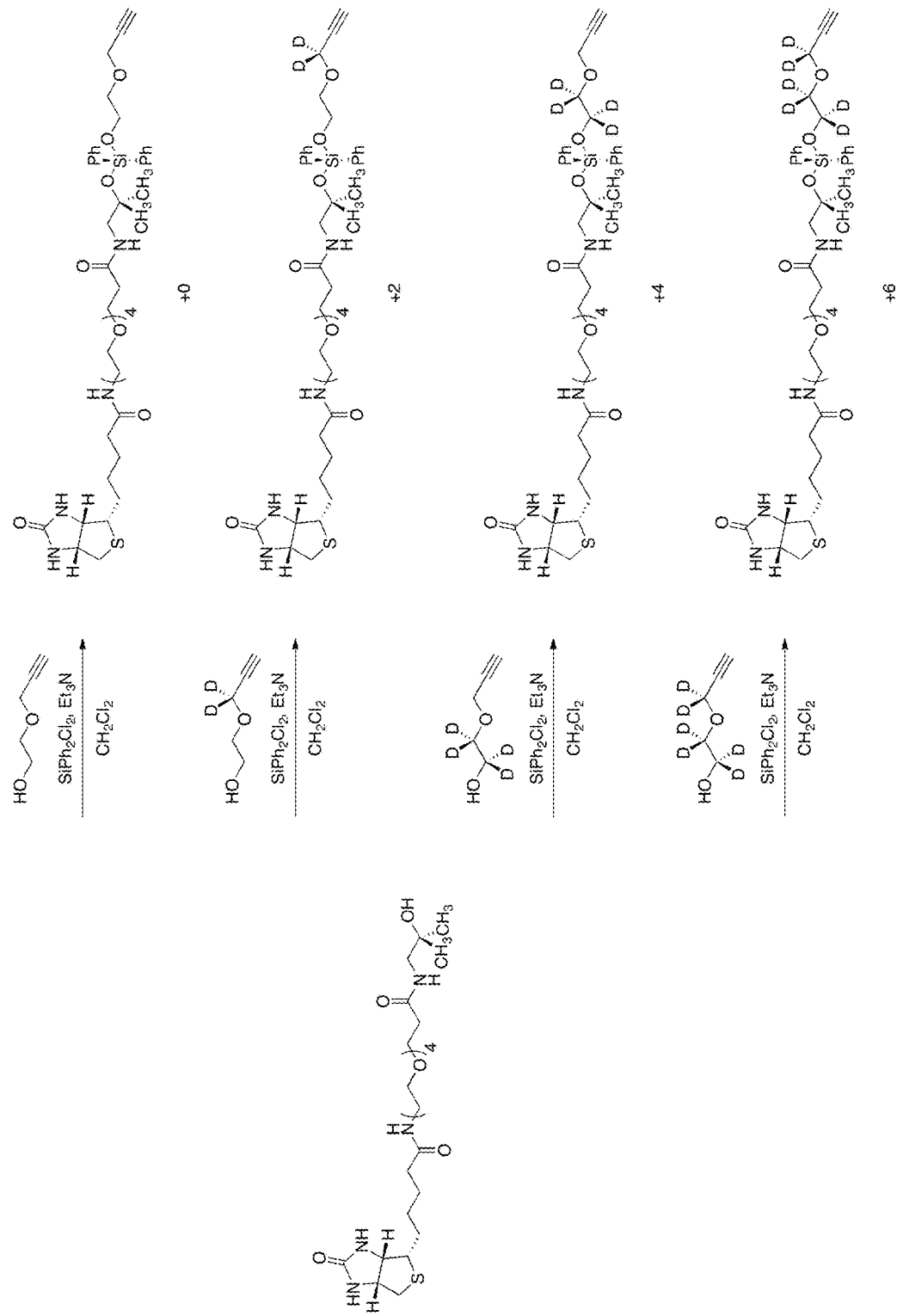
FIG. 11 illustrates the preparation of cleavable probes which include deuterium isotopic labels. Mixtures of m+0, m+2, m+4 and m+6 probes may be utilized to provide for a desired IsoTaG signature.

As used herein, the terms "isotopic label" refers to a chemical composition that can be used for isotopic labeling and is, in some instances, referred to as an "isomix". In some embodiments, an isotopic labeling composition or an isotopically recoded composition is a composition that imparts sufficient perturbation to a peptide's isotopic envelope such that a successful targeted LC-MS/MS analysis may be conducted. An isotopic labeling composition can include 2 or more isotopic labels, 3 or more isotopic labels, 4 or more isotopic labels, or 5 or more isotopic labels. In some cases, an isotopic labeling composition can include 2, 3, 4, 5, or more isotopic labels. In some instances, an isotopic label refers to a mixture of components, where each component has the same general formula, but is labelled with different atomic isotopes. For example, as depicted in FIG. 11, the isotopic label may include a mixture of two or more components (e.g., 2, 3 or 4 or more components) where each component has independently a number of hydrogen atoms substituted for deuterium atoms selected from 0, 2, 4 and 6 substituted atoms.

In some versions of the disclosed methods, isotopic labeling compositions include particular stoichiometric ratios of components thereof (e.g., isotopic labels). For example, isotopic labeling compositions composed of two or more components (e.g., isotopic labels) may include a stoichiometric ratio (e.g., molar ratio) of components of, for example, 1:1; 1:2; 1:3; 1:4; 1:5; 1:6; 1:7; 1:8; 1:9; 1:10; 1:11; 1:12; 1:13; 1:14; 1:15; 1:16; 1:17; 1:18; 1:19; or 1:20; etc. In various aspects, stoichiometric ratios of components of isotopic labeling compositions are measurable by a process (e.g., LC-MS/MS). In some embodiments, isotopic labeling compositions composed of three or more components (e.g., isotopic labels) include a stoichiometric ratio of those components of, for example, 1:1:1; 1:2:1; 1:3:1; 1:4:1; 1:5:1; 1:6:1; 1:7:1; 1:8:1; 1:9:1; 1:10:1; 1:2:2; 1:3:2; 1:4:2; 1:5:2; 1:6:2; 1:7:2; 1:8:2; 1:9:2; or 1:10:2; 1:2:3; 1:3:3; 1:4:3; 1:5:3; 1:6:3; 1:7:3; 1:8:3; 1:9:3; or 1:10:3; etc.

As used herein, the phrase "isotopic labeling" or "isotopically recoding" refers to one or more techniques or processes for tracking the passage of an isotope or atom with a variation through a metabolic pathway, cell or reaction. In some aspects, isotopic labeling includes replacing specific atoms of a reactant with their isotopes. In some aspects, isotopic labeling includes producing one or more isotopic labels. In some instances, "isotopic label" means a molecule (e.g., a probe molecule) having at least one atom that has been replaced by an atom enriched in a specific isotope of that atom that differs from the natural abundance of isotopes of that atom (e.g., a detectable isotope). Isotopic labeling may also include detecting the presence and/or absence of one or more isotopic labels in a sample. In some embodiments, isotopic labels do not contain any halogen (e.g., bromine or chlorine) atoms.

In some instances, an isotopic signature includes a detectable characteristic of an isotopic label incorporated into a subject probe. In some aspects, an isotopic signature does not include using one or more halogenated (e.g., dibrominated or dichlorinated) tags. In some instances, an isotopic signature includes a detectable stoichiometric ratio of two or more isotopic labels. In some embodiments, an isotopic signature includes a detectable stoichiometric ratio of two or more isotopic labels that is unnatural. In particular embodiments, an isotopic signature is detectable by LC-MS/MS. In some embodiments of the probe, the isotopic label (M) includes two or more halogen atoms (e.g., bromine or chlorine atoms). Bromine atoms may find use in the subject isotopic labels because bromine provides for a 1:1 mixture of $^{79}$Br and $^{81}$Br atomic isotopes that are not usually present in analytes of interest, and therefore may be readily distinguished using mass spectroscopy. Any convenient bromine containing groups may be utilized in an isotopic label in the subject probes to provide for a distinct isotope signature in mass spectroscopic analysis. In some instances, the isotopic label includes 2 bromine atoms and provides for a particular distinct isotope signature in mass spectroscopic analysis (e.g., as described herein).

In some embodiments of the probe, the isotopic label M is a brominated alkenyl or alkylalkenyl, such as a dibrominated alkenyl or alkylalkenyl, where the alkenyl or alkylalkenyl may optionally be further substituted. In some embodiments of the probe, the isotopic label M is described by the formula:

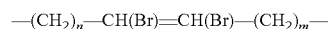
—(CH$_2$)$_n$—CH(Br)=CH(Br)—(CH$_2$)$_m$— wherein n and m are each independently 0-6. In certain embodiments, n and m are each 1. In certain embodiments, n+m is 1. In certain embodiments, n+m is 2. In certain embodiments, n+m is 3. In certain embodiments, n+m is 4. In certain embodiments, n+m is 5. In certain embodiments, n+m is 6.

In some embodiments of the probe, the isotopic label M is a mixture of components that each independently include 0, 2, 4 and/or 6 deuterium atoms and provide for a desired mass signature, such as a m/m+2/m+4 signature with a 1:2:1 ratio of peak intensities. In some instances, the isotopic label M is described by the formula (IV):

—CR$^1_2$CR$^2_2$—X—CR$^3_2$— (IV)

where X is O, S or NR where R is H, an alkyl, a substituted alkyl, an aryl or a substituted aryl;

each $R^1$ is H or D;
each $R^2$ is H or D; and
each $R^3$ is H or D.

In certain embodiments of formula (IV), X is O. In certain embodiments of formula (IV), each $R^1$ is D. In certain embodiments of formula (IV), each $R^2$ is D. In certain embodiments of formula (IV), each $R^3$ is D. In certain embodiments of formula (IV), each $R^1$ is H, each $R^2$ is H and each $R^3$ is H. In certain embodiments of formula (IV), each $R^1$ is H, each $R^2$ is H and each $R^3$ is D. In certain embodiments of formula (IV), each $R^1$ is D, each $R^2$ is D and each $R^3$ is H. In certain embodiments of formula (IV), each $R^1$ is D, each $R^2$ is D and each $R^3$ is D. It is understood that the isotopic label of formula (IV), may include a mixture of components, where each component may be described by formula (IV) but include a different number of deuterium atoms (D). In some cases of formula (IV), the isotopic label includes a mixture of components (e.g., 2, 3, 4 or more components), where each component independently comprises 0, 2, 4 or 6 deuterium atoms.

Cleavable Probes

In some instances, the cleavable probe has the formula A-(L-Z)-M where M is connected to (L-Z) at any convenient position, where A is an affinity tag, L is a cleavable linker, M is an isotopic label and Z is a chemoselective tag; and each of the components are linked as shown via optional non-cleavable linkers. and In some embodiments, the cleavable probe is described by Formula (I):

    A-L-(M-Z)    (I)

wherein: A is an affinity tag; L is a cleavable linker; M is an isotopic label; and Z is a chemoselective tag, where A, L, M and Z are covalently connected to each other directly or via optional linkers, where the optional linkers may be branched linkers or linear bivalent linkers. In some embodiments of formula (I): A is a biotin moiety; L is -(PEG)$_n$-NH—(CH$_2$)$_m$—C(CH$_3$)$_2$—O—Si(R)$_2$—O—; M is —(CH$_2$)$_p$—CH(Br)=CH(Br)—(CH$_2$)$_q$—; and Z is an alkyne-containing group, wherein n and m are each independently 0-20 and p and q are each independently 0 or any suitable integer (e.g., p and q are independently 0-6).

In some embodiments, the cleavable probe is described by Formula (II):

    A-L-M-Z    (II)

wherein: A, L, M and Z are as defined in formula (I). In some embodiments of formula (II): A is a biotin moiety; L is -(PEG)$_n$—NH—(CH$_2$)$_m$—C(CH$_3$)$_2$—O—Si(R)$_2$—O—; M is —(CH$_2$)$_p$—CH(Br)=CH(Br)—(CH$_2$)$_q$—; and Z is an alkyne-containing group, wherein n and m are each independently 0-20 and p and q are each independently 0 or any suitable integer (e.g., p and q are independently 0-6).

In some embodiments, the cleavable probe is described by Formula (III):

    A-L-Z-M    (III)

wherein: A, L, M and Z are as defined in formula (I).

In some embodiments of the probe, the probe has the formula A-L-M-Z, where: A is a biotin moiety; L is -(PEG)$_n$—NH—(CH$_2$)$_m$—C(CH$_3$)$_2$—O—Si(R)$_2$—O—; M is —(CH$_2$)$_p$—CH(Br)=CH(Br)—(CH$_2$)$_q$—; and Z is an alkyne-containing group, wherein n and m are each independently 0-20 and p and q are each independently 0 or any suitable integer (e.g., p and q are independently 0-6).

In certain embodiments of the probe, M is described by the formula (IV):

    —CR$^1$$_2$CR$^2$$_2$—X—CR$^3$$_2$—    (IV)

where X is O, S or NR where R is H, an alkyl, a substituted alkyl, an aryl or a substituted aryl; each $R^1$ is H or D; each $R^2$ is H or D; and each $R^3$ is H or D; and Z is an alkyne, such as ethyne (e.g., Z is —CCH).

Methods

As summarized above, the present disclosure includes methods for producing an isotopically-labelled peptide. In some embodiments, the method includes: contacting a sample including a metabolically tagged protein with a cleavable probe under conditions sufficient to produce a probe-protein conjugate, wherein the cleavable probe is described by Formula (I):

    A-L-(M-Z)    (I)

wherein A is an affinity tag, L is a cleavable linker, M is an isotopic label and Z is a chemoselective tag capable of cross-linking the metabolically tagged protein;
    separating the probe-protein conjugate from the sample;
    digesting the probe-protein conjugate to produce a probe-peptide conjugate; and
    cleaving the cleavable linker to release the isotopically labelled peptide.

Any convenient method may be used to contact the sample with a cleavable probe. The cleavable probe may include a chemoselective tag capable of labelling a tagged protein (e.g., a metabolically tagged protein) in the sample, where the tagged protein includes a compatible functional group. In some instances, the sample is contacted with the subject composition under conditions in which the chemoselective tag cross-links with a complementary functional group of the tagged protein, if present in the sample, to produce a probe-protein conjugate. The term "contacting" is used herein in its conventional sense to refer to placing two or more aspects in proximity or providing an interaction or communication between two or more aspects. For example, contacting may mean exposing (e.g., incubating with and/or allowing direct physical contact between) one aspect (e.g., an cleavable probe) to another aspect (a cell). Contacting may also mean, for example, allowing one aspect to integrate with and/or penetrate and/or chemically react with another aspect.

Any convenient method may be used to separate the probe conjugate (e.g., probe-protein conjugate or probe-peptide conjugate, as described herein) from the sample. Separation of any affinity tag containing moiety (e.g., the probe or probe conjugate) may be achieved via specific binding of the affinity tag to a complementary specific binding member that provides for separation of the resulting complex (e.g., a support immobilized specific binding member complementary with the affinity tag). The separation step may be performed at any convenient time during the method prior to cleaving the cleavable linker of the probe. In some cases, the affinity separation is performed prior to digestion of the protein. In certain cases, the affinity separation is performed after digestion of the protein into peptides, such that probe-peptide conjugates may be captured by an immobilized specific binding member. For specific binding of the affinity tag with the immobilized specific binding member, an appropriate solution may be used that maintains the structure and/or binding activity of the affinity tag and the specific binding members. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include, but are not limited to, HEPES, phosphate buffers, lactate buffers, etc. Various media are commercially available and may be used according to the nature of the sample, including dMEM, HBSS, dPBS, RPMI, Iscove's medium, etc., frequently supplemented with fetal calf serum or human platelet lysate. The final components of the solution may be selected depending on the components of the sample which are included. The sample may include a heterogeneous cell population from which target analytes are isolated.

The temperature at which specific binding of the affinity agent with the immobilized specific binding member takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity or stability of the target analyte and/or other components of the sample. In certain instances, the temperature is 25° C., 30° C., 35° C. or 37° C. In certain cases, the affinity tag or immobilized specific binding member is an antibody or fragment thereof and the temperature at which specific binding takes place is room temperature (e.g., 25° C., 30° C., 35° C. or 37° C.). Any convenient incubation time for specific binding may be selected to allow for the formation of a desirable amount of capture of the probe-protein conjugate, and in some instances, may be 1 minute (min) or more, such as 2 min or more, 10 min or more, 30 min or more, 1 hour or more, 2 hours or more, or even 6 hours or more.

The subject methods may further include one or more optional washing steps to remove unbound material of the sample from a support bound complex including the probe-protein conjugate. Any convenient washing methods may be used, e.g., washing the immobilized support with a biocompatible buffer which preserves the specific binding interactions of the complex. Separation and optional washing of unbound material of the sample from the support provides for an enriched population of target probe-protein conjugates where undesired cells and/or material may be removed.

As described above, aspects of the method include digesting the protein of the probe-protein conjugate to produce a probe-peptide conjugate. The digestion step may be performed at any convenient time during the method to digest the probe-protein conjugate into a probe-peptide conjugate. In certain cases, the method does not include digestion of the target protein. In some cases, digestion is performed after separation of the probe-protein conjugate from the sample. In certain cases, the digestion step is performed before the sample separation step, where a subsequent affinity separation may be performed to separate the resulting probe-peptide conjugate from the resulting mixture. Digestion of the conjugate maybe achieved using any convenient enzyme (s). One or more digestion enzymes for use in the subject methods may be selected depending on a variety of factors such as enzyme specificity, target protein sequence, target protein modifications, complexity of sample, mass spectroscopic analytical method, etc., as desired to provide for cleavage of the protein of the conjugate at particular locations, thereby producing a probe-peptide conjugate of interest. Enzymes of interest include, but are not limited to, trypsin.

As described above, aspects of the method include cleaving the cleavable linker of the probe conjugate (e.g., a probe-protein or probe-peptide conjugate) from the reporter complex by cleavage (e.g., chemical, enzymatic or photo-cleavage). Cleavage of the cleavable group in the cleavable probe results in release of an isotopically labelled protein or peptide fragment thereof from the immobilized affinity tag complex. As described herein, release of an enriched population of isotopically labelled analyte (e.g., isotopically labelled protein or peptide fragment thereof) provides for a desirable and facile mass spectroscopic analysis (e.g., as described herein).

A cleavable group may be included in the cleavable probe (and thus conjugates thereof) at any convenient location to provide for selective cleavage of the isotopically labelled fragment from the probe conjugate upon application of a stimulus. Application of a stimulus may include contacting the reporter complex with an enzyme or a chemical agent, or irradiation with light (e.g., of a particular wavelength).

Tagged Proteins

Any convenient samples may be utilized in the subject methods. The sample may include a tagged protein. Any convenient tagged protein may be target for labelling using the subject methods. Tagged proteins of interest include proteins that have a chemoselective functional group at one or more sites of the protein which provide for labelling of the protein with the subject cleavable probe. Tagged proteins may be produced synthetically ex vivo (e.g., using any convenient protein reactive tag or enzymatic labelling reaction), or may be produced in vivo, e.g., metabolically tagged in a cell. Any convenient methods of metabolic labelling may be adapted for use in the subject methods to incorporate a chemoselective functional group (e.g., an azide) at any convenient site target protein. In some embodiments of the method, the sample is obtained from a eukaryotic cell including the metabolically tagged glycosylated protein. In some embodiments of the method, the metabolically tagged protein is a metabolically tagged glycosylated protein and the isotopically labelled peptide is an isotopically labelled glycopeptide.

As such, in certain embodiments, the method further includes contacting the cell with a tagged sugar under conditions sufficient to produce the metabolically tagged glycosylated protein. In certain cases, the tagged sugar is an azide tagged sugar, such as N-azidoacetylgalactosamine, acetylated (Ac4GalNAz), N-azidoacetylglucosamine, acetylated (Ac4GlcNAz) or N-azidoacetylmannosamine, acetylated (Ac4ManNAz). In certain instances, the tagged sugar includes an isotopic label (e.g., as described herein). In some embodiments, the tagged sugar includes an isotopic label that provides for a mass shift of 2 or more, such as 5 or more or even 10 or more, e.g., a mass shift of m+2, m+3, m+4, m+5, m+6, m+7, m+8, m+9 or m+10, as compared to a tagged sugar that does not include an isotopic label. In certain embodiments, the tagged sugar is $Ac_4GAlNAz$-3, e.g., an $Ac_4GAlNAz$ sugar that includes isotopic label which shifts its mass by m+3, such as an $Ac_4GAlNAz$ sugar that includes three deuterium substituents. In some embodiments of the method, the metabolically tagged protein is metabolically tagged with two or more tagged sugars, one of which includes a chemoselective tag, and another of which includes an isotopic label.

In some embodiments of the method, the metabolically tagged protein includes a chemoselective tag (e.g., as described herein). Any convenient chemoselective tags may be incorporated into a metabolically tagged glycosylated protein of interest. In some instances, the chemoselective tag is an azide.

In certain versions of the disclosed methods, the method further includes contacting the cell with a tagged sugar under conditions sufficient to produce a metabolically tagged glycosylated protein. In some instances, contacting the cell (e.g., eukaryotic cell) with an isotopic labeling composition includes incubating the cell with a composition (i.e., a modified sugar) that includes a chemoselective functional group (e.g., as described herein, such as an azide). As used herein, the term "incubating" means exposing an aspect (e.g., one or more cells) to a set of conditions (e.g., environmental conditions such as temperature and/or pressure) and/or placing an aspect in a specific physical location (e.g., a location where the aspect is exposed to one or more chemical compositions) for a length of time in order to produce a desired result (e.g., integration of at least one modified sugar into a biosynthetic pathway).

In some embodiments of the disclosed methods, contacting the eukaryotic cell with an isotopic labeling composition includes metabolically embedding a chemoselective functional group into one or more molecules (e.g., glycans). By "metabolically embedding", as used herein, is meant inserting an aspect (e.g., one or more tagged sugars) into one or more metabolic processes (e.g., metabolic processes occurring within a eukaryotic cell). In some aspects, metabolic processes are associated with a glycan biosynthetic pathway (e.g., the gna1Δ yeast hexosamine biosynthetic pathway). As used herein, the term "glycan" refers to a polysaccharide or oligosaccharide.

Any convenient metabolically tagged proteins may be utilized and/or targeted in the subject methods. In some cases, the metabolically tagged protein is a metabolically tagged glycosylated protein and the isotopically labelled peptide is an isotopically labelled glycopeptide. In certain instances, the sample is obtained from a eukaryotic cell including the metabolically tagged glycosylated protein.

Mass Spectroscopic Analysis

Any convenient methods, probe components and reagents may be utilized in the subject methods in conjunction with providing for mass spectroscopic analysis of the products of the subject methods. Methods and materials of interest include those described by Bertozzi et al. in US Publication No. 2014/0199716, the disclosure of which is herein incorporated by reference in its entirety. In some embodiments, the method further includes: identifying a predetermined isotopic pattern in a mass spectrum; determining an amino acid sequence of the isotopically labelled peptide; and identifying the site of glycosylation on the protein based on the determined amino acid sequence.

In some embodiments of the method, the identifying step includes identifying isotopically labeled peptides by full scan mass spectrometry prior to tandem MS analysis.

Various embodiments of the methods include identifying a predetermined isotopic pattern in a mass spectrum at one or more retention times (i.e., retention times of a liquid chromatography process). A predetermined isotopic pattern may correspond, for example, to any of the stoichiometric ratios of the isotopic labeling compositions listed above. In certain variations of the methods, identifying a predetermined isotopic pattern includes identifying a peak intensity ratio in the mass spectrum. For example, in some embodiments, identifying a predetermined isotopic pattern includes identifying a 1:2:1 peak intensity ratio in the mass spectrum. In some aspects, an identifiable peak intensity ratio in a mass spectrum may correspond to a stoichiometric ratio of two or more isotopic labels.

Particular embodiments of the disclosed methods include determining an amino acid sequence of a peptide present at one or more retention times (i.e., retention times of a liquid chromatography process). Determining an amino acid sequence of a peptide may be achieved by any of the methods described herein or by other suitable methods. In various embodiments of the methods, retention times corresponding to amino acid sequences that are determined are selected based on the identification of a predetermined isotopic pattern using mass spectrometry.

Select aspects of the methods include identifying a site of N-glycosylation or O-glycosylation on a protein based on an amino acid sequence (e.g., a determined amino acid sequence) of a peptide present at one or more retention times (i.e., retention times of a liquid chromatography process).

In some embodiments of the disclosed methods include generating an inclusion list of peptides having a mass spectrum that contains a predetermined isotopic pattern. In some embodiments, a predetermined isotopic pattern is an isotopic pattern corresponding to any of the stoichiometric ratios of the isotopic labeling compositions listed above. As noted above, the inclusion list is a compilation or listing of one or more of 1) m/z values from a mass spectrometer, 2) m/z and retention time window and 3) m/z and retention time window and ion abundance which have been identified as having mass spectra containing a predetermined isotopic pattern as described above. The inclusion list may include any number of peptides, depending on the biological sample and may include 1 or more peptides, such as 20 or more peptides, such as 50 or more peptides, such as 100 or more peptides, such as 250 or more peptides, such as 500 or more peptides, such as 1000 or more peptides, and including 2500 or more peptides. As desired, one or more of the peptides on the inclusion list may be further subjected to determination of amino acid sequence. As noted above, determining an amino acid sequence of a peptide (e.g., one or more peptides on an inclusion list) may be achieved by any of the methods described herein or by other suitable methods.

Methods for employing mass spectrometry for amino acid sequencing is discussed in greater detail in, e.g., Syka, J. E. P., Coon, J. J., Schroeder, M. J., Shabanowitz, J. & Hunt, D. F. "Peptide and protein sequence analysis by electron transfer dissociation mass spectrometry", Proc. Natl. Acad. Sci. 101, 9528-9533 (2004); End et al., "An Approach to Correlate Tandem Mass Spectral Data of Peptides with Amino Acid Sequences in a Protein Database", J. Am. Soc. Mass Spectrom., 5:976-989, 1994; Swiderek K. et al. "The identification of peptide modifications derived from gel-separated proteins using electrospray triple quadrupole and ion trap analyses", Electrophoresis, 19:989-997, 1998; and Keough T. et al. "A method for high-sensitivity peptide sequencing using postsource decay matrix-assisted laser desorption ionization mass spectrometry", Proc. Natl. Acad. Sci USA, 96:7131-7136, 1999, the disclosures of which are herein incorporated by reference. Methods for employing mass spectrometry for amino acid sequencing is also discussed in greater detail in, e.g., Aebersold, R. & Mann, M. Mass spectrometry-based proteomics. Nature 422, 198-207 (2003); Steen, H. & Mann, M. The ABC's (and XYZ's) of peptide sequencing. Nat Rev Mol Cell Biol 5, 699-711 (2004); Eng, J. K., Searle, B. C., Clauser, K. R. & Tabb, D. L. A face in the crowd: recognizing peptides through database search. Mol Cell Proteomics 10, R111 009522 (2011), the disclosures of which are herein incorporated by reference.

Quantitative Methods

Also provided are quantitative IsoTag and quantitative proteomics methods utilizing the subject cleavable probes, which may provide for the precise measurement of both the glycome and proteome in a sample of interest. Any convenient quantitative proteomics methods may be adapted for use in the subject quantitative methods which include use of the subject cleavable probes. Methods and materials which may be adapted for use in the subject methods include those described by Bertozzi et al. in US Publication No. 2014/0199716; Tao and Aebersold, "Advances in quantitative proteomics via stable isotope tagging and mass spectrometry", Current Opinion in Biotechnology, Volume 14, Issue 1, February 2003, Pages 110-118; and Bantscheff et al., "Quantitative mass spectrometry in proteomics: a critical review", Analytical and Bioanalytical Chemistry, October 2007, Volume 389, Issue 4, pp 1017-1031, the disclosures of which are herein incorporated by reference in their entirety. Quantitative mass spectrometry methods of interest, include but are not limited to, those strategies described in FIG. 2 of Bantscheff et al 2007, e.g., where metabolic labelling includes two experimental conditions with two samples that are subsequently combined prior to quantitative MS analysis. See for example, present FIG. 12 where heavy and light samples are combined to provide for a quantitative analysis.

Figure 12:
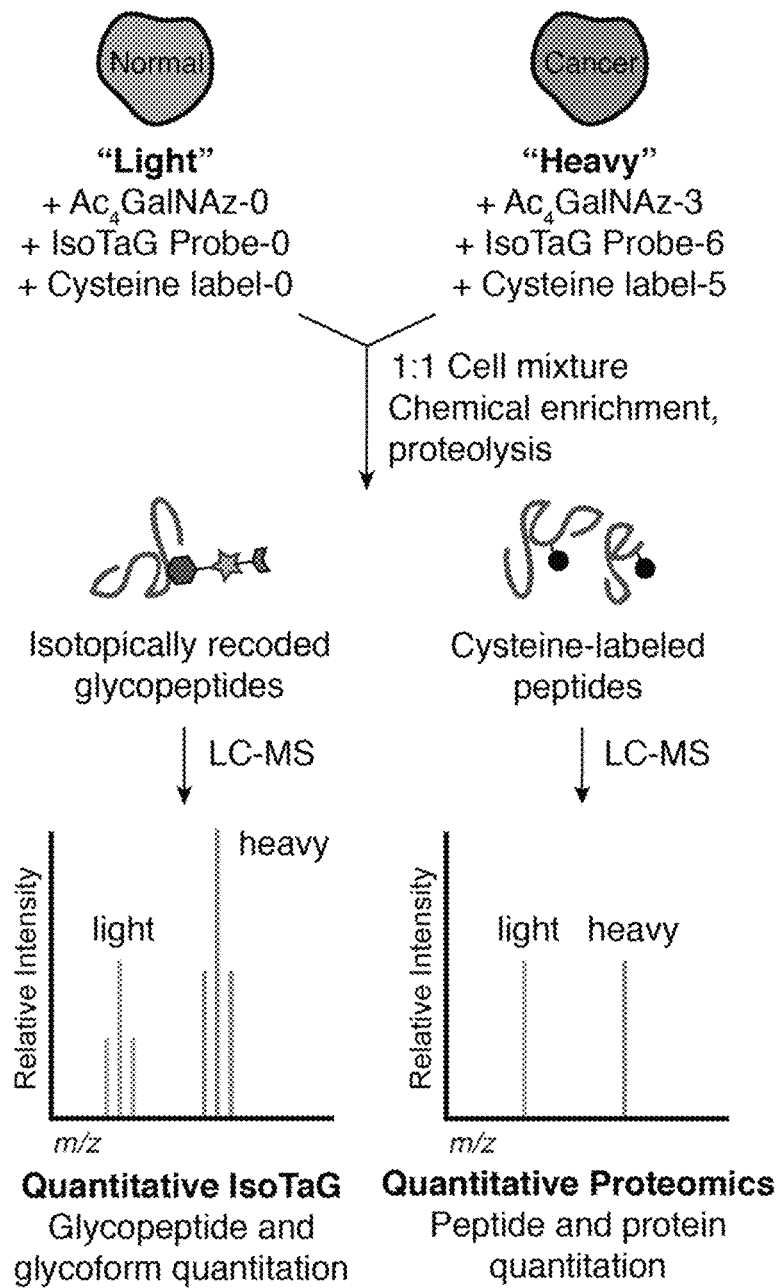
FIG. 12 illustrates a quantitative method of determining glycopeptide and glycoform levels and peptide and protein levels in samples of interest.
Figure 13:
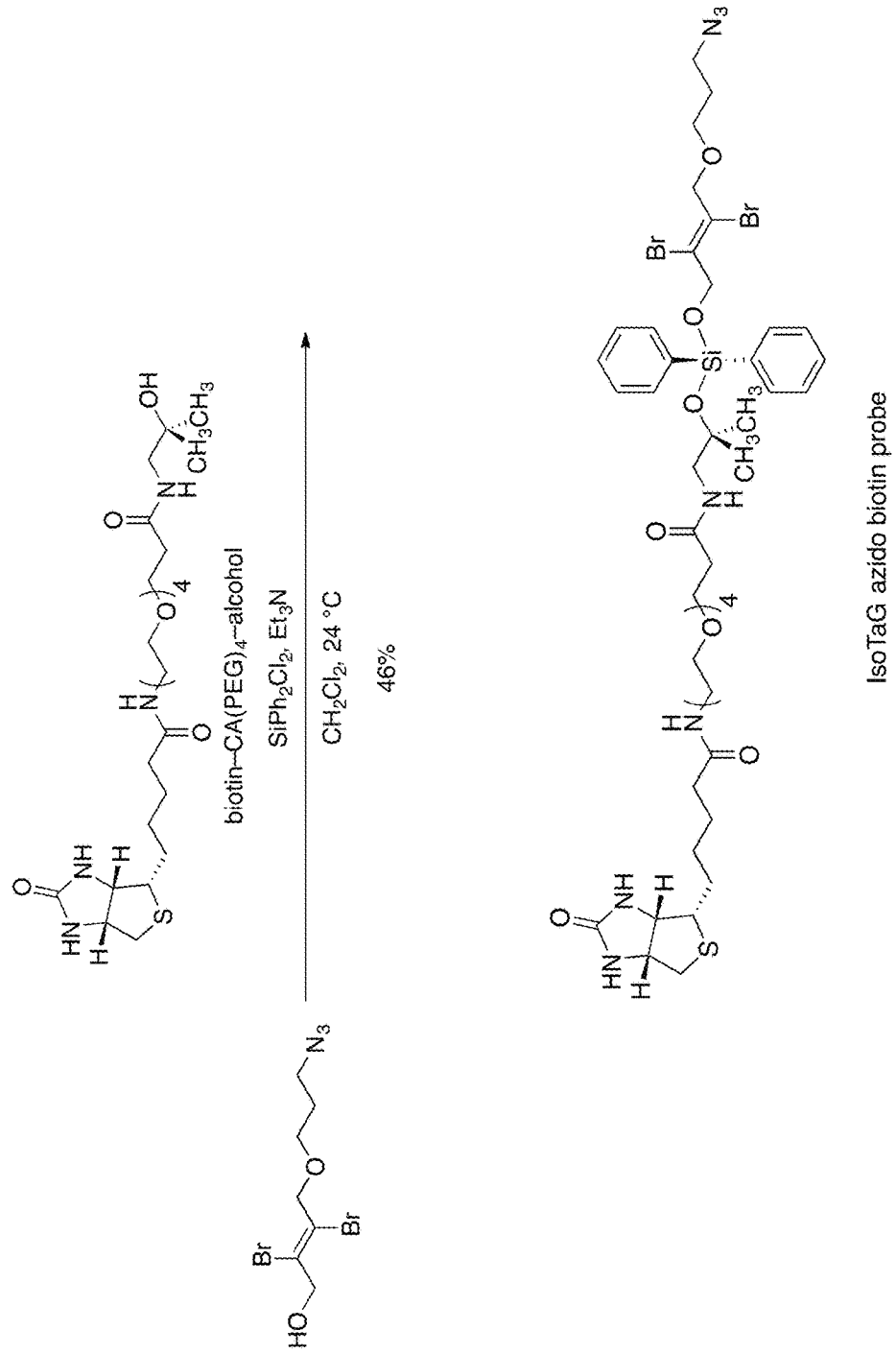
FIG. 13 illustrates the preparation of a cleavable probe (IsoTaG azido biotin) which includes a dibrominated isotopic label and a terminal azido group.

FIG. 12 illustrates a quantitative method of determining glycopeptide and glycoform levels and peptide and protein levels in sample of interest. Quantitative glycoproteomics can determine whether fluctuations in particular glycoproteins are reflective of changes in the proteome or the glycome, by using IsoTaG for identification of intact glycopeptides, and separate quantitation of the glycan and the peptide. Samples for comparison (e.g., normal vs. cancer) may be labeled with a light or heavy (i.e., isotopically labelled) glycan, respectively. Differential metabolic tagging may be utilized to generate isotopically recoded glycopeptides, e.g., with a 7 Da window between light and heavy samples, to provide for relative quantitation of the glycoform. In some cases, the method may include simultaneous introduction of direct protein-labeling using an orthogonal chemistry for quantitative proteomics of glycoproteins. The use of a second probe specific for an amino acid residue of a protein, rather than a glycosyl group of a glycoprotein of interest may provide for a comparison of the total level of a protein of interest versus the level of its glycoprotein form(s) in a sample. Any convenient protein linking group and chemistries may be adapted for use in protein specific probes in the subject quantitative methods.

Any convenient protein specific probes may be utilized in the subject quantitative methods. The protein specific probe may include a protein linking group and an isotopic label. As used herein, the term "protein linking group" refers to a group that is capable of reacting directly either spontaneously or after activation through contact with a stimulus, e.g., light, with an accessible sidechain functional group of a protein under aqueous conditions to produce a covalent linkage to the protein. The protein linking group is capable of reacting under aqueous conditions at which proteins of interest are able to be maintained in a folded state (e.g., physiological conditions). The protein linking group may react with the sidechain functional groups of a Lys, Cys, Ser, Thr, Tyr, His or Arg amino acid residue in a protein of interest to produce a covalent linkage to the protein. The protein linking group may also react with a terminal group of the protein, e.g., the amino terminus. Thus, the protein linking group may be amino-reactive, thiol-reactive, hydroxyl-reactive, imidazolyl-reactive or guanidinyl-reactive. Exemplary protein linking groups include active esters (e.g., an amino-reactive NHS ester), and thiol-reactive groups, such as maleimide or iodoacetamide groups. Further exemplary protein linking groups and methods of using the same are described in Hermanson, "Bioconjugate Techniques" 2nd Edition, Academic Press, 2008. In certain embodiments, the protein specific probe include a protein linking group selected from N-hydroxysuccinimidyl ester, sulfo-N-hydroxysuccinimidyl ester, a halo-substituted phenol ester, pentafluorophenol ester, a nitro-substituted phenol ester, an anhydride, isocyanate, isothiocyanate, an imidoester, maleimide, iodoacetyl, hydrazide, an aldehyde, an epoxide, an amino and a photoreactive linking group.

As used herein, the term "to cross-link" refers to the process of linking two moieties or atoms to each other via a covalent bond. An exemplary cross-linking process is the reaction of a protein linking group with the sidechain residue of a protein of interest to produce a stable covalent linkage.

As such, the subject quantitative methods may include contacting two or more samples (e.g., a control or normal sample, and a sample of interest as described in FIG. 12) with a heavy or a light version of a number of reagents selected from the subject cleavable probes, tagged sugars and/or protein specific probes. As used herein, the terms "heavy" and "light" refer to analogs of a reagent which include distinct isotopic labels that provide for differentiation and comparison of analytes based on mass during MS analysis.

In some embodiments of the method, the tagged sugar and the produced metabolically tagged protein include an isotopic label. In certain embodiments of the method, the method further includes quantitating a glycoprotein of the sample. In some instances, the method further includes contacting the sample with a protein specific probe capable of cross-linking an amino acid residue of the protein to produce a labelled protein; and digesting the labelled protein to produce a labelled peptide. In certain embodiments of the method, the method further includes quantitating the total amount of a protein of interest of the sample.

Systems

Also provided is a computer system having an algorithm that is used to perform one or more mass spectroscopic analysis steps of the subject methods. In some cases, the subject system includes an algorithm for identifying isotopically labeled peptides by full scan mass spectrometry prior to tandem MS analysis. In certain cases, the subject system includes an algorithm for identifying peptides having a predetermined isotopic pattern and determining the sequence of amino acids of peptides determined to include the desired isotopic pattern. In certain embodiments, system also includes a computer that includes a computer readable storage medium having a computer program stored thereon, where the computer program when loaded on a computer operates the computer to: receive spectra from a mass spectrometer and includes a processor to assess the mass spectra to identify a predetermined isotopic pattern of an peptide in the mass spectra and for determining the presence of N-glycosylation or O-glycosylation on the peptide based on the determined glycan monomer or sequence.

Kits

Also provided by the present disclosure are kits for practicing the above described subject method. The subject kits may contain at least the cleavable probe (e.g., as described herein). The kit may also contain one or more components for practicing the subject methods (e.g., as described herein), such as reagents for metabolically tagging proteins, reagents for cleaving the cleavable probe, reagents and supports for affinity purification, etc., and may also contain positive and/or negative controls to be run in conjunction with an assay. The various components of the kit may be present in separate containers or certain compatible components may be pre-combined into a single container, as desired.

In some embodiments, the kit includes a cleavable probe (e.g., as described above) and one or more components selected from: an enzyme, a chemical cleavage agent, a light source, a buffer, a cell, a tagged protein (e.g., a metabolically tagged protein), a tagged sugar and positive and/or negative controls.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: General Experimental Procedures

All reactions were performed in single-neck, flame-dried, round-bottomed flasks fitted with rubber septa under a positive pressure of nitrogen, unless otherwise noted. Air- and moisture-sensitive liquids were transferred via syringe or stainless steel cannula. Organic solutions were concentrated by rotary evaporation at 30-33° C. Normal and reverse phase flash-column chromatography was performed as described by Still and co-workers.[1] Normal phase purifications employ silica gel (60 Å, 40-63 µm particle size) purchased from Silicycle (Quebec, Canada). Analytical thin-layered chromatography (TLC) was performed using glass plates pre-coated with silica gel (0.25 mm, 60 Å pore size) impregnated with a fluorescent indicator (254 nm). TLC plates were visualized by exposure to ultraviolet light (UV) and/or submersion in aqueous ceric ammonium molybdate solution (CAM) followed by brief heating on a hot plate (120° C., 10-15 s).

Chemical Materials. Commercial solvents and reagents were used as received with the following exceptions. Dichloromethane and N,N-dimethylformamide were purified according to the method of Pangborn and co-workers (Pangborn, A. B.; Giardello, M. A.; Grubbs, R. H.; Rosen, R. K.; Timmers, F. J. *Organometallics* 1996, 15, 1518). Triethylamine was distilled from calcium hydride under an atmosphere of nitrogen immediately before use. Rapigest was prepared according to the method of Lee and co-workers (Lee, P. J. J.; Compton, B. J.; Patent, U. S., Ed.; Waters Investments Limited: USA, 2007; Vol. 7229539). BTTP was prepared according to the method of Wu and co-workers (Wang, W.; Hong, S.; Tran, A.; Jiang, H.; Triano, R.; Liu, Y.; Chen, X.; Wu, P. *Chemistry—An Asian Journal* 2011, 6, 2796). Tetraacetylated N-azidoacetyl galactosamine was prepared according to the method of Bertozzi and co-workers (Hang, H. C.; Yu, C.; Kato, D. L.; Bertozzi, C. R. *Proceedings of the National Academy of Sciences* 2003, 100, 14846). Tetraacetylated N-azidoacetyl mannosamine was prepared according to the method of Bertozzi and co-workers (Prescher, J. A.; Dube, D. H.; Bertozzi, C. R. *Nature* 2004, 430, 873).

Cell Culture Materials. Jurkat, PC-3, and MCF-7 cell lines were obtained from the American Type Culture Collection (ATCC). Jurkat and PC-3 cells were maintained in RPMI-1640 supplemented with 10% FBS and 1% penicillin/streptomycin. MCF-7 cells were maintained in DMEM supplemented with 10% FBS and 1% penicillin/streptomycin. EDTA-free protease inhibitor cocktail was obtained from Roche Diagnostics (Version 11). Streptavidin-agarose beads were obtained from Thermo Scientific and washed with PBS prior to use.

Instrumentation. Proton nuclear magnetic resonance spectra ($^1$H NMR) were recorded at 400 or 600 MHz at 24° C., unless otherwise noted. Chemical shifts are expressed in parts per million (ppm, δ scale) downfield from tetramethylsilane and are referenced to residual protium in the NMR solvent (CHCl$_3$, δ 7.26; CHD$_2$OD, δ 3.31). Data are represented as follows: chemical shift, multiplicity (s=singlet, d=doublet, t=triplet, q=quartet, quin=quintet, m=multiplet and/or multiple resonances, br=broad, app=apparent), integration, coupling constant in Hertz, and assignment. Proton-decoupled carbon nuclear magnetic resonance spectra ($^{13}$C NMR) were recorded at 100 or 125 MHz at 24° C., unless otherwise noted. Chemical shifts are expressed in parts per million (ppm, δ scale) downfield from tetramethylsilane and are referenced to the carbon resonances of the solvent (CDCl$_3$, δ 77.0; CD$_3$OD, δ 49.0). $^{13}$C NMR and data are represented as follows: chemical shift, carbon type [determined from HSQC]. Chemical shifts are expressed in parts per million (ppm, δ scale) downfield from tetramethylsilane. Infrared (IR) spectra were obtained using a Thermo Electron Corporation Nicolet 8500 FTIR spectrometer referenced to a polystyrene standard. Data are represented as follows: frequency of absorption (cm$^{-1}$), intensity of absorption (s=strong, m=medium, w=weak, br=broad). High-resolution mass spectrometry (HRMS) were obtained using an instrument equipped with a dual API/ESI high-resolution mass spectrometry detector and photodiode array detector. Liquid chromatography-tandem mass spectrometry was obtained using a Thermo Dionex UltiMate3000 RSLCnano liquid chromatograph that was connected in-line with an LTQ Orbitrap XL mass spectrometer equipped with a nanoelectrospray ionization (nanoESI) source (Thermo Fisher Scientific, Waltham, Mass.). Mass spectrometry data were analyzed with Proteome Discoverer v1.4 using SEQUEST HT and Byonic v2.0 algorithms. Mass spectrometry data are annotated as losses from the MS$^{(n-1)}$ precursor mass as follows: glycan (number of glycan units) in reverse order of the observed losses. Multiple glycans at separate sites are separated by comma. Glycan annotations used: HexNAzBr2OH=C$_{15}$H$_{20}$Br$_2$N$_4$O$_7$ (+527.9678, abbreviated HexNAz*), HexNAz=C$_8$H$_{12}$N$_4$O$_5$ (+244.0808), HexNAcNH$_2$=C$_8$H$_{14}$N$_2$O$_5$ (+218.0903), HexNAc=C$_8$H$_{13}$NO$_5$ (+203.0794), NeuAzBr2OH=C$_{18}$H$_{24}$Br$_2$N$_4$O$_{10}$ (+615.9839, abbreviated NeuAz*), NeuAz=C$_{11}$H$_{16}$N$_4$O$_8$ (332.0968), NeuAcNH$_2$=C$_{11}$H$_{18}$N$_2$O$_8$ (306.1063), NeuAc=C$_{11}$H$_{17}$NO$_8$ (291.0954), Hex=C$_6$H$_{10}$O$_5$ (162.0528), +CO═CO (27.9949, occurs on the O-terminus of the tag).

Example 2: Synthetic Procedures

Scheme 1: Synthesis of a cleavable silane probe 1

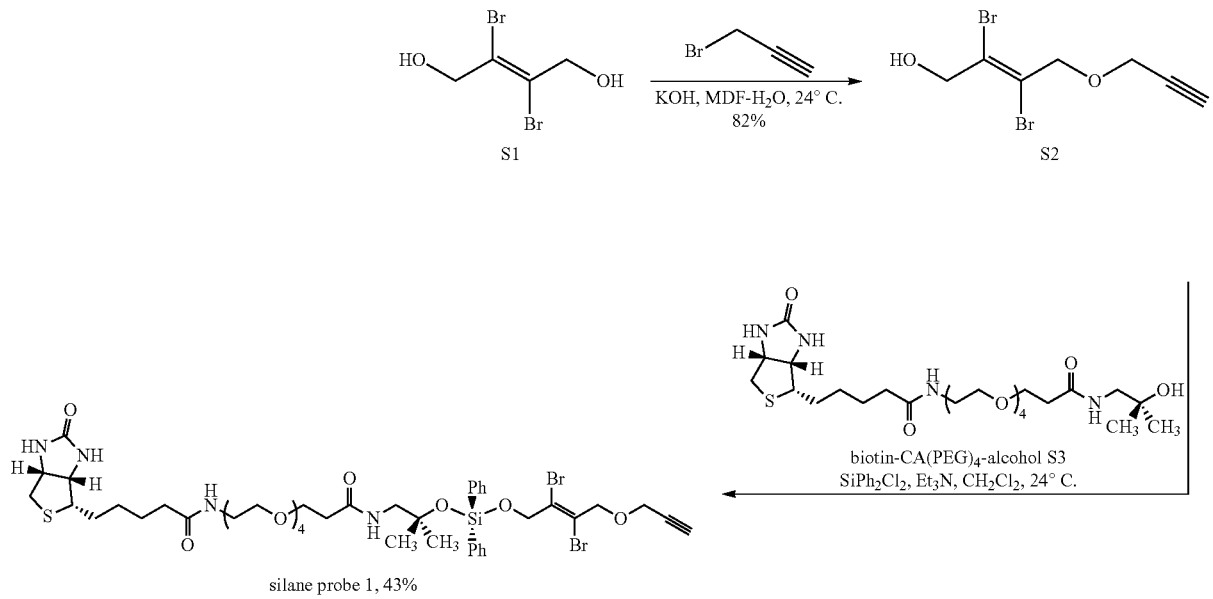

Synthesis of (E)-2,3-Dibromo-4-(prop-2-yn-1-yloxy)but-2-en-1-ol (S2)

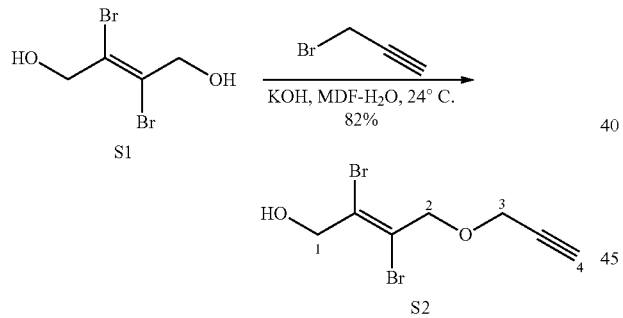

Propargyl bromide (80% solution in toluene, 1.25 mL, 11.6 mmol, 1 equiv) was added to a stirred solution of (E)-2,3-dibromobut-2-ene-1,4-diol (S1, 8.56 g, 34.8 mmol, 3.00 equiv) and potassium hydroxide (1.30 g, 23.2 mmol, 2.00 equiv) in 50% N,N-dimethylformamide-water (30 mL) at 24° C. The resulting mixture was stirred for 12 h at 24° C. The product mixture was purified by flash-column chromatography (eluting with 25% ethyl acetate-hexanes, grading to 100% ethyl acetate, one step) to afford (E)-2,3-dibromo-4-(prop-2-yn-1-yloxy)but-2-en-1-ol (S2) as a white solid (2.69 g, 82%). $R_f$=0.26 (20% ethyl acetate-hexanes; CAM). $^1$H NMR (400 MHz, CDCl$_3$): δ 4.49 (s, 4H, H$_1$/H$_2$), 4.14 (d, 2H, J=2.4 Hz, H$_3$), 3.28 (t, 1H, J=6.8 Hz, OH), 2.49 (t, 1H, J=2.4 Hz, H$_4$). $^{13}$C NMR (600 MHz, CDCl$_3$): δ 125.3 (C), 118.6 (C), 78.8 (C), 75.5 (CH), 72.8 (CH$_2$), 66.8 (CH$_2$), 57.2 (CH$_2$). IR (NaCl), cm$^{-1}$: 3295 (br), 1092 (m), 642 (m). HRMS-ESI (m/z): [M+H] calculated for C$_7$H$_8$$^{79/81}$Br$_2$O$_2$, 283.8871; found, 283.8878.

Synthesis of the Silane Probe 1:

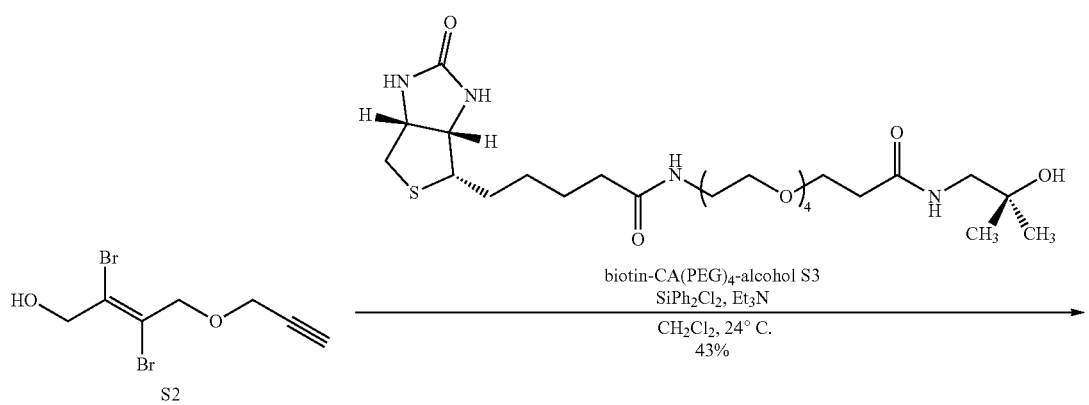

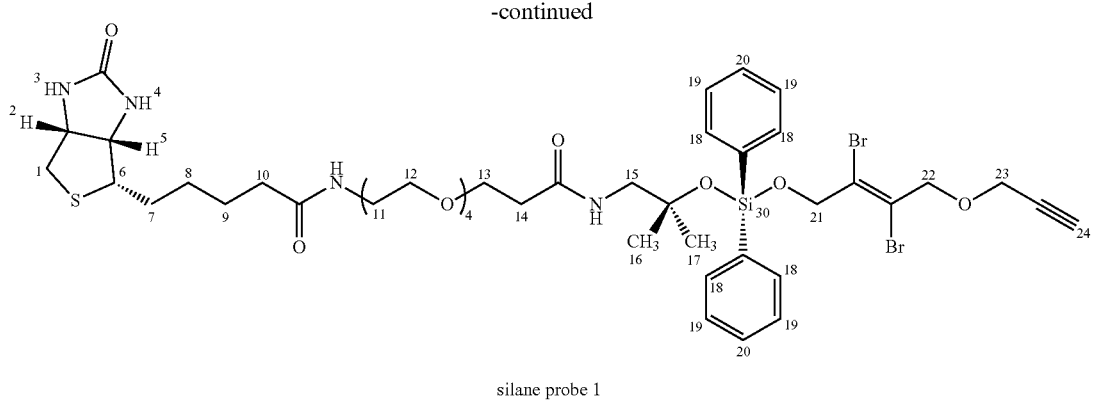

silane probe 1

Triethylamine (43.2 µL, 312 µmol, 9.00 equiv) and dichlorodiphenylsilane (21.9 µL, 104 µmol, 3.00 equiv) were added in sequence to a stirred solution of the biotin-CA(PEG)$_4$-alcohol S3 (Szychowski, J.; Mahdavi, A.; Hodas, J. J.; Bagert, J. D.; Ngo, J. T.; Landgraf, P.; Dieterich, D. C.; Schuman, E. M.; Tirrell, D. A. *J Am Chem Soc* 2010, 132, 18351) (19.5 mg, 34.6 µmol, 1 equiv) in dichloromethane (690 µL) at 24° C. The resulting solution was stirred for 2 h at 24° C. (E)-2,3-dibromo-4-(prop-2-yn-1-yloxy)but-2-en-1-ol (S2, 59.0 mg, 208 µmol, 6.00 equiv) was added to the stirred solution at 24° C. The resulting solution was stirred for an additional 1 h at 24° C. The product mixture was diluted sequentially with dichloromethane (10 mL) and saturated aqueous sodium bicarbonate solution (10 mL). The resulting biphasic mixture was transferred to a separatory funnel and the layers that formed were separated. The aqueous layer was extracted with dichloromethane (3×10 mL), and the organic layers were combined. The combined organic layers were dried over sodium sulfate. The dried solution was filtered, and the filtrate was concentrated. The residue obtained was purified by flash-column chromatography (eluting with 1% methanol-dichloromethane, grading to 10% methanol-dichloromethane, 3 steps) to afford the silane probe 1 as a clear oil (15.4 mg, 43%). $R_f$=0.54 (5% methanol-dichloromethane; CAM). $^1$H NMR (400 MHz, CD$_3$OD): δ 7.69 (d, 4H, J=6.4 Hz, H$_{18}$), 7.45 (t, 2H, J=7.2 Hz, H$_{20}$), 7.39 (t, 4H, J=7.2 Hz, H$_{19}$), 4.72 (s, 2H, H$_{21}$/H$_{22}$), 4.50 (s, 2H, H$_{21}$/H$_{22}$), 4.48 (dd, 1H, J=8.0, 4.8 Hz, H$_2$), 4.29 (dd, 1H, J=8.0, 4.8 Hz, H$_5$), 4.11 (d, 2H, J=2.4 Hz, H$_{23}$), 3.72 (t, 2H, J=6.0 Hz, H$_{14}$), 3.64-3.53 (m, 16H, H$_{11}$/H$_{12}$/H$_{15}$), 3.35-3.33 (m, 4H, H$_{11}$/H$_{12}$), 3.19 (dt, 1H, J=8.4, 5.6 Hz, H$_6$), 2.93-2.89 (m, 2H, H$_{24}$/H$_1$), 2.70 (d, 1H, J=12.4 Hz, H$_1$), 2.48 (t, 2H, J=6.4 Hz, H$_{13}$), 2.21 (t, 2H, J=7.2 Hz, H$_{10}$), 1.75-1.54 (m, 4H, H$_7$/H$_9$), 1.47-1.39 (m, 2H, H$_8$), 1.28 (s, 6H, H$_{16}$/H$_{17}$). $^{13}$C NMR (600 MHz, CD$_3$OD): 176.1 (C), 174.1 (C), 166.0 (C), 136.2 (3×CH), 135.0 (2×C), 131.5 (2×CH), 128.9 (3×CH), 125.5 (C), 120.2 (C), 80.1 (C), 77.3 (CH$_2$), 76.6 (CH$_2$), 73.7 (CH$_2$), 71.6 (CH$_2$), 71.5 (2×CH$_2$), 71.4 (CH$_2$), 71.3 (CH$_2$), 71.2 (CH$_2$), 70.7 (CH$_2$), 68.4 (CH$_2$), 68.2 (CH$_2$), 63.4 (CH), 61.6 (CH), 58.0 (CH$_2$), 57.0 (CH$_2$), 51.6 (C), 50.7 (2×CH$_2$, determined indirectly from HSQC), 41.1 (CH$_2$), 40.4 (CH$_2$), 37.8 (CH$_2$), 36.7 (CH$_2$), 29.8 (CH$_2$), 29.5 (CH$_2$), 28.2 (2×CH$_3$), 26.8 (CH$_2$). IR (NaCl), cm$^{-1}$: 2900 (br), 1643 (s), 1115 (s). HRMS-ESI (m/z): [M+Na] calculated for C$_{44}$H$_{62}^{79/79;79/81;81/81}$Br$_2$N$_4$O$_{10}$SSiNa, 1047.2215/1049.2199/1051.2179; found, 1047.2216/1049.2183/1051.2182.

Example 3: Cell Culture and Enrichment Procedures

All cell lines were obtained from the American Type Culture Collection (ATCC) and maintained at 37° C. and 5% CO$_2$ in a water-saturated incubator. Cell lines were metabolically labeled between passages 4-7 (MCF-7), 6-10 (Jurkat), or 17-22 (PC-3). Cell densities were counted using a hemacytometer and seeded at 1×10$^5$ cells/mL at the start of metabolic labeling experiments. Jurkat and PC-3 cells were maintained in RPMI-1640 supplemented with 10% FBS and 1% penicillin/streptomycin. MCF-7 cells were maintained in DMEM supplemented with 10% FBS and 1% penicillin/streptomycin.

Metabolic Labeling of Adherent Cell Lines (PC-3, MCF-7):

Tetraacetylated N-azidoacetylgalactosamine (Ac$_4$GalNAz) and tetraacetylated N-azidoacetylmannosamine (Ac$_4$ManNAz) were prepared as 500 mM stock solutions in dimethylsulfoxide (DMSO). Tissue culture dishes (150 mm) were seeded with 100 µM of Ac$_4$GalNAz, Ac$_4$ManNAz, or vehicle control containing DMSO (3.0 µL). Six dishes per condition were prepared. A suspension of cells at a density of 1×10$^5$ cells/mL were added to the dish (15 mL per dish) and the dishes were incubated for 48 h at 37° C. in a humidified 5% CO$_2$ incubator. Dishes containing adherent cells were aspirated and the dishes were washed with PBS (1×10 mL). Washed dishes were resuspended in complete media containing 100 µM glycan metabolite without FBS additive (15 mL), and the cells were incubated an additional 48 h at 37° C. in a humidified 5% CO$_2$ incubator.

Media (100 mL) was harvested and cleared by centrifugation (75×g, 3 min). Clarified media was spin concentrated (Amicon, 15 mL 10 kDa spin filter) to 1 mL. The concentrated residue was washed with PBS (3×15 mL), and transferred to an eppendorf as the "conditioned media fraction". Adherent cells were washed with PBS (1×10 mL) and trypsinized for 5 min at 37° C. Cells were harvested, centrifuged (150×g, 3 min), and washed with PBS (1×5 mL). Cell pellets were resuspended in lysis buffer (10 mM HEPES, pH 7.9, 15 mM MgCl$_2$, 10 mM KCl, 0.5% tritonx 100, 1×protease inhibitors, 1 µM thiamet G, 2 mL), swelled for 5 min on ice, and broken by Dounce homogenization using a tight glass hand pestle (Wheaton, 30 strokes). The homogenized lysate was transferred to a centrifuge tube, and insoluble material was pelleted by centrifugation (3700×g, 10 min, 4° C.). The supernatant was collected as the "soluble fraction" and the pellet kept as the "insoluble fraction." The conditioned media and soluble fractions were adjusted to a final concentration of 1% rapigest/PBS with a 10% rapigest/

PBS stock solution. The insoluble fraction was resuspended in 1% rapigest/PBS (1 mL) and briefly probe sonicated (Misionix). Protein concentration from the three fractions was measured by bicinchonic acid assay (Pierce) and normalized to 4.5 mg/mL.

Metabolic Labeling of Suspension Cell Lines (Jurkat):

Tetraacetylated N-azidoacetylgalactosamine ($Ac_4GalNAz$) and tetraacetylated N-azidoacetylmannosamine ($Ac_4ManNAz$) were prepared as 500 mM stock solutions in dimethylsulfoxide (DMSO). Tissue culture flasks (T-160) were seeded with 100 μM of $Ac_4GalNAz$, $Ac_4ManNAz$, or vehicle control containing DMSO (3.0 μL). Two flasks per condition were prepared. A suspension of cells at a density of $1×10^5$ cells/mL were added to the flask (50 mL per flask) and the flasks were incubated for 48 h at 37° C. in a humidified 5% $CO_2$ incubator. Media containing suspension cells was transferred to centrifuge tubes, and the cells were pelleted (150×g, 3 min). The media was aspirated, and cell pellets were washed with PBS (1×10 mL). Washed cells were resuspended in complete media containing 100 μM glycan metabolite without FBS additive (50 mL/flask). The cells were transferred to tissue culture flasks (T-160), and incubated an additional 48 h at 37° C. in a humidified 5% $CO_2$ incubator.

Media containing suspension cells was transferred to centrifuge tubes, and the cells were pelleted (150×g, 3 min). Clarified media was spin concentrated (Amicon, 15 mL 10 kDa spin filter) to 1 mL. The concentrated residue was washed with PBS (3×15 mL), and transferred to an eppendorf as the "conditioned media fraction". Pelleted cells were washed with PBS (2×10 mL) and centrifuged at 150×g for 3 min. Cell pellets were resuspended in lysis buffer (10 mM HEPES, pH 7.9, 15 mM $MgCl_2$, 10 mM KCl, 0.5% tritonx 100, 1× protease inhibitors, 1 μM thiamet G, 2 mL), swelled for 5 min on ice, and broken by Dounce homogenization using a tight glass hand pestle (Wheaton, 30 strokes). The homogenized lysate was transferred to a centrifuge tube, and insoluble material was pelleted by centrifugation (3700×g, 10 min, 4° C.). The soluble supernatant was collected as the "soluble fraction" and the pellet kept as the "insoluble fraction." The conditioned media and soluble fractions were adjusted to a final concentration of 1% rapigest/PBS with a stock solution of 10% rapigest/PBS. The insoluble fraction was resuspended in 1% rapigest/PBS (1 mL) and briefly probe sonicated (Misionix). Protein concentration from the three fractions was measured by bicinchonic acid assay (Pierce) assay and normalized to 4.5 mg/mL.

Chemical Glycoproteomics Enrichment Procedure:

GalNAz-labeled, ManNAz-labeled, or DMSO vehicle treated cell fractions were aliquoted to 3.0 mg fractions (667 μL). Click chemistry reagents (40.0 μL, 200 μM 1, 300 μM $CuSO_4$, 600 μM BTTP,[4] 1.50 mM sodium ascorbate, mixed immediately before addition to lysates) were added and the reaction was incubated for 3.5 h at 24° C. Methanol (1 mL) was added to quench the reaction, and proteins were precipitated for 1 h at -80° C. Precipitated proteins were pelleted by centrifugation (16.1×g, 10 min, 4° C.) and the supernatant was discarded. Pelleted proteins were air-dried for 10 min at 24° C. Dried protein pellets were resuspended in 400 μL 1% rapigest/PBS and solubilized by probe sonication (Misionix, 1.5 min, 4° C.). Streptavidin-agarose resin [200 μL, washed with PBS (3×1 mL)] was added, and the resulting mixture was incubated for 12 h at 24° C. with rotation. The beads were pelleted by centrifugation (3000×g, 3 min) and the supernatant containing uncaptured proteins was separated. The beads were washed with 1% rapigest/PBS (1 mL), 6 M urea (2×1 mL), and PBS (5×1 mL), and the beads were pelleted by centrifugation (3000×g, 3 min) between washes.

Washed beads were resuspended in 5 mM DTT/PBS (200 μL) and incubated for 30 min at 24° C. with rotation. Ten mM iodoacetamide (4.0 μL, 1 M stock solution) was added to the reduced proteins, and allowed to react for 30 min at 24° C. with rotation in the dark. Beads were pelleted by centrifugation (3000×g, 3 min) and resuspended in 0.5 M urea/PBS (200 μL). Trypsin (1.5 μg) was added to the resuspended beads, and digestion proceeded for 12 h at 37° C. Beads were pelleted by centrifugation (3000×g, 3 min), and the supernatant digest was collected. The beads were washed with PBS (1×200 μL) and $H_2O$ (2×200 μL). Washes were combined with the supernatant digest to form the trypsin digest. The silane tag 1 was cleaved with two treatments of 2% formic acid/$H_2O$ (200 μL) for 30 min at 24° C. with rotation and the eluent was collected. The beads were washed with 50% acetonitrile-water+1% formic acid (2×200 μL), and the washes were combined with the eluent to form the cleavage fraction. The trypsin digest and cleavage fraction were concentrated on speed vac (40° C.) to 50-100 μL. Samples were desalted by ZipTip P10 and stored at −20° C. until analysis.

Example 4: Mass Spectrometry Procedures

Trypsin-digested proteins were analyzed using a Thermo Dionex UltiMate3000 RSLCnano liquid chromatograph that was connected in-line with an LTQ Orbitrap XL mass spectrometer equipped with a nanoelectrospray ionization (nanoESI) source (Thermo Fisher Scientific, Waltham, Mass.). The LC was equipped with a C18 pre-column (Acclaim® PepMap 100, 20 mm length×0.075 mm inner diameter, 3 μm particles, 100 Å pores, Thermo), a C18 analytical column (Acclaim® PepMap 300, 150 mm length× 0.075 mm inner diameter, 5 μm particles, 300 Å pores, Thermo) and a 1 μL sample loop. Acetonitrile (Fisher Optima grade, 99.9%), formic acid (1 mL ampules, 99+%, Thermo Pierce), and water purified to a resistivity of 18.2 MΩ·cm (at 25° C.) using a Milli-Q Gradient ultrapure water purification system (Millipore, Billerica, Mass.) were used to prepare mobile phase solvents. Solvent A was 99.9% water/0.1% formic acid and solvent B was 99.9% acetonitrile/0.1% formic acid (v/v). Samples contained in polypropylene autosampler vials with septa caps (Agilent, Santa Clara, Calif.) were loaded into the autosampler compartment prior to analysis. The autosampler compartment was maintained at 4° C. The elution program consisted of isocratic flow at 2% B for 4 min, a linear gradient to 50% B over 98 min, isocratic flow at 95% B for 6 min, and isocratic flow at 2% B for 12 min, at a flow rate of 300 nL/min. The column exit was connected to the nanoESI emitter in the ion source of the mass spectrometer using polyimide-coated, fused-silica tubing (20 μm inner diameter×280 μm outer diameter, Thermo).

Full-scan mass spectra were acquired in the positive ion mode over the range m/z=400 to 1800 using the Orbitrap mass analyzer, in profile format, with a mass resolution setting of 60,000 (at m/z=400, measured at full width at half-maximum peak height, FWHM). The lock mass feature was enabled to provide real-time internal mass calibration using known background ions.[8] In the data-dependent mode, the three most intense ions exceeding an intensity threshold of 50,000 counts were selected from each full-scan mass spectrum for tandem mass spectrometry (MS/MS, i.e., $MS^2$) analysis using collision-induced dissociation (CID). $MS^2$ spectra were acquired using the linear ion trap or the Orbitrap analyzer (in the latter case, with a resolution setting of 7500 at m/z=400, FWHM), in centroid format, with the following parameters: isolation width 4 m/z units, normalized collision energy 28%, default charge state 3+, activation Q 0.25, and activation time 30 ms. The three most intense fragment ions in each MS$^2$ spectrum exceeding an intensity threshold of 1000 counts were selected for MS$^3$ analysis using CID. MS$^3$ spectra were acquired using the linear ion trap, in centroid format, with the same parameters as those used for MS$^2$. When MS$^2$ spectra were acquired using the Orbitrap analyzer, real-time charge state screening was enabled to exclude unassigned charge states from MS/MS analysis. To avoid the occurrence of redundant MS/MS measurements, real-time dynamic exclusion was enabled to preclude re-selection of previously analyzed precursor ions, with the following parameters: repeat count 1, repeat duration 30 s, exclusion list size 500, exclusion duration 90 s, and exclusion mass width ±1.5 m/z units. Global parent mass lists (i.e., inclusion lists) were enabled to specify the m/z values and retention times of glycopeptide precursor ions detected in full-scan mass spectra by the IsoStamp isotope pattern-searching algorithm. Data acquisition was controlled using Xcalibur software (version 2.0.7, Thermo).

Targeted Data Analysis Procedure.

The raw data was processed using Proteome Discoverer 1.4 software (Thermo Fisher Scientific) and searched against the human-specific SwissProt-reviewed database downloaded on Jul. 18, 2014. Indexed databases for tryptic digests were created allowing for three missed cleavages, one fixed modification (cysteine carboxyamidomethylation, +57.021), and variable modifications (methionine oxidation, +15.995; see below). Precursor ion tolerance from data collected in the Orbitrap and LTQ was set to 10 ppm and 1.5 Da, respectively. CID fragment tolerance was set to 0.8 Da. The SEQUEST HT search engine was used to initially identify dibrominated species by the mass defect using a modified HexNAc, termed "HexNAzBr$_2$OH" ($C_{15}H_{20}Br_2N_4O_7$, +527.9678), with variable attachment to serine, threonine, or asparagine. Tandem MS data were screened for glycopeptide signifiers including isotopically recoded precursor in the MS$^1$ and neutral or charged glycan losses in MS$^2$. Selected MS$^2$/MS$^3$ spectra were documented and saved separately. Saved spectra were manually annotated for glycoforms and peptide mass. Saved spectra were then searched iteratively using the Byonic search algorithm v2.0 as a node in Proteome Discoverer 1.4. Initial searches allowed singly tagged N- and O-glycan variable modifications (see input file below) using MS$^1$ or MS$^{(n-1)}$ as the precursor mass. Computational assignments of all spectra were validated by manual inspection for glycan and peptide fragments. High probability assignments were inspected for validity, and unassigned spectra were kept for continued identification. For MS$^{(n-1)}$ assignments, the assignment was validated for exact mass from the MS$^1$ (Δmass=<5 ppm). Unassigned spectra from the initial searches were sorted to glycan type based on the MS$^2$ fragmentation (e.g., HexNAc, elaborated O-glycan, or elaborated N-glycan) and searched with variable modification on a focused glycan database. Finally, spectra that remained low confidence assignments were then manually inspected for similarities to assigned spectra (i.e. characteristic peptide fragments), or searched against the UniprotKB database (downloaded on Sep. 30, 2014) with variable modification on the specific glycoform.

For discovery of peptide sequence polymorphisms, spectra that remained low confidence assignments from data sets collected with MS$^2$ in the Orbitrap were manually inspected for similarities to assigned spectra (i.e., characteristic peptide fragments). Spectra that were considered visually comparable to an assigned species were search against the protein assignment, with variable modifications on amino acid isoforms that fall within the difference in precursor masses. Matches were accepted if Δmass=<5 ppm and major fragments were assigned.

Text of Initial Byonic Glycan Modification Input File:
HexNAc(1) 324.88846 @ OGlycan|common2
HexNAc(1) @ OGlycan|common2
HexNAc(2) 324.88846 @ OGlycan|common1
HexNAc(1)Hex(1) 324.88846 @ OGlycan|rare2
HexNAc(2)Hex(1) 324.88846 @ OGlycan|rare2
HexNAc(1)Hex(1)NeuAc(1) 324.88846 @ OGlycan|rare2
HexNAc(1)Hex(1)NeuAc(2) 324.88846 @ OGlycan|rare2
HexNAc(1)NeuAc(1) 324.88846 @ OGlycan|rare2
HexNAc(1) 324.88846 @ NGlycan|common1
HexNAc(2) 324.88846 @ NGlycan|rare1
HexNAc(2)Hex(1) 324.8846 @ NGlycan|rare1
HexNAc(2)Hex(3) 324.88846 @ NGlycan|rare2
HexNAc(2)Hex(4) 324.88846 @ NGlycan|rare2
HexNAc(2)Hex(4) 324.88846 @ NGlycan|common1
HexNAc(2)Hex(5) 324.88846 @ NGlycan|common1
HexNAc(2)Hex(6) 324.88846 @ NGlycan|rare2
HexNAc(2)Hex(7) 324.88846 @ NGlycan|rare2
HexNAc(2)Hex(8) 324.88846 @ NGlycan|rare2
HexNAc(2)Hex(9) 324.88846 @ NGlycan|rare2
HexNAc(3)Hex(3) 324.88846 @ NGlycan|rare2
HexNAc(3)Hex(5) 324.88846 @ NGlycan|rare2
HexNAc(4)Hex(3) 324.88846 @ NGlycan|rare2
HexNAc(4)Hex(4) 324.88846 @ NGlycan|rare2
HexNAc(4)Hex(5) 324.88846 @ NGlycan|rare2
HexNAc(1) @ NGlycan|common2
HexNAc(1) 41.0014 @ OGlycan|common1
% Custom modification text below Example 5: Western Blotting Procedures α-Biotin Immunoblotting:

Aliquots collected during enrichment procedure (10 μL) were reduced and separated by standard SDS-PAGE (Bio-Rad, Criterion system), electroblotted onto nitrocellulose, blocked in 5% bovine serum albumin (Sigma) in Tris-buffered saline with Tween (10 mM Tris pH 8., 150 mM NaCl, 0.1% Tween-20), and analyzed by standard enhanced chemiluminescence immunoblotting methods (Pierce). Staining agent used: streptavidin-HRP (Pierce, 1:100,000).

Lectin Staining:

GalNAz-labeled or DMSO vehicle Jurkat media (100 μg) in buffer (25.0 μL, 50 mM NaOAc pH 5.5, 4 mM CaCl$_2$) was aliquoted in duplicate. One aliquot from each condition was treated with neuraminidase (4.0 μL, *V. cholerae*, Roche). Aliquots were mixed and incubated at 37° C. for 12 h. Aliquots (10 μL) were reduced and separated by standard SDS-PAGE (Bio-Rad, Criterion system), electroblotted onto nitrocellulose, blocked in Tris-buffered saline with Tween (10 mM Tris pH 8, 150 mM NaCl, 0.5% Tween-20), and analyzed by standard fluorescent imaging (Typhoon 9410, GE Healthcare). Staining agent used: peanut agglutinin-FITC (Vector Laboratories, 1:100).

Example 6: Results

A mass independent chemical glycoproteomics platform was developed for the enrichment and recovery of intact glycopeptides based on metabolically labeled glycans (e.g. Ac$_4$GalNAz, Ac$_4$ManNAz), as compared to glycan structure, followed by targeted glycoproteomics. The platform, termed isotope targeted glycoproteomics (IsoTaG), identifies enriched glycopeptides by full scan mass spectrometry (MS), prior to tandem MS analysis. The strategy utilizes the perturbing effect of a dibrominated chemical tag on the isotopic envelope of the glycopeptide to create a unique pattern that is visually and computationally recognizable. The pattern is then used as a handle to specifically target tagged glycopeptides for tandem MS, followed by targeted computational analysis for high confidence identification of the glycopeptide. A computational algorithm, termed isotopic signature transfer and mass pattern prediction (IsoStamp), is utilized for the detection of recoded species by full scan MS. Isotopic recoding in proteomics increases confidence in spectral assignment. An IsoTaG approach improves glycopeptide targeting by four-fold and leads to the identification of over 550 intact N-linked, O-linked, and O-GlcNAcylated glycopeptides from 240 glycoproteins across three cancer cell lines, of which 50% are novel glycoproteins and 60% are novel glycopeptides.

Figure 2A:
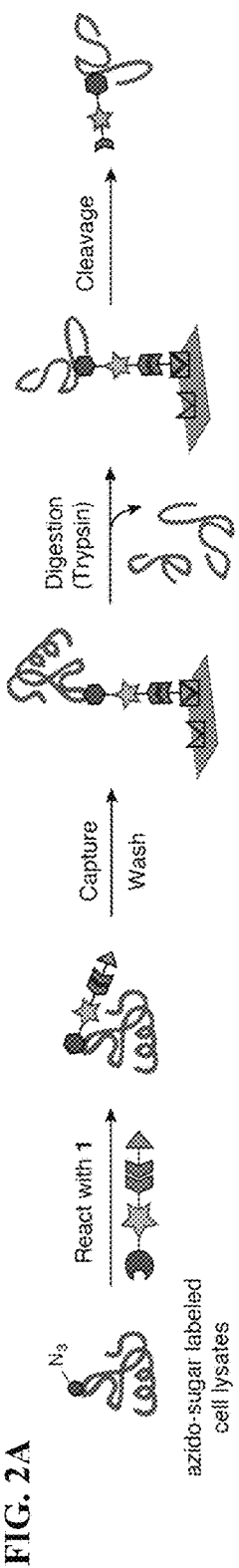
FIG. 2A-2C illustrate detection of low abundance glycopeptide species utilizing an exemplary probe and isotope targeted glycoproteomics (IsoTaG) enrichment method. (A) Depiction of an enrichment strategy using a cleavable silane probe 1. Metabolically labeled glycoproteins are enriched using a streptavidin affinity column. On-bead digestion removes non-glycosylated peptides, and isotopically recoded glycopeptides are cleaved and eluted from the resin. (B) Isotopically recoded glycopeptides are analyzed by reversed-phase liquid chromatography coupled to a Thermo LTQ-Orbitrap XL mass spectrometer. In traditional proteomics, tandem MS is performed on the n most abundant species in the full scan mass spectrum. (C) IsoTaG uses the IsoStamp pattern-searching algorithm to direct tandem MS (i.e., MS2 and MS3) analysis to isotopically recoded species. Targeted searching of selected species results in high confidence glycopeptide identification. The tagged glycan is denoted with a "Br$_2$". The depicted sequence LRPIIISM-NYSLPLR is SEQ ID NO: 36.

As depicted in FIG. 1, the multifunctional probe 1 provides for CuAAC, affinity enrichment, recovery of the glycopeptide, and isotopic recoding of the intact glycopeptide. A silane cleavable linker was utilized (see e.g., Szychowski, J. et al. Cleavable biotin probes for labeling of biomolecules via azide-alkyne cycloaddition. J Am Chem Soc 132, 18351-18360, (2010)) due to compatibility of the mild acid-cleavage step with glycopeptide stability. Incorporation of two bromine atoms in the form of trans-2,3-dibromo-2-butene-1,4-diol installs the unique isotopic signature (highlighted in red, FIG. 1). The natural abundances of the stable isotopes, $^{79}Br$ and $^{81}Br$ (1:1), provide a facile source of isotope recoding. Incorporation of two bromine atoms improves the sensitivity and false positive rate of the computational pattern-recognition algorithm. To obviate the possible occurrence of isomers in the downstream MS application, achiral fragments were selected for synthesis of the probe 1 (Scheme 1). The performance of probe 1 was tested for mass independent chemical glycoproteomics with Jurkat cells (FIG. 2A). Jurkat cells are treated with azide-functionalized glycans, which are metabolized by the cell and incorporated into their glycoprotein targets. To assess the compatibility of the approach with any metabolically labeled glycan type, Jurkat cells were metabolically labeled with 100 µM Ac$_4$ManNAz, Ac$_4$GalNAz, or DMSO vehicle for 48 h. Ac$_4$ManNAz is metabolized to the corresponding N-azidoacetyl sialic acid (SiaNAz) for sialoglycoprotein labeling. Ac$_4$GalNAz is processed by the cellular GalNAc salvage pathway to form UDP-GalNAz, which is interconverted by the UDP-galactose 4'-epimerase (GALE) to its C$_4$-epimer, UDP-GlcNAz. Thus, metabolic labeling with Ac$_4$GalNAz produces GalNAz-labeled mucin type O-glycoproteins, GlcNAz-labeled N-glycoproteins, and O-GlcNAcylated proteins. Labeled Jurkat cells were harvested by centrifugation, and the media was collected by centrifugal filtration for analysis of secreted glycoproteins. The cell pellet was homogenized and separated into soluble and insoluble fractions. Three mg/fraction was used as a starting point for glycoproteomics enrichment.

Figure 6A:
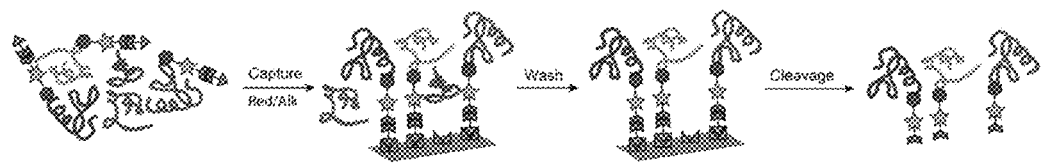
FIG. 6A-6B show a western blot analysis of an enrichment using the silane probe 1 and Jurkat whole cell lysate labeled with 100 μM Ac4GalNAz or DMSO vehicle. (A) Schematic diagram of an enrichment procedure used. (B) Western blot analysis of enriched Jurkat whole cell lysate. Biotinylated proteins (load) are enriched from the supernatant by affinity-capture on streptavidin-agarose beads. Avidin-agarose beads are reduced and alkylated, and washed with 1% rapigest, 6 M urea, and PBS. Beads are checked for anti-biotin signal before and after washing. Treatment with 2% formic acid cleaved silane probe 1 and released glycoproteins and glycopeptides from the agarose beads.
Figure 6B:
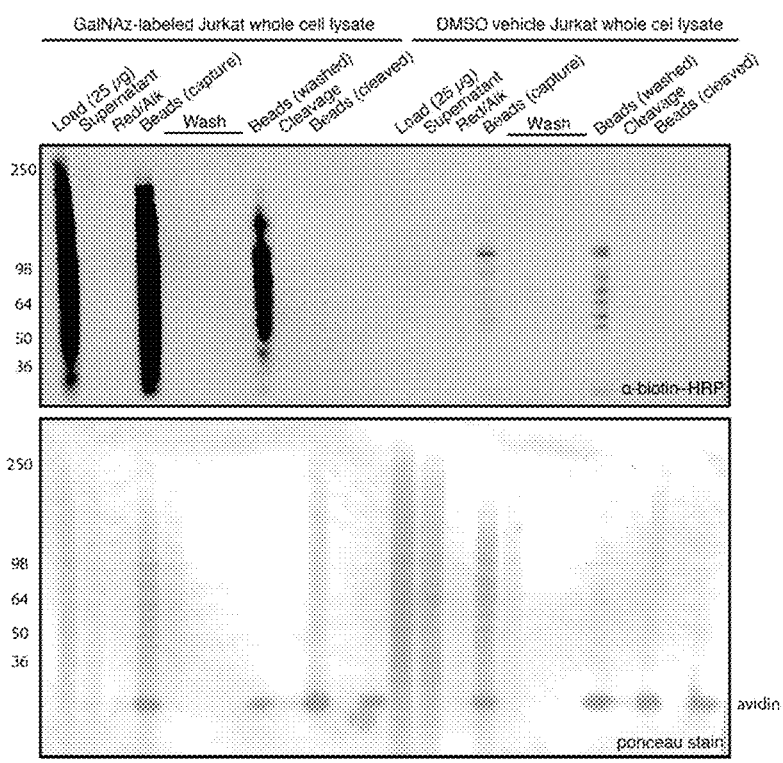

Fractionated Jurkat cell lysates were conjugated to probe 1 via CuAAC (FIG. 2A). Excess probe was removed by methanol precipitation, and proteins were resuspended in 1% rapigest in PBS. Glycoproteins were enriched by streptavidin-agarose affinity column, and enriched glycopeptides were trypsin digested on bead to release all non-conjugated peptides for glycoprotein identification. To release the glycopeptide, beads were treated with 2% formic acid, and the efficiency of glycoprotein capture and release was assessed by western blot (FIG. 6). The released glycopeptides were analyzed by reversed-phase nanoflow liquid chromatography coupled to a Thermo LTQ-Orbitrap XL mass spectrometer. Any mass spectrometer that achieves isotopic resolution (e.g., Q-tof) may also be used.

Figure 2B:
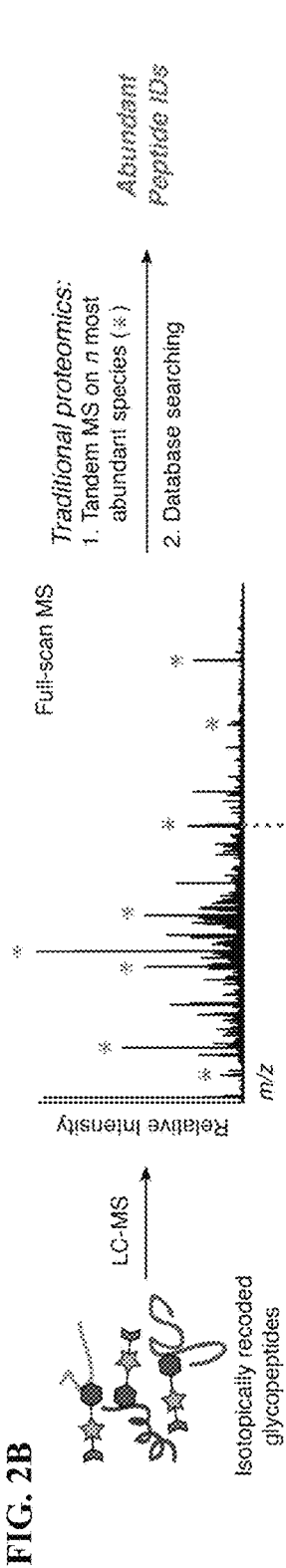
Figure 2C:
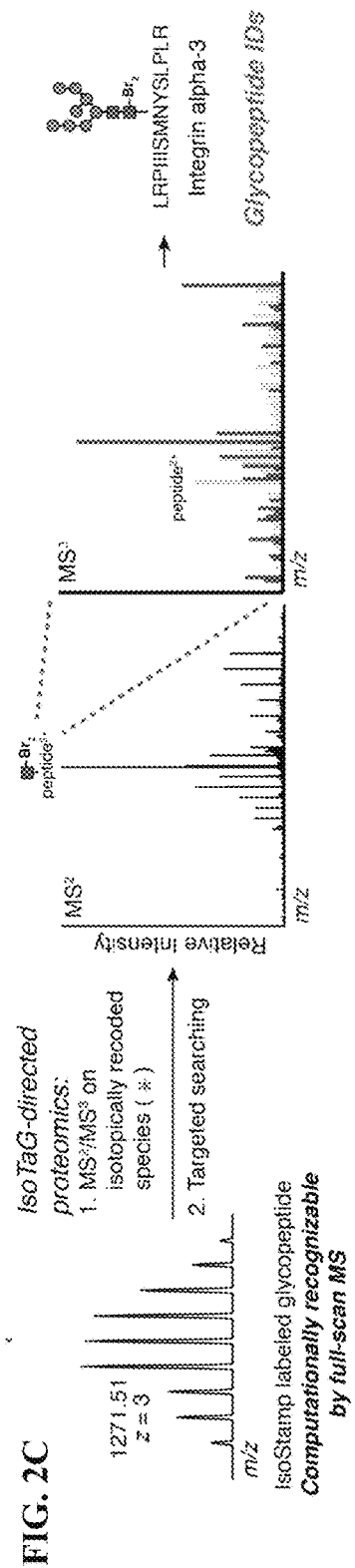

In traditional proteomics approaches, tandem MS is performed on the most abundant species in the full scan mass spectra to the exclusion of lower abundance species (FIG. 2B). By contrast, IsoTaG enables mass independent, targeted glycoproteomics (FIG. 2C). Glycopeptides displaying the isotope signature are computationally detected by the IsoStamp pattern-searching algorithm, which produces an inclusion list of m/z values and retention times for ions bearing isotopically recoded envelopes. The glycopeptides are subsequently analyzed by inclusion list-driven tandem MS, wherein tandem MS is exclusively performed on precursor ions on the inclusion list.

Figure 7:
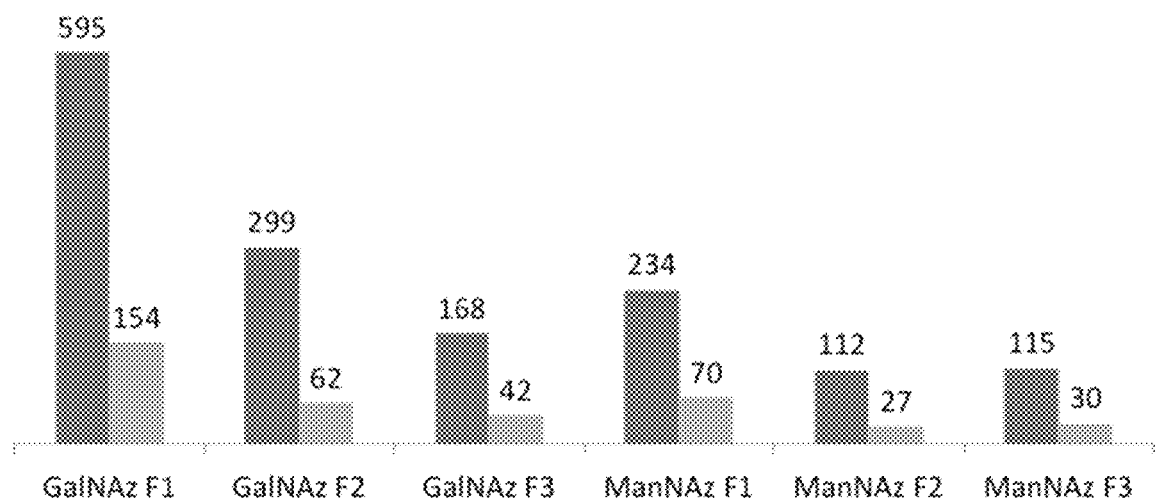
FIG. 7 illustrates that an IsoStamp-directed glycoproteomic method can select isotopically recoded species at a four-fold higher rate across fractions and glycan-type from Jurkat cell lysates. Jurkat cells were labeled with 100 μM Ac4GalNAz or Ac4ManNAz for 48 h. Media (F1), soluble (F2), and insoluble (F3) cellular fractions were enriched for isotopically recoded glycopeptides and analyzed by MS. Tandem MS was collected with an inclusion list (targeted) or by data dependent analysis on the top 6 peaks (untargeted).
Figure 8:
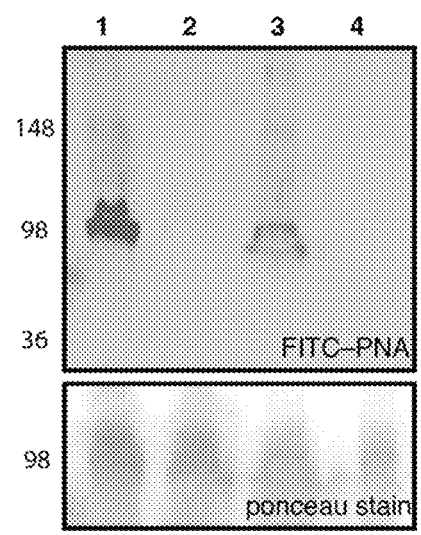
FIG. 8 provides an illustration that media from Jurkat cells display core 1 O-glycans. Media from Jurkat cells metabolically labeled with 100 μM Ac$_4$GalNAz or DMSO vehicle was treated with neuraminidase and analyzed by staining with FITC-PNA that detects the core 1 O-glycan. Ponceau staining shows equal protein loading (20 μg per lane). Lane 1: GalNAz-labeled Jurkat media+neuraminidase. Lane 2: GalNAz-labeled Jurkat media-neuraminidase. Lane 3: DMSO treated Jurkat media+neuraminidase. Lane 4: DMSO treated Jurkat media-neuraminidase.
Figure 9A:
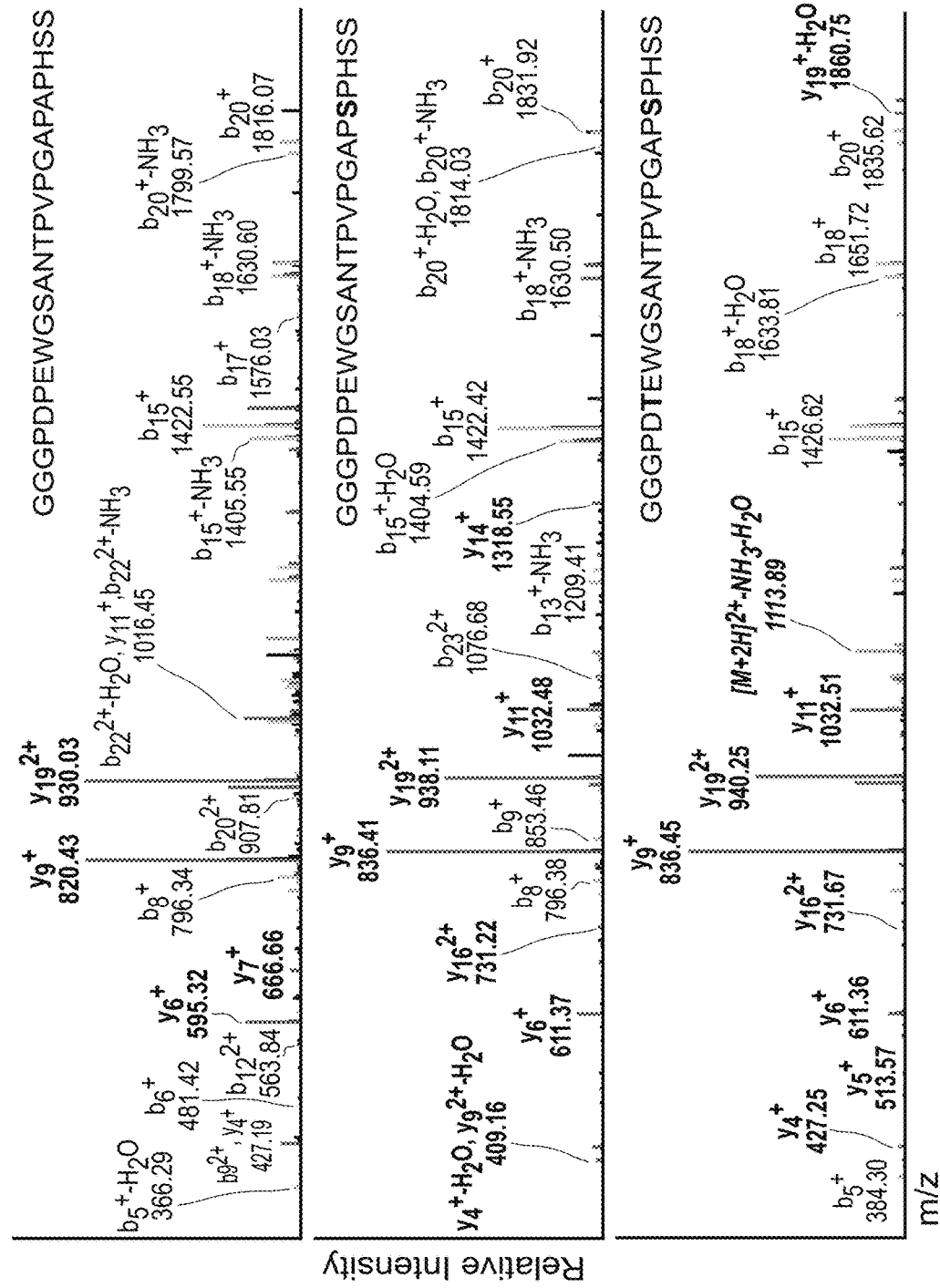
FIG. 9A-9C show assigned spectra from peptide isoforms identified from ManNAz-labeled PC-3 cells from: (A) prostate-specific microseminoprotein (Q1L6U9), (B) Glucosidase 2 subunit beta (P14314), and (C) Dickkopf-related protein 1 (O94907). Amino acid substitutions are bolded red. Spectra were assigned with Byonic as a node in Proteome Discoverer. The depicted sequences in FIG. 9(A) are GGG-PDPEWGSANTPVPGAPAPHSS (SEQ ID NO: 54), GGG-PDPEWGSANTPVPGAPSPHSS (SEQ ID NO: 55), GGG-PDTEWGSANTPVPGAPSPHSS (SEQ ID NO: 56). GGGPDPEWGSANTTVPGAPSPHSS (SEQ ID NO: 57) and GGGPDPEWGSSNTPVPGSPSPHSS (SEQ ID NO: 58). The depicted sequences in FIG. 9(B) are SEALPTDL-PAPSAPDLTEPK (SEQ ID NO: 34) and SEALPT-DLPTPSAPDLTEPK (SEQ ID NO: 35). The depicted sequences in FIG. 9(C) are NLPPPLGGAAGHPG-SAVSAAPGILYPGGNK (SEQ ID NO: 28) and NLPPPLG-GAAGHPGSSVSAAPGILYPGGNK (SEQ ID NO: 66).
Figure 9A:
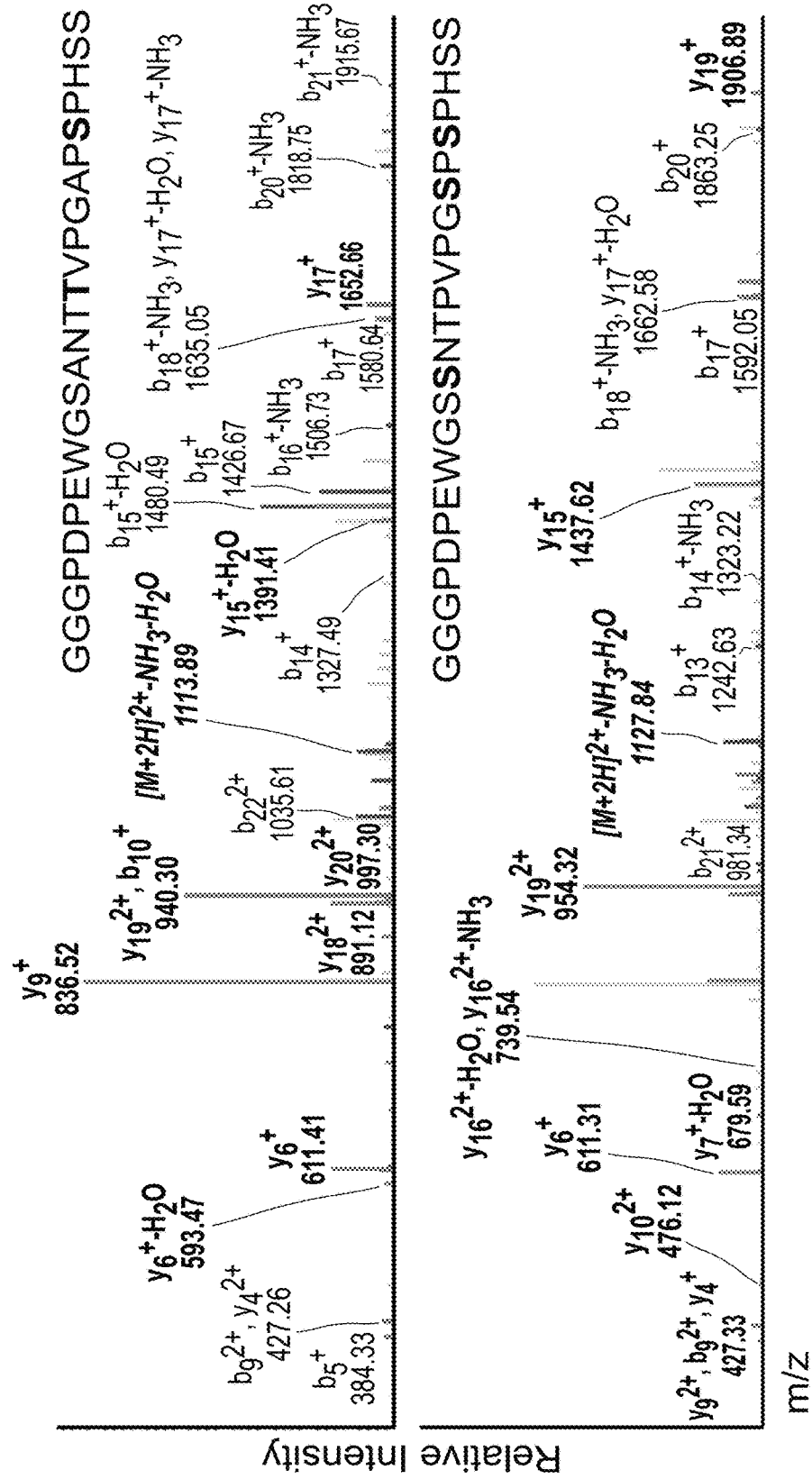
Figure 9B:
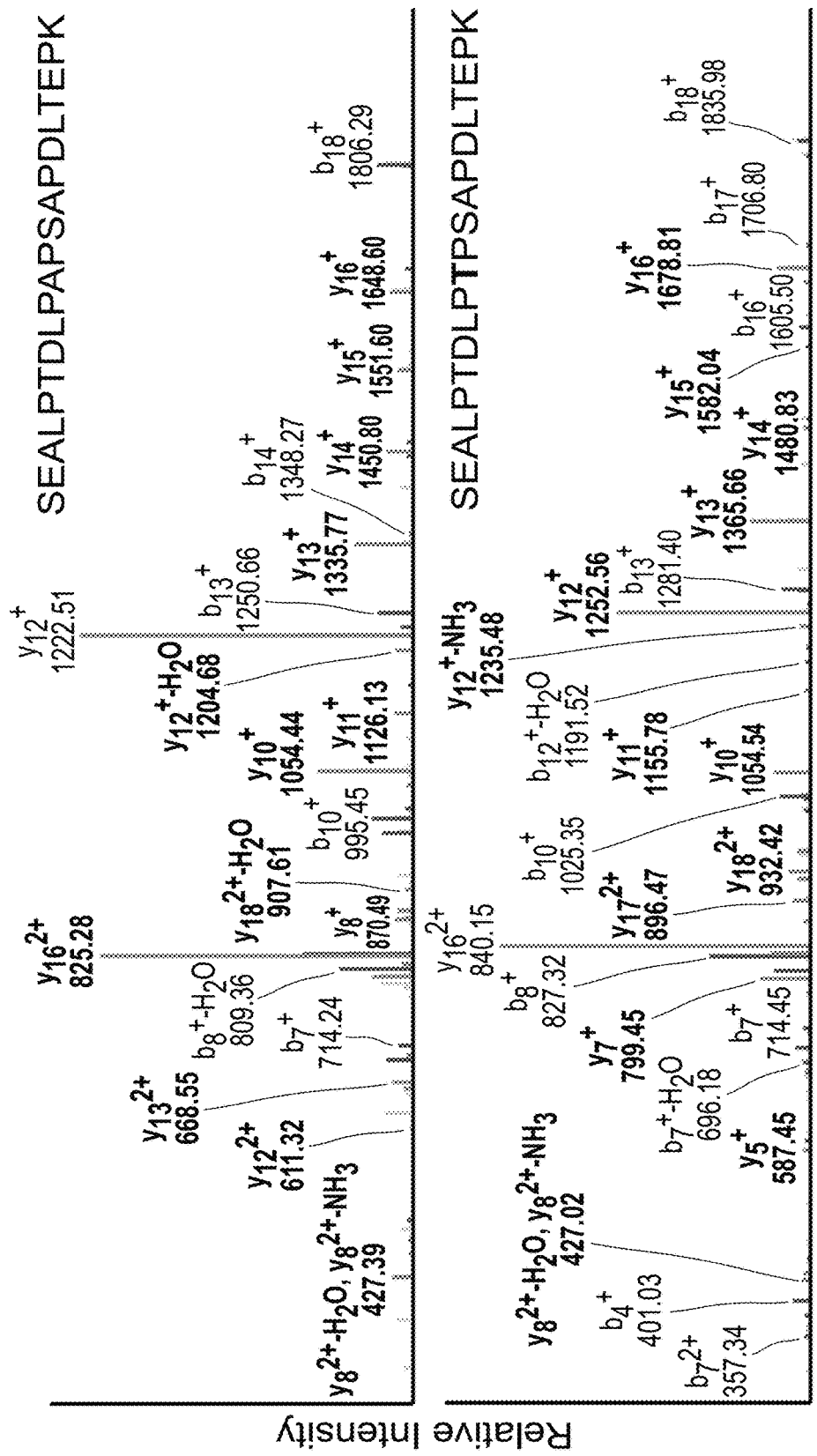
Figure 9C:
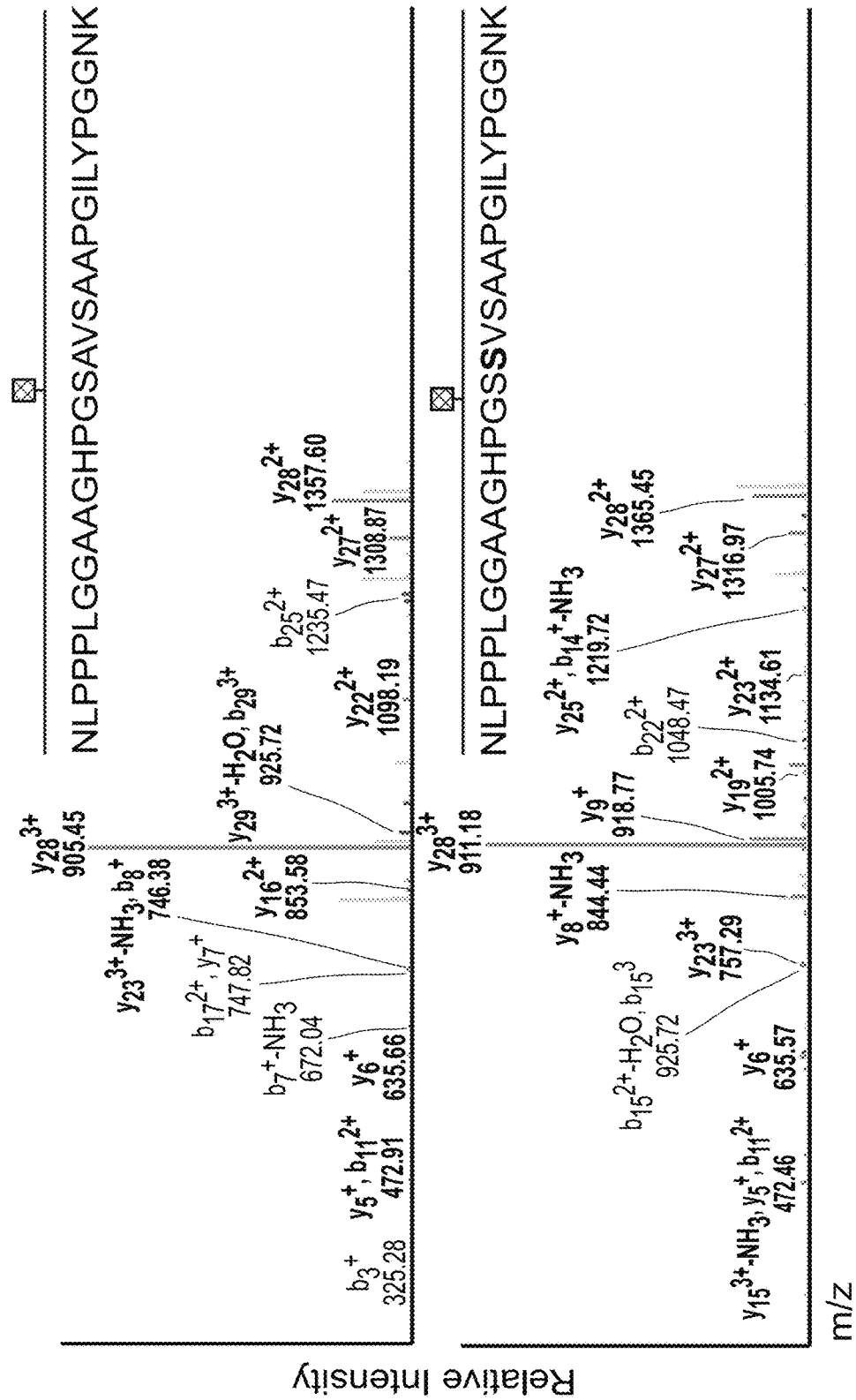
Figure 10A:
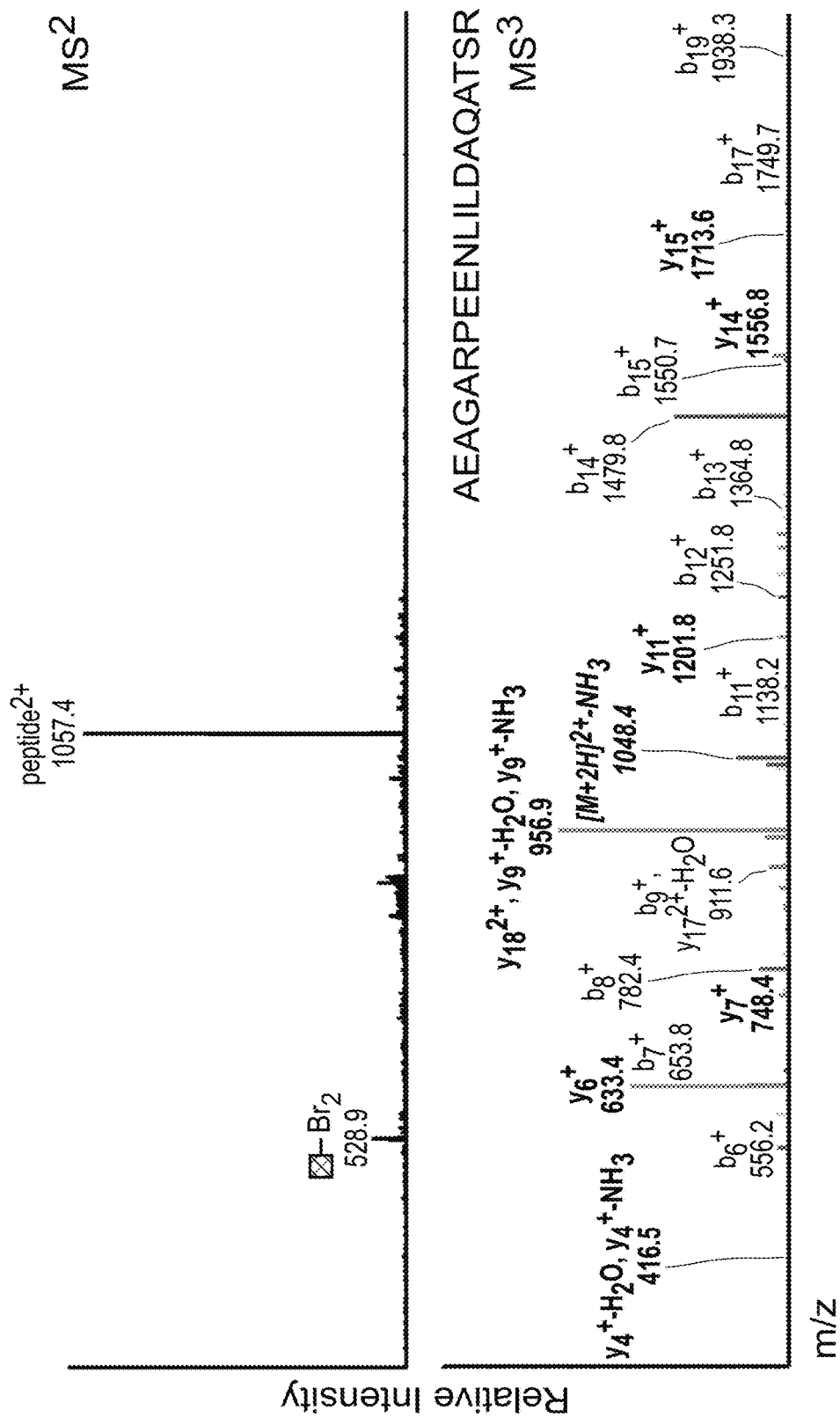
FIG. 10A-10C show exemplary assignments by CID for glycopeptides from MS2 and MS3 spectra for O-GalNAz (a), bis-sialylated O8 (b), and N-glycan N5 (c) glycoforms. The tagged glycan is denoted with "$Br_2$." The metabolically labeled glycan (but not tagged) is denoted with "N3." The depicted sequence in FIG. 10(A) is AEAGARPEEN-LILDAQATSR (SEQ ID NO: 67). The depicted sequence in FIG. 10(B) is GGGPDPEWGSANTPVPGAPAPHSS (SEQ ID NO: 54). The depicted sequence in FIG. 10(C) is LRPII-ISMNYSLPLR (SEQ ID NO: 36).
Figure 10B:
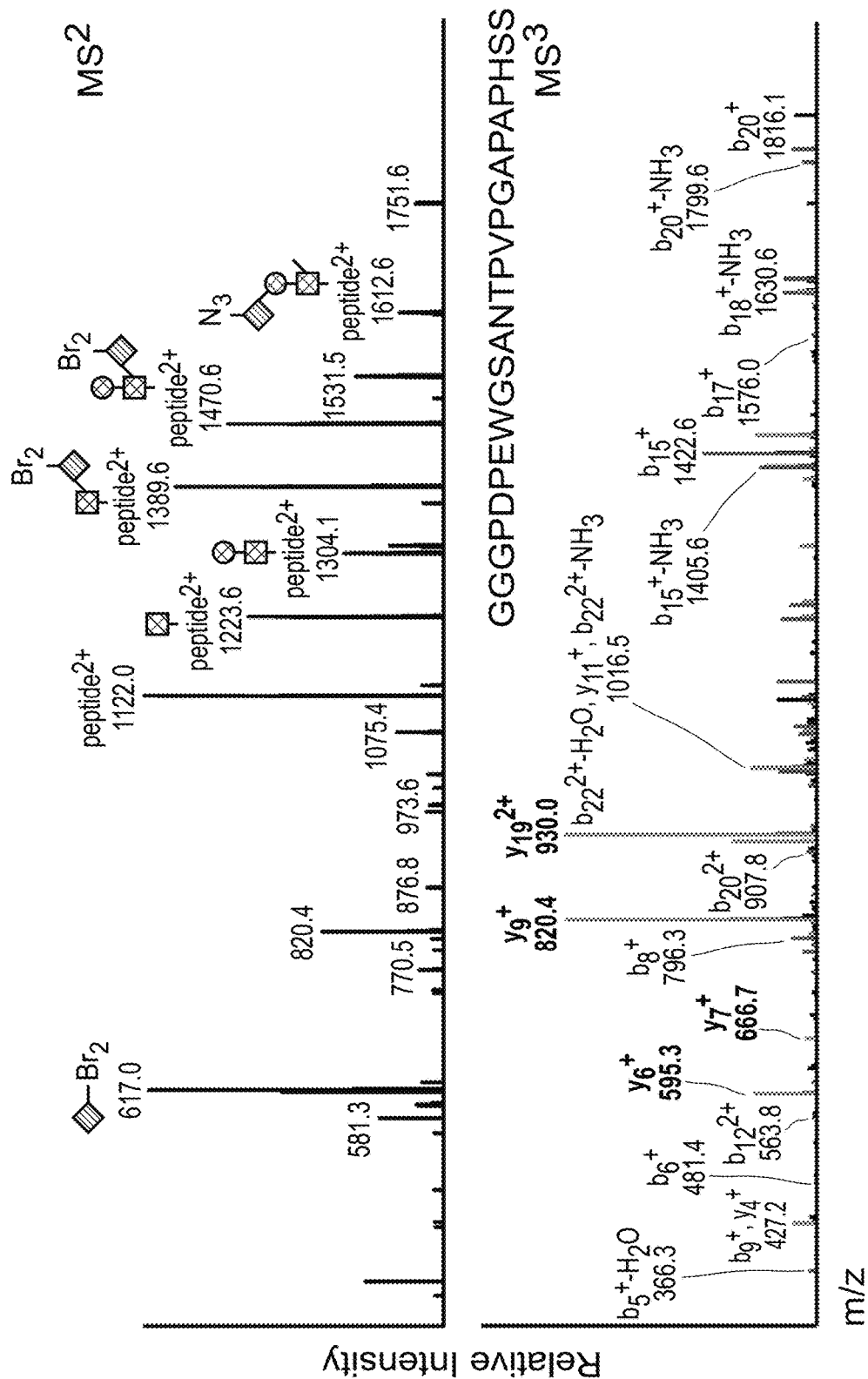
Figure 10C:
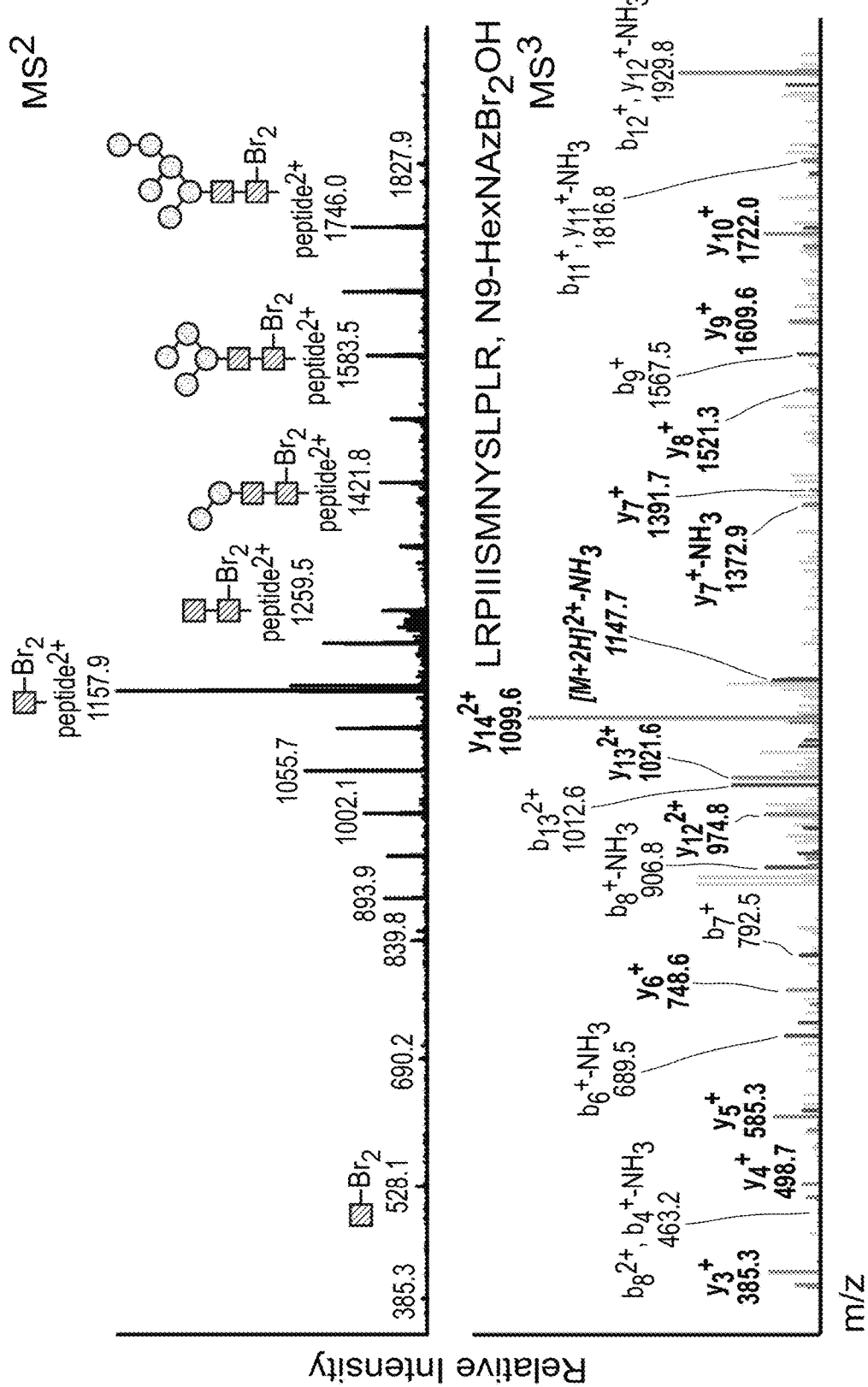

To quantify the advantage of IsoStamp-directed glycoproteomics, a series of back-to-back runs were performed with and without the inclusion list and evaluated the total number of isotopically recoded species selected for tandem MS. A four-fold improvement in tagged glycopeptides selected for tandem MS was observed across all fractions and glycan types (FIG. 7). Over 1000 isotopically recoded species were selected for tandem MS from GalNAz-labeled Jurkat cell lysates using the inclusion list, as compared to 260 without, indicating that IsoTaG effectively targets low abundance species, and mitigates the need for extensive fractionation, mass spectrometer analysis, and computation time. The enrichment, data collection, and initial computation for one cell type as described above were performed in three days.

To demonstrate the broad applicability of the chemical glycoproteomics platform, the enrichment procedure was repeated with PC-3 and MCF-7 cell lines. Due to an interest in identifying low abundance glycopeptides, tandem MS was performed using collision-induced dissociation (CID) to achieve the highest sensitivity. FIG. 2C illustrates the identification of an N-glycoprotein from GalNAz-labeled Jurkat lysates. Inclusion list-triggered tandem MS of an isotopically recoded precursor ion generates a tandem mass ($MS^2$) spectrum for identification of glycan structure from charged and neutral losses. Subsequent data-dependent CID of the three most intense ions in the $MS^2$ spectrum generates $MS^3$ spectra for glycopeptide amino acid sequence identification by database searching.

Data analysis was performed with a combination of SEQUEST HT and Byonic algorithms and searched against the Swiss-Prot human proteome. Data were first filtered for $MS^2$ and $MS^3$ spectra from isotopically recoded precursor ions and searched using the SEQUEST HT algorithm within Proteome Discoverer software. Unassigned spectra were then searched in an iterative fashion using Byonic, a program specialized for the identification of glycopeptides. Finally, remaining unassigned glycopeptide spectra were searched with the corresponding glycoforms as a glycan modification against the UniprotKB human proteome. Glycans were assigned manually from the $MS^2$ and glycan structure inferred from the observed neutral or charged losses. All assignments were validated for isotopic distribution, exact mass (Δmass <5 ppm), charged or neutral loss of the glycan, and peptide fragment ions. No precursor overlap between assigned glycopeptides and samples derived from the DMSO control were found. In aggregate, over 550 intact N-linked and O-linked glycopeptides from 240 glycoproteins were identified, of which 220 peptides and 120 proteins that have not been previously identified as glycosylated.

TABLE 1

Representative glycopeptides and associated glycoforms identified using IsoTaG. Peptide isoforms (i.e., peptide sequence polymorphisms, pSPs) are bolded. Glycosites (N-glycan) are underlined. Multiple glycosites are denoted by "M".

| Accession | Protein (Gene Name) | Peptide | Glycan Isoform |
|---|---|---|---|
| O00468 | Agrin (AGRN) | NLEEVEFCVEDKPGTHFTPVPPTPPDACR (SEQ ID NO: 25) | O2, O5, O6 |
| O94907 | Dickkopf-related protein 1 (DKK1) | GEIEETITESFGNDHSTLDGYSR (SEQ ID NO: 26) | O7 |
| | | MYHTKGQEGSVCLR (SEQ ID NO: 27) | O6, O7 |
| | | NLPPPLGGAAGHPGSAVSAAPGILYPGGNK (SEQ ID NO: 28) | O6, O7 |
| | | NLPPPLGGSAGHPGSAVSAAPGILYPGGNK (SEQ ID NO: 29) | O6, O7 |
| | | YQTIDNYQPYPCAEDEECGTDEYCASPTR (SEQ ID NO: 30) | O6, O7 |
| P02786 | Transferrin receptor protein 1 (TFRC) | LAGTESPVREEPGEDFPAAR (SEQ ID NO: 31) | O2, O5, O6, O8 |
| P07339 | Cathepsin D (CTSD) | YSQAVPAVTEGPIPEVLK (SEQ ID NO: 32) | O6, O7 |
| P07602 | Prosaposin (PSAP) | LPALTVHVTQPK (SEQ ID NO: 33) | O2, O6 |
| P14314 | Glucosidase 2 subunit beta (PRKCSH) | SEALPTDLPAPSAPDLTEPK (SEQ ID NO: 34) | O2, O6, O7 |
| | | SEALPTDLPTPSAPDLTEPK (SEQ ID NO: 35) | O2, O4, O6, O7 |
| P26006 | Integrin alpha-3 (ITGA3) | LRPIIISM<u>N</u>YSLPLR (SEQ ID NO: 36) | N4 |
| P26572 | Alpha-1,3-mannosyl-glycoprotein 2-beta-N-acetylglucosaminyltransferase (MGAT1) | GRVPTAAPPAQPR (SEQ ID NO: 37) | O6, O7 |
| | | VPVTPAPAVIPILVIACDR (SEQ ID NO: 38) | O7 |
| P27824 | Calnexin (CANX) | HDGHDDDVIDIEDDLDDVIEEVEDSKPDTTAPPSSPK (SEQ ID NO: 39) | O6, O7 |
| | | VTYKAPVPTGEVYFADSFDR (SEQ ID NO: 40) | O2, O4, M |
| P42785 | Lysosomal Pro-X carboxypeptidase (PRCP) | ALGSLHLPTNPTSLPAVAK (SEQ ID NO: 41) | O2, O6 |
| P43026 | Growth/differentiation factor 5 (GDF5) | QATARTVTPK (SEQ ID NO: 42) | O2, O6, O7 |
| P46977 | Dolichyl-diphosphooligosaccharide--protein glycosyltransferase subunit STT3A (STT3A) | TILVD<u>N</u>NTWNNTHISR (SEQ ID NO: 43) | N4 |
| P51610 | Host cell factor 1 (HCFC1) | SGTVTVAQQAQVVTTVVGGVTK (SEQ ID NO: 44) | O1, M |
| | | TAAAQVGTSVSSATNTSTRPIITVHK (SEQ ID NO: 45) | O1, M |
| Q02818 | Nucleobindin-1 (NUCB1) | GAPNKEETPATESPDTGLYYHR (SEQ ID NO: 46) | O2, O6, O7, O8 |
| Q08629 | Testican-1 (SPOCK1) | VIKPTSSNTAQGR (SEQ ID NO: 47) | O6, O7 |
| Q12841 | Follistatin-related protein 1 (FSTL1) | SVSPSASPVVCYQSNR (SEQ ID NO: 48) | O2, O3, O6, O7 |

TABLE 1-continued

Representative glycopeptides and associated glycoforms identified using IsoTaG. Peptide isoforms (i.e., peptide sequence polymorphisms, pSPs) are bolded. Glycosites (N-glycan) are underlined. Multiple glycosites are denoted by "M".

| Accession | Protein (Gene Name) | Peptide | Glycan Isoform |
|---|---|---|---|
| Q14118 | Dystroglycan (DAG1) | DWENQLEASMHSVLSDLHEAVPTVVGIPDGTAVVGR (SEQ ID NO: 49) | O6, O7 |
| Q14242 | P-selectin glycoprotein ligand 1 (SELPLG) | GLFIPFSVSSTHK (SEQ ID NO: 50) | O2, O4, M |
| Q14766 | Latent-transforming growth factor beta-binding protein 1 (LTBP1) | EHGPGVAEPEVATAPPEKEIPSLDQEK (SEQ ID NO: 51) | O7 |
|  |  | IKVVFTPSICK (SEQ ID NO: 52) | O7 |
|  |  | STHPPPLPAKEEPVEALTFSR (SEQ ID NO: 53) | O6 |
| Q1L6U9 | Prostate-associated microseminoprotein (MSMP) | GGGPDPEWGSANTPVPGAPAPHSS (SEQ ID NO: 54) | O6, O7 |
|  |  | GGGPDPEWGSANTPVPGAPSPHSS (SEQ ID NO: 55) | O6, O7, O8 |
|  |  | GGGPDTEWGSANTPVPGAPSPHSS (SEQ ID NO: 56) | O6, O7, O8 |
|  |  | GGGPDPEWGSANTTVPGAPSPHSS (SEQ ID NO: 57) | O6 |
|  |  | GGGPDPEWGSSNTPVPGSPSPHSS (SEQ ID NO: 58) | O7 |
| Q8NBS9 | Thioredoxin domain-containing protein 5 (TXNDC5) | DFQTLENWMLQTLNEEPVTPEPEVEPPSAPELK (SEQ ID NO: 59) | O2, O6 |
| Q8NCH0 | Carbohydrate sulfotransferase 14 (CHST14) | AGAGPSPAGDDVTFPEFLR (SEQ ID NO: 60) | O2, O6 |
| Q8TCJ2 | Dolichyl-diphosphooligosaccharide--protein glycosyltransferase subunit STT3B (STT3B) | TTLVDN̲NTWNNSHIALVGK (SEQ ID NO: 61) | N2, N3, N4 |
|  |  | TTLVDNNTWN̲NSHIALVGK (SEQ ID NO: 61) | N2, N3, N4 |
| Q92854 | Semaphorin-4D (SEMA4D) | VVPKPVVAPTLSVVQTEGSR (SEQ ID NO: 62) | O2, O6, M |
| Q92896 | Golgi apparatus protein 1 (GLG1) | EPENEISSDCNHLLWNYK (SEQ ID NO: 63) | O2, O7 |
| Q9NTZ6 | RNA-binding protein 12 (RBM12) | VNLPTTVSNFNNPSPSVVTATTSVHESNK (SEQ ID NO: 64) | O1, M |
| Q9Y4L1 | Hypoxia up-regulated protein 1 (HYOU1) | N̲ATLAEQAK (SEQ ID NO: 65) | N3, N4 |

Figure 4A:
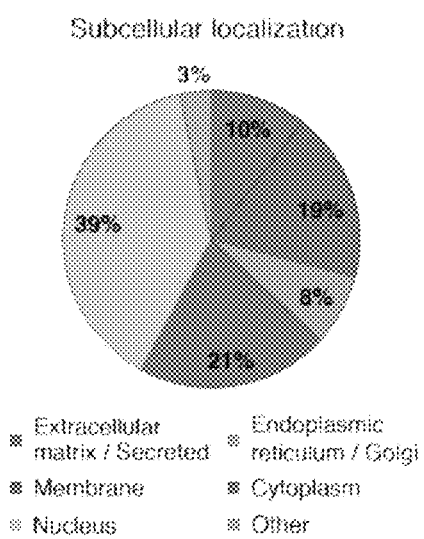
FIG. 4A-4D illustrate the distribution of identified glycopeptides: (a) Glycoproteins identified via IsoTaG are distributed throughout the cell; and (b) Glycopeptides identified via IsoTaG are highly cell specific. Data for all characterized glycopeptides were combined. Glycopeptides identified via chemical glycoproteomics: (c) frequency of observed peptides bearing N-glycans; and (d) frequency of observed peptides bearing O-glycans.
Figure 4B:
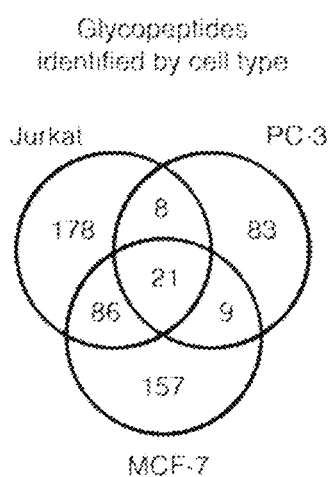
Figure 4C:
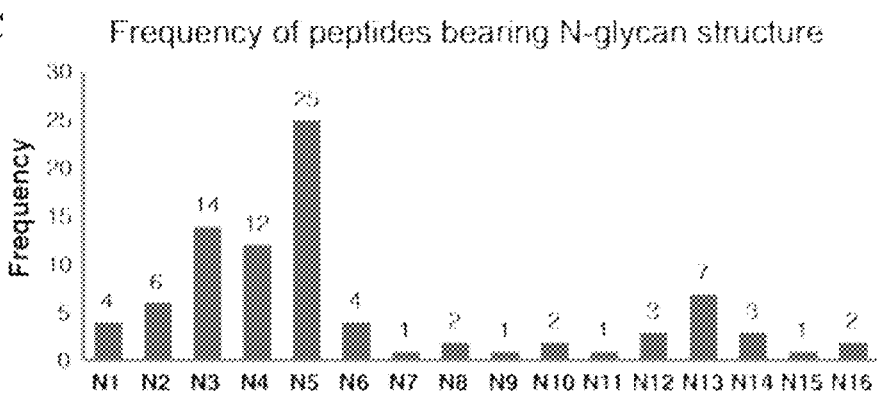
Figure 4D:
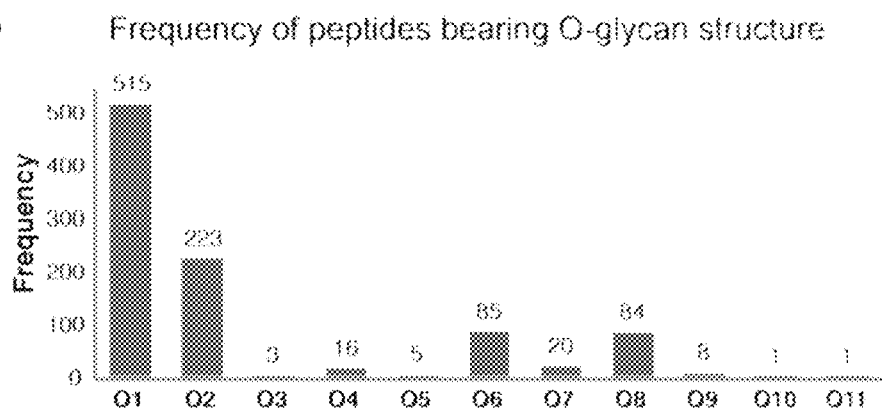

Representative intact glycopeptides identified with multiple glycoforms are presented in Table 1. A high degree of glycoform variation was found in elaborated glycopeptides. Analysis of subcellular localization reveals a distribution of nuclear, cytoplasmic, and membrane or secreted glycoproteins identified in this study (FIG. 3A). Sixteen N-glycopeptide glycoforms were identified (representative structures N1-N16, FIG. 3a), covering the entire N-glycan biosynthetic pathway, in which immature and high mannose structures were relatively predominant. The lower identification rate of elaborated N-glycopeptides, including sialylated structures, may reflect hindered access of probe 1 (i.e., when the metabolic label resides on the core GlcNAc), difficult elucidation by MS, or reduced ionization efficiency. Alternatively, metabolically labeled immature N-glycans may be more abundant than elaborated N-glycans in the samples evaluated. Identified O-glycan types corresponded to O-GlcNAc (O1), Tn (O2), STn (O5), Core 3 (O4), Core 1 (O3), sialylated glycans (O6, O7, O8, O9), as well as Core 4 (O10), and Core 2 (O11)O-glycans (FIG. 3b). The preponderance of O-GlcNAcylated peptides shown in FIG. 4d reflects, at least in part, the efficiency of the GALE epimerase to biosynthesize UDP-GlcNAz from Ac4GalNAz. (FIG. 3b). Fragmentation of the glycan occurs prior to fragmentation of the peptide backbone with CID, enabling the assignment of glycan structure, but not the underlying peptide, for several of the elaborated glycopeptides (orange peptides, FIG. 3b). While electron transfer dissociation (ETD) is an orthogonal fragmentation method for peptides bearing CID-labile PTMs, it was found that halogenated glycopeptides have low ETD fragmentation efficiency. The mucin type O-glycans identified were predominantly various sialylation states of core 1 O-glycans from PC-3 and MCF-7 cell lines. Jurkat cells displayed highly heterogeneous O-glycopeptides due to the knockdown of core 1 O-glycan elaboration via truncation of the COSMC chaperone. Notably, core 1 O-glycans from Jurkat cells were still identified, as truncated COSMC maintains 2-5% activity of the full-length protein. The presence of Core 1 glycoforms in the conditioned media from Jurkat cells was confirmed by lectin staining (FIG. 7).

Despite the targeted tandem MS analysis, approximately 40% of isotopically recoded spectra remained unassigned from database searching alone. In some cases spectral non-assignment was related to low signal-to-noise ratios of fragment ions, the presence of unidentified modifications (e.g., non-glycan fragments and copper-click related off-target reactivity), or semi-specific cleavage. Nonetheless, in several spectra derived from glycopeptides, database searching against the UniprotKB human proteome did not reveal confident assignment on visual inspection.

Figure 5:
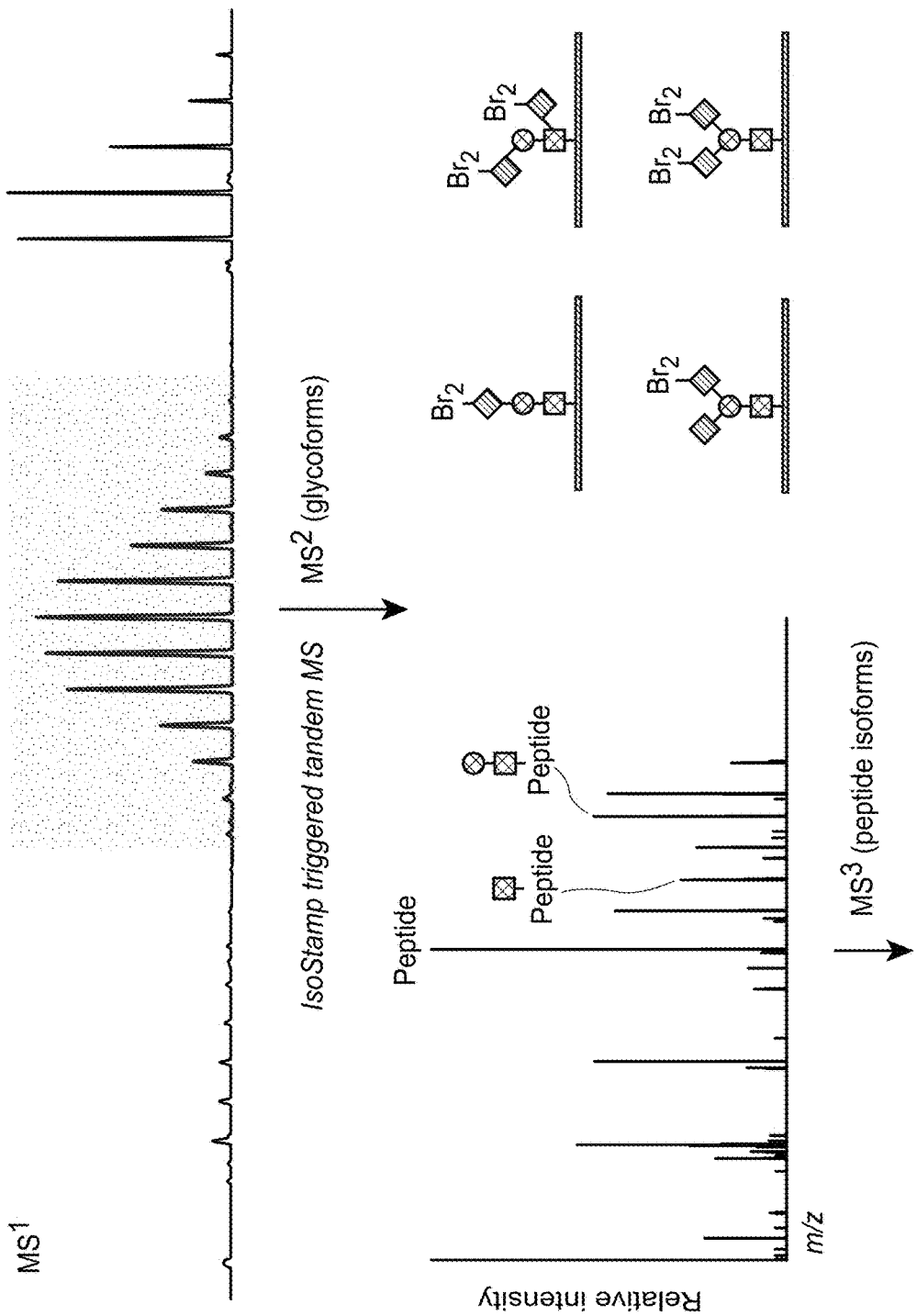
FIG. 5 illustrates a targeted analysis of isotopically recoded glycopeptides that reveals both glycan and peptide isoforms. The novel O-glycopeptide from prostate-associated microseminoprotein was found as four glycan isoforms by MS2 and six peptide isoforms by MS3. The tagged glycan is denoted with "Br$_2$". Amino acid isoforms are bolded red. The depicted sequences are GGGPDPEWG-SANTPVPGAPAPHSS (SEQ ID NO: 54), GGGPDPEWG-SANTPVPGAPSPHSS (SEQ ID NO: 55) and GGGP-DTEWGSANTPVPGAPSPHSS (SEQ ID NO: 56).
Figure 5:
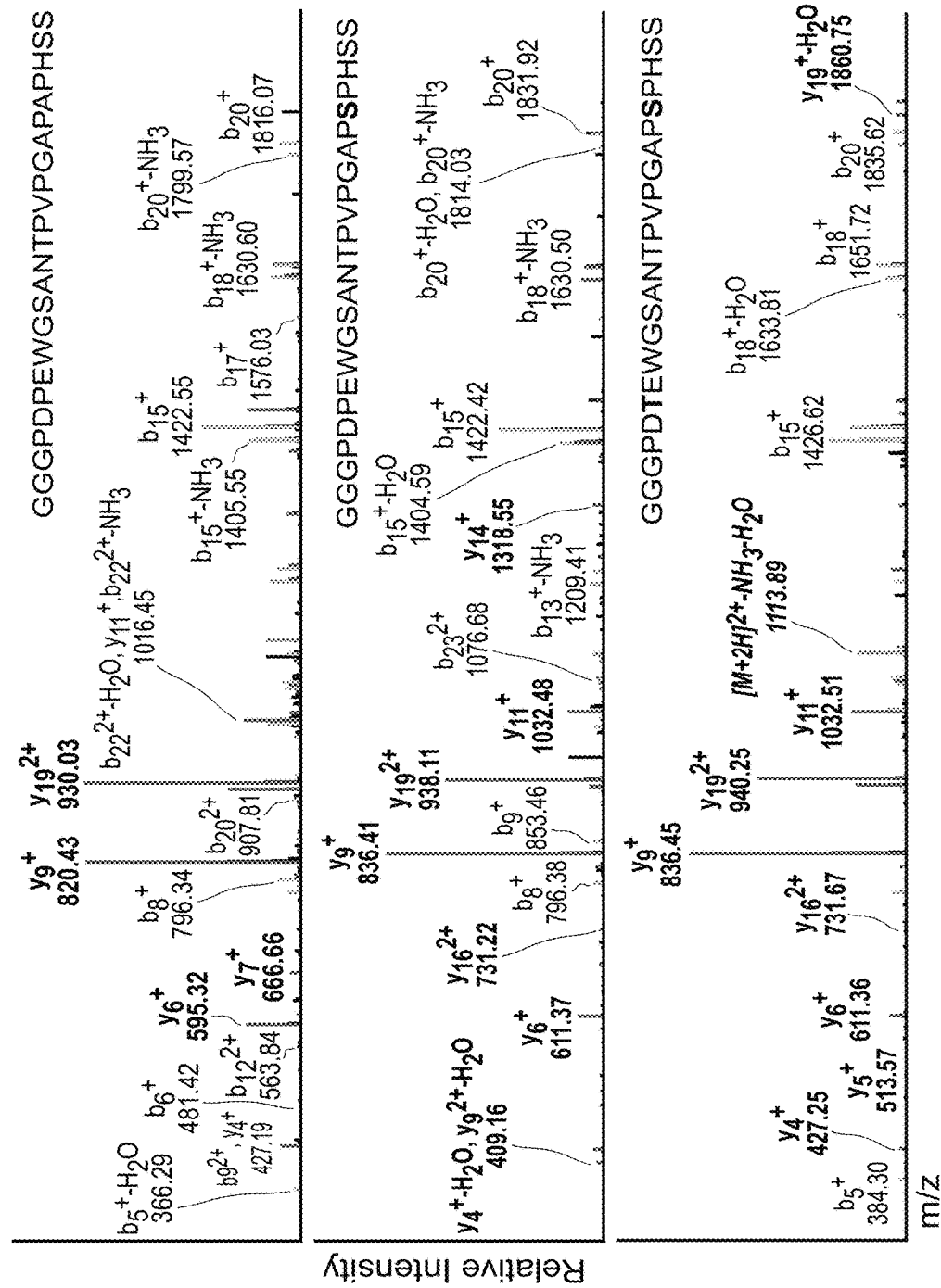

It was suspected that the correct peptide amino acid sequences were not in the protein database for these tandem MS spectra. To investigate this possibility, an additional data set was collected on the PC-3 ManNAz-labeled cell lysate, with MS1 and MS2 spectra measured in the Orbitrap analyzer to obtain high resolution measurement of both precursor and fragment ions. Targeted analysis of this data set revealed 21 glycopeptides carrying sequence polymorphisms that were not present in the protein database (UniprotKB), and one sequence polymorphism observed by genetic sequencing. FIG. 5 illustrates the identification of novel O-glycopeptides derived from prostate-associated microseminoprotein. A total of 15 isoforms were identified across four glycan and six peptide isoforms. Additional peptide isoforms from prostate-associated microseminoprotein and two other glycoproteins were observed (FIG. 9).

Example 7: Quantitative Methods

Cleavable probes that include deuterium isotopic labels are prepared as described in FIG. 11. A desired IsoTaG signature is prepared by mixing a suitable molar ratio of the +0, +2, +4 and +6 probes.

FIG. 12 illustrates a quantitative method of determining glycopeptide and glycoform levels and peptide and protein levels in sample of interest. Quantitative glycoproteomics can determine whether fluctuations in particular glycoproteins are reflective of changes in the proteome or the glycome, by using IsoTaG for identification of intact glycopeptides, and separate quantitation of the glycan and the peptide. Samples for comparison (e.g., normal vs. cancer) are labeled with a light or heavy (i.e., isotopically labelled) glycan, respectively. Differential metabolic tagging generates isotopically recoded glycopeptides with a, e.g., 7 Da window between light and heavy samples—providing for relative quantitation of the glycoform. Simultaneous introduction of cysteine protein-labeling uses an orthogonal chemistry for quantitative proteomics of glycoproteins. This approach provides the precise measurement of both the glycome and proteome.

Using the subject methods, the light sample is labelled with $Ac_4GAlNAz$-0, IsoTag cleavable probe-0 and cysteine label-0, and the heavy sample is labelled with $Ac_4GAlNAz$-3, IsoTag cleavable probe-6 and cysteine label-5. It is understood that the designation "0", "3", "6" and "5" refers to the type of isotopic or mass label that is utilized in each of the labelling reagents. Mixing of 1:1 ratio of the light and heavy samples followed by chemical enrichment, proteolysis and mass spectroscopic analysis leads to a quantitative analysis of the glycoprotein content compared with the protein content of the samples.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A cleavable probe of Formula (I):

A-L-(M-Z)  (I)

wherein:
A is an affinity tag;
L is a cleavable linker;
M is an isotopic label of the formula —(CH$_2$)$_p$—CH(Br)=CH(Br)—(CH$_2$)$_q$— wherein p and q are each independently 0-6; and
Z is a chemoselective tag comprising an alkyne.

2. The probe of claim 1, wherein A is a biotin moiety.

3. The probe of claim 1, wherein L is described by the formula:

L$^1$-X-L$^2$- wherein L$^1$ and L$^2$ are optional linkers and X is a cleavable group.

4. The probe of claim 1, wherein X is —O—Si(R)$_2$—O—, wherein each R is independently selected from hydrogen, an aryl, a substituted aryl, an alkyl and a substituted alkyl.

5. The probe of claim 1, wherein L is a cleavable silane linker.

6. The probe of claim 1, wherein the probe has the formula A-L-M-Z, wherein:
A is a biotin moiety;
L is -(PEG)$_n$—NH—(CH$_2$)$_m$—C(CH$_3$)$_2$—O—Si(R)$_2$—O—;
M is —(CH$_2$)$_p$—CH(Br)=CH(Br)—(CH$_2$)$_q$—; and
Z is an alkyne-containing group,
wherein n and m are each independently 0-20 and p and q are each independently 0-6.

7. The probe of claim 1, wherein M comprises two or more deuterium atoms.

8. The probe of claim 1, wherein M comprises a mixture of components, each component independently comprising 0, 2, 4 or 6 deuterium atoms.

9. A kit, comprising:
a cleavable probe of Formula (I):

A-L-(M-Z)  (I)

wherein:
A is an affinity tag;
L is a cleavable linker;
M is an isotopic label of the formula —(CH$_2$)$_p$—CH(Br)=CH(Br)—(CH$_2$)$_q$— wherein p and q are each independently 0-6; and
Z is a chemoselective tag comprising an alkyne; and
one or more components selected from: an enzyme, a chemical cleavage agent, a light source, a buffer, a cell, a metabolically tagged protein and a tagged sugar.

10. The probe of claim 1, wherein the alkyne comprises acetylene or a cyclooctyne.

11. The probe of claim 1, wherein the probe of formula (I) is

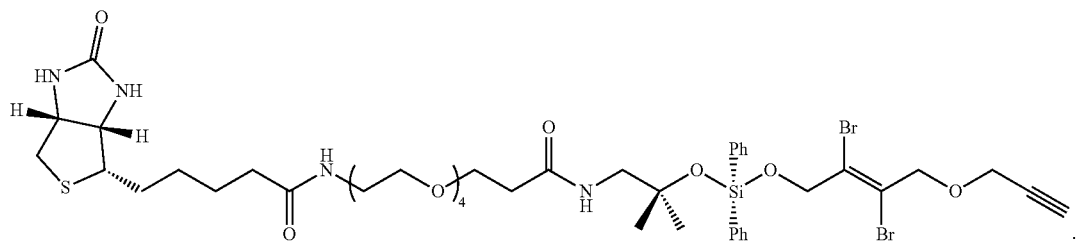

12. The kit of claim 9, wherein the metabolically tagged protein is a glycosylated protein comprising an azide-tagged sugar.

13. The kit of claim 12, wherein the azide-tagged sugar is selected from the group consisting of N-azidoacetylgalactosamine, acetylated (Ac4GalNAz); N-azidoacetylglucosamine, acetylated (Ac4GlcNAz); and N-azidoacetylmannosamine, acetylated (Ac4ManNAz).

14. The kit of claim 12, wherein the azide-tagged sugar comprises an isotopic label.

15. The probe of claim 1, wherein M is described by the formula:

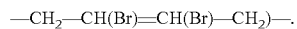
—CH$_2$—CH(Br)=CH(Br)—CH$_2$—.

16. The kit of claim 9, wherein M is described by the formula:

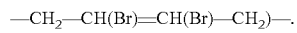
—CH$_2$—CH(Br)=CH(Br)—CH$_2$—.

17. The kit of claim 9, wherein the alkyne comprises acetylene or a cyclooctyne.

* * * * *

SEQUENCE LISTING

<160> NUMBER OF SEQ ID NOS: 67

<210> SEQ ID NO 1
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is Leu or Gln

<400> SEQUENCE: 1

Pro Xaa Gly Met Thr Ser
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE

```
<222> LOCATION: (2)..(2)
<223> OTHER INFORMATION: X is Leu or Gln

<400> SEQUENCE: 2

Pro Xaa Gly Met Thr
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 3

Cys Gly Leu Val Pro Ala Gly Ser Gly Pro
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 4

Ser Leu Leu Lys Ser Arg Met Val Pro Asn Phe Asn
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 5

Ser Leu Leu Ile Ala Arg Arg Met Pro Asn Phe Asn
1               5                   10

<210> SEQ ID NO 6
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 6

Ser Lys Leu Val Gln Ala Ser Ala Ser Gly Val Asn
1               5                   10

<210> SEQ ID NO 7
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 7

Ser Ser Tyr Leu Lys Ala Ser Asp Ala Pro Asp Asn
1               5                   10

<210> SEQ ID NO 8
<211> LENGTH: 12
<212> TYPE: PRT
<213> ORGANISM: Artificial sequence
<220> FEATURE:
```

<223> OTHER INFORMATION: Synthetic polypeptide

<400> SEQUENCE: 8

Arg Pro Lys Pro Gln Gln Phe Phe Gly Leu Met Asn
1               5                   10

<210> SEQ ID NO 9
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 9

Ser Leu Arg Pro Leu Ala Leu Trp Arg Ser Phe Asn
1               5                   10

<210> SEQ ID NO 10
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 10

Ser Pro Gln Gly Ile Ala Gly Gln Arg Asn Phe Asn
1               5                   10

<210> SEQ ID NO 11
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 11

Asp Val Asp Glu Arg Asp Val Arg Gly Phe Ala Ser Phe Leu
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 12

Ser Leu Pro Leu Gly Leu Trp Ala Pro Asn Phe Asn
1               5                   10

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 13

Ser Leu Leu Ile Phe Arg Ser Trp Ala Asn Phe Asn
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 14

Ser Gly Val Val Ile Ala Thr Val Ile Val Ile Thr
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 15

Ser Leu Gly Pro Gln Gly Ile Trp Gly Gln Phe Asn
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 16

Lys Lys Ser Pro Gly Arg Val Val Gly Gly Ser Val
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 17

Pro Gln Gly Leu Leu Gly Ala Pro Gly Ile Leu Gly
1               5                   10

<210> SEQ ID NO 18
<211> LENGTH: 31
<212> TYPE: PRT
<213> ORGANISM: Artificial sequence
<220> FEATURE:
<223> OTHER INFORMATION: Synthetic polypeptide

<400> SEQUENCE: 18

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 19
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 19

Gly Pro Gln Gly Leu Ala Gly Gln Arg Gly Ile Val
1               5                   10

<210> SEQ ID NO 20
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 20

Gly Gly Ser Gly Gln Arg Gly Arg Lys Ala Leu Glu
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 21

Ser Leu Ser Ala Leu Leu Ser Ser Asp Ile Phe Asn
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 22

Ser Leu Pro Arg Phe Lys Ile Ile Gly Gly Phe Asn
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 23

Ser Leu Leu Gly Ile Ala Val Pro Gly Asn Phe Asn
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 24

Phe Phe Lys Asn Ile Val Thr Pro Arg Thr Pro Pro
1               5                   10

<210> SEQ ID NO 25
<211> LENGTH: 29
<212> TYPE: PRT
<213> ORGANISM: Artificial sequence
<220> FEATURE:
<223> OTHER INFORMATION: Synthetic polypeptide

<400> SEQUENCE: 25

Asn Leu Glu Glu Val Glu Phe Cys Val Glu Asp Lys Pro Gly Thr His
1               5                   10                  15

Phe Thr Pro Val Pro Pro Thr Pro Pro Asp Ala Cys Arg
            20                  25

<210> SEQ ID NO 26
<211> LENGTH: 23
```

```
<212> TYPE: PRT
<213> ORGANISM: Artificial sequence
<220> FEATURE:
<223> OTHER INFORMATION: Synthetic polypeptide

<400> SEQUENCE: 26

Gly Glu Ile Glu Glu Thr Ile Thr Glu Ser Phe Gly Asn Asp His Ser
1               5                   10                  15

Thr Leu Asp Gly Tyr Ser Arg
            20

<210> SEQ ID NO 27
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 27

Met Tyr His Thr Lys Gly Gln Glu Gly Ser Val Cys Leu Arg
1               5                   10

<210> SEQ ID NO 28
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 28

Asn Leu Pro Pro Pro Leu Gly Gly Ala Ala Gly His Pro Gly Ser Ala
1               5                   10                  15

Val Ser Ala Ala Pro Gly Ile Leu Tyr Pro Gly Gly Asn Lys
            20                  25                  30

<210> SEQ ID NO 29
<211> LENGTH: 30
<212> TYPE: PRT
<213> ORGANISM: Artificial sequence
<220> FEATURE:
<223> OTHER INFORMATION: Synthetic polypeptide

<400> SEQUENCE: 29

Asn Leu Pro Pro Pro Leu Gly Gly Ser Ala Gly His Pro Gly Ser Ala
1               5                   10                  15

Val Ser Ala Ala Pro Gly Ile Leu Tyr Pro Gly Gly Asn Lys
            20                  25                  30

<210> SEQ ID NO 30
<211> LENGTH: 29
<212> TYPE: PRT
<213> ORGANISM: Artificial sequence
<220> FEATURE:
<223> OTHER INFORMATION: Synthetic polypeptide

<400> SEQUENCE: 30

Tyr Gln Thr Ile Asp Asn Tyr Gln Pro Tyr Pro Cys Ala Glu Asp Glu
1               5                   10                  15

Glu Cys Gly Thr Asp Glu Tyr Cys Ala Ser Pro Thr Arg
            20                  25

<210> SEQ ID NO 31
<211> LENGTH: 20
<212> TYPE: PRT
<213> ORGANISM: Artificial sequence
```

<220> FEATURE:
<223> OTHER INFORMATION: Synthetic polypeptide

<400> SEQUENCE: 31

Leu Ala Gly Thr Glu Ser Pro Val Arg Glu Glu Pro Gly Glu Asp Phe
1               5                   10                  15

Pro Ala Ala Arg
            20

<210> SEQ ID NO 32
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 32

Tyr Ser Gln Ala Val Pro Ala Val Thr Glu Gly Pro Ile Pro Glu Val
1               5                   10                  15

Leu Lys

<210> SEQ ID NO 33
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 33

Leu Pro Ala Leu Thr Val His Val Thr Gln Pro Lys
1               5                   10

<210> SEQ ID NO 34
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 34

Ser Glu Ala Leu Pro Thr Asp Leu Pro Ala Pro Ser Ala Pro Asp Leu
1               5                   10                  15

Thr Glu Pro Lys
            20

<210> SEQ ID NO 35
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 35

Ser Glu Ala Leu Pro Thr Asp Leu Pro Thr Pro Ser Ala Pro Asp Leu
1               5                   10                  15

Thr Glu Pro Lys
            20

<210> SEQ ID NO 36
<211> LENGTH: 15
<212> TYPE: PRT
<213> ORGANISM: Artificial sequence
<220> FEATURE:
<223> OTHER INFORMATION: Synthetic polypeptide
<220> FEATURE:

```
<221> NAME/KEY: MISC_FEATURE
<222> LOCATION: (9)..(9)
<223> OTHER INFORMATION: This amino acid is a glycosite

<400> SEQUENCE: 36

Leu Arg Pro Ile Ile Ile Ser Met Asn Tyr Ser Leu Pro Leu Arg
1               5                   10                  15

<210> SEQ ID NO 37
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 37

Gly Arg Val Pro Thr Ala Ala Pro Pro Ala Gln Pro Arg
1               5                   10

<210> SEQ ID NO 38
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 38

Val Pro Val Thr Pro Ala Pro Ala Val Ile Pro Ile Leu Val Ile Ala
1               5                   10                  15

Cys Asp Arg

<210> SEQ ID NO 39
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 39

His Asp Gly His Asp Asp Val Ile Asp Ile Glu Asp Asp Leu Asp
1               5                   10                  15

Asp Val Ile Glu Glu Val Glu Asp Ser Lys Pro Asp Thr Thr Ala Pro
                20                  25                  30

Pro Ser Ser Pro Lys
            35

<210> SEQ ID NO 40
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 40

Val Thr Tyr Lys Ala Pro Val Pro Thr Gly Glu Val Tyr Phe Ala Asp
1               5                   10                  15

Ser Phe Asp Arg
            20

<210> SEQ ID NO 41
<211> LENGTH: 19
<212> TYPE: PRT
<213> ORGANISM: Artificial sequence
<220> FEATURE:
<223> OTHER INFORMATION: Synthetic polypeptide
```

<400> SEQUENCE: 41

Ala Leu Gly Ser Leu His Leu Pro Thr Asn Pro Thr Ser Leu Pro Ala
1               5                   10                  15

Val Ala Lys

<210> SEQ ID NO 42
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 42

Gln Ala Thr Ala Arg Thr Val Thr Pro Lys
1               5                   10

<210> SEQ ID NO 43
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: This amino acid is a glycosite

<400> SEQUENCE: 43

Thr Ile Leu Val Asp Asn Asn Thr Trp Asn Asn Thr His Ile Ser Arg
1               5                   10                  15

<210> SEQ ID NO 44
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 44

Ser Gly Thr Val Thr Val Ala Gln Gln Ala Gln Val Val Thr Thr Val
1               5                   10                  15

Val Gly Gly Val Thr Lys
            20

<210> SEQ ID NO 45
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 45

Thr Ala Ala Ala Gln Val Gly Thr Ser Val Ser Ser Ala Thr Asn Thr
1               5                   10                  15

Ser Thr Arg Pro Ile Ile Thr Val His Lys
            20                  25

<210> SEQ ID NO 46
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 46

```
Gly Ala Pro Asn Lys Glu Glu Thr Pro Ala Thr Glu Ser Pro Asp Thr
1               5                   10                  15

Gly Leu Tyr Tyr His Arg
            20

<210> SEQ ID NO 47
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 47

Val Ile Lys Pro Thr Ser Ser Asn Thr Ala Gln Gly Arg
1               5                   10

<210> SEQ ID NO 48
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 48

Ser Val Ser Pro Ser Ala Ser Pro Val Val Cys Tyr Gln Ser Asn Arg
1               5                   10                  15

<210> SEQ ID NO 49
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 49

Asp Trp Glu Asn Gln Leu Glu Ala Ser Met His Ser Val Leu Ser Asp
1               5                   10                  15

Leu His Glu Ala Val Pro Thr Val Val Gly Ile Pro Asp Gly Thr Ala
            20                  25                  30

Val Val Gly Arg
        35

<210> SEQ ID NO 50
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 50

Gly Leu Phe Ile Pro Phe Ser Val Ser Ser Thr His Lys
1               5                   10

<210> SEQ ID NO 51
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 51

Glu His Gly Pro Gly Val Ala Glu Pro Glu Val Ala Thr Ala Pro Pro
1               5                   10                  15

Glu Lys Glu Ile Pro Ser Leu Asp Gln Glu Lys
```

20          25

<210> SEQ ID NO 52
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 52

Ile Lys Val Val Phe Thr Pro Ser Ile Cys Lys
1               5                   10

<210> SEQ ID NO 53
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 53

Ser Thr His Pro Pro Pro Leu Pro Ala Lys Glu Glu Pro Val Glu Ala
1               5                   10                  15

Leu Thr Phe Ser Arg
            20

<210> SEQ ID NO 54
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 54

Gly Gly Gly Pro Asp Pro Glu Trp Gly Ser Ala Asn Thr Pro Val Pro
1               5                   10                  15

Gly Ala Pro Ala Pro His Ser Ser
            20

<210> SEQ ID NO 55
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 55

Gly Gly Gly Pro Asp Pro Glu Trp Gly Ser Ala Asn Thr Pro Val Pro
1               5                   10                  15

Gly Ala Pro Ser Pro His Ser Ser
            20

<210> SEQ ID NO 56
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 56

Gly Gly Gly Pro Asp Thr Glu Trp Gly Ser Ala Asn Thr Pro Val Pro
1               5                   10                  15

Gly Ala Pro Ser Pro His Ser Ser
            20

<210> SEQ ID NO 57
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 57

Gly Gly Gly Pro Asp Pro Glu Trp Gly Ser Ala Asn Thr Thr Val Pro
1               5                   10                  15

Gly Ala Pro Ser Pro His Ser Ser
            20

<210> SEQ ID NO 58
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 58

Gly Gly Gly Pro Asp Pro Glu Trp Gly Ser Ser Asn Thr Pro Val Pro
1               5                   10                  15

Gly Ser Pro Ser Pro His Ser Ser
            20

<210> SEQ ID NO 59
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 59

Asp Phe Gln Thr Leu Glu Asn Trp Met Leu Gln Thr Leu Asn Glu Glu
1               5                   10                  15

Pro Val Thr Pro Glu Pro Glu Val Glu Pro Pro Ser Ala Pro Glu Leu
            20                  25                  30

Lys

<210> SEQ ID NO 60
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 60

Ala Gly Ala Gly Pro Ser Pro Ala Gly Asp Asp Val Thr Phe Pro Glu
1               5                   10                  15

Phe Leu Arg

<210> SEQ ID NO 61
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: This amino acid is a glycosite
<220> FEATURE:
<221> NAME/KEY: MISC_FEATURE
<222> LOCATION: (10)..(10)

<223> OTHER INFORMATION: This amino acid is a glycosite

<400> SEQUENCE: 61

Thr Thr Leu Val Asp Asn Asn Thr Trp Asn Asn Ser His Ile Ala Leu
1               5                   10                  15

Val Gly Lys

<210> SEQ ID NO 62
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 62

Val Val Pro Lys Pro Val Val Ala Pro Thr Leu Ser Val Val Gln Thr
1               5                   10                  15

Glu Gly Ser Arg
            20

<210> SEQ ID NO 63
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 63

Glu Pro Glu Asn Glu Ile Ser Ser Asp Cys Asn His Leu Leu Trp Asn
1               5                   10                  15

Tyr Lys

<210> SEQ ID NO 64
<211> LENGTH: 29
<212> TYPE: PRT
<213> ORGANISM: Artificial sequence
<220> FEATURE:
<223> OTHER INFORMATION: Synthetic polypeptide

<400> SEQUENCE: 64

Val Asn Leu Pro Thr Thr Val Ser Asn Phe Asn Asn Pro Ser Pro Ser
1               5                   10                  15

Val Val Thr Ala Thr Thr Ser Val His Glu Ser Asn Lys
            20                  25

<210> SEQ ID NO 65
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: This amino acid is a glycosite

<400> SEQUENCE: 65

Asn Ala Thr Leu Ala Glu Gln Ala Lys
1               5

<210> SEQ ID NO 66
<211> LENGTH: 30
<212> TYPE: PRT
<213> ORGANISM: Artificial sequence
<220> FEATURE:

```
<223> OTHER INFORMATION: Synthetic polypeptide

<400> SEQUENCE: 66

Asn Leu Pro Pro Pro Leu Gly Gly Ala Ala Gly His Pro Gly Ser Ser
1               5                   10                  15

Val Ser Ala Ala Pro Gly Ile Leu Tyr Pro Gly Gly Asn Lys
            20                  25                  30

<210> SEQ ID NO 67
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 67

Ala Glu Ala Gly Ala Arg Pro Glu Glu Asn Leu Ile Leu Asp Ala Gln
1               5                   10                  15

Ala Thr Ser Arg
            20
```